US011261217B2

(12) United States Patent
Chou et al.

(10) Patent No.: US 11,261,217 B2
(45) Date of Patent: Mar. 1, 2022

(54) **EXPRESSION OF *KLEBSIELLA OXYTOCA* POLYPEPTIDES INVOLVED IN LYSINE DECARBOXYLATION, AND METHODS AND APPLICATIONS THEREOF**

(71) Applicants: CATHAY BIOTECH INC., Shanghai (CN); CIBT AMERICA INC., Newark, DE (US)

(72) Inventors: Howard Chou, Shanghai (CN); Naiqiang Li, Shanghai (CN); Xiucai Liu, Shanghai (CN)

(73) Assignees: CATHAY BIOTECH INC., Shanghai (CN); CIBT AMERICA INC., Newark, DE (US)

( * ) Notice: Subject to any disclaimer, the term of this patent is extended or adjusted under 35 U.S.C. 154(b) by 0 days.

(21) Appl. No.: 16/738,663

(22) Filed: Jan. 9, 2020

(65) Prior Publication Data
US 2020/0157152 A1    May 21, 2020

Related U.S. Application Data

(62) Division of application No. 15/547,323, filed as application No. PCT/CN2015/071978 on Jan. 30, 2015, now Pat. No. 10,584,149.

(51) Int. Cl.
| C07K 14/195 | (2006.01) |
| C12N 9/88 | (2006.01) |
| C12P 13/00 | (2006.01) |
| C12N 5/10 | (2006.01) |
| C12N 15/70 | (2006.01) |
| C12P 21/02 | (2006.01) |

(52) U.S. Cl.
CPC .............. *C07K 14/195* (2013.01); *C12N 5/10* (2013.01); *C12N 9/88* (2013.01); *C12N 15/70* (2013.01); *C12P 13/001* (2013.01); *C12P 21/02* (2013.01); *C12N 2510/02* (2013.01); *C12Y 401/01018* (2013.01)

(58) Field of Classification Search
CPC ........ C07K 14/195; C12N 5/10; C12N 15/70; C12N 9/88; C12N 2510/02; C12P 21/02; C12P 13/001; C12Y 401/01018
See application file for complete search history.

(56) References Cited

U.S. PATENT DOCUMENTS

2010/0292429 A1    11/2010  Volkert

FOREIGN PATENT DOCUMENTS

| CN | 101981202 A | 2/2011 |
| CN | 102424811 A | 4/2012 |

OTHER PUBLICATIONS

Whisstock et al. Quaterly Reviews of Biophysics, 2003, "Prediction of protein function from protein sequence and structure", 36(3):307-340.*
Witkowski et al. Conversion of a beta-ketoacyl synthase to a malonyl decarboxylase by replacement of the active-site cysteine with glutamine, Biochemistry. Sep. 7, 1999;38(36):11643-50.*
Search Report and Written Opinion dated Nov. 20, 2015 issued in PCT/CN2015/071978 (11 pages).
"WP_004848492.1" NCBI Reference Sequence, Oct. 10, 2014 (Oct. 10, 2014) (1 pages).
"WP_009652676.1" NCBI Reference Sequence, May 11, 2013 (May 11, 2013) (1 pages).
"WP-001540636.1" NCBI Reference Sequence, May 3, 2013 (May 3, 2013) (1 pages).
The extended European Search Report issued in Application No. 15879438.8 dated Jun. 8, 2018, 7 pages.
Li, Naiqiang et al., "Cadaverine Production by Heterologous Expression of Klebsiella oxytoca Lysine Decarboxylase", Biotechnology and Bioprocess Engineering, Korean Society for Biotechnology and Bioengineering, Seoul, KR, vol. 19, No. 6, Nov. 1, 2014, XP002756871, pp. 965-972.
Papadakis, E.D., et al., "Promoters and Control Elements: Designing Expression Cassettes for Gene Therapy", Bristol Heart Institute, Bristol Royal Infirmay, Bristol, BS2 8HW, UK, Division of Cardiovascular and Medical Sciences, University of Glasgow, Glasgow, G11 6NT, UK, Current Gene Therapy, 2004, 4, 89-113.
Datsenko, Kirill, et al., One-step Inactivation of Chromosomal Genes in *Escherichia coli* K-12 Using PCR Products, Department of Biological Sciences, Purdue Unversity, West Lafeyette, IN 47907, communicated by Jonathan Beckwith, Harvard Medical School, Boston, MA, PNAS, Jun. 6, 2000, vol. 97, No. 12, 6840-8645.

(Continued)

*Primary Examiner* — Iqbal H Chowdhury
(74) *Attorney, Agent, or Firm* — Rothwell, Figg, Ernst & Manbeck, P.C.

(57) ABSTRACT

One aspect provided herein relates to lysine decarboxylase polypeptides comprising mutants of SEQ ID NO: 2 (i.e., mutants of *Klebsiella oxytoca* (*K. oxytoca*) Ldc) and/or fragments thereof. In certain embodiments, the mutants or fragments thereof may have at least about 95% sequence identity with SEQ ID NO: 2. Another aspect provided herein relates to a DNA polynucleotide comprising one or more lysine decarboxylase nucleotide sequences of mutants of SEQ ID NO: 1 (i.e., mutants of *K. oxytoca* ldc), fragments thereof, or fragments of SEQ ID NO: 1 (i.e., fragments of *K. oxytoca* ldc). In certain embodiments, the DNA polynucleotide as disclosed herein may encode one or more lysine decarboxylase polypeptides provided herein. In certain embodiments, the DNA polynucleotide as disclosed herein may encode SEQ ID NO: 2, mutants, and/or fragments thereof. In certain embodiments, the lysine decarboxylase nucleotide sequences provided herein may have at least 95% sequence identity with SEQ ID NO: 1 or SEQ ID NO: 3. Another aspect provided herein relates to expression vectors comprising the DNA polynucleotides described herein used for production of a lysine-derived product. Other aspects provided herein include transformants, mutant host cells, methods for the production of lysine decarboxylases, and methods for the production of a lysine-derived product.

1 Claim, 6 Drawing Sheets

Specification includes a Sequence Listing.

(56) References Cited

OTHER PUBLICATIONS

Wertz, John, et al., Chimeric Nature of Two Plasmids of Hafnia alvei Encoding the Bacteriocins Alveicins A and B, Journal of Bacteriology, Mar. 2004, pp. 1598-1605.
European Communication pursuant to Article 94(3) EPC, issued in Application No. 15 879 438.8, dated May 6, 2019, 4 pages.
Fecker et al. Cloning and characterization of a lysine decarboxylase gene from Hafnia alvei. Mol Gen Genet (1986), 203: 177-184.
European Communication pursuant to Article 94(3) EPC, issued in Application No. 15 879 438.8, dated Nov. 19, 2019, 4 pages.
Communication pursuant to Article 94(3) EPC dated Apr. 22, 2020 issued in European Patent Application No. 15 879 438.8 (4 pages).
Chinese Office Action in corresponding Application No. 201580062908.8, with an English language translation, dated Mar. 26, 2020, 16 pages.
Li, "Efficient expression and directed molecular evolution of lysine decarboxylase and its process characteristics for cadarverine synthesis", with an English Abstract, Jun. 12, 2016.
Naiqiang Li, "Improved cadaverine production from mutant Klebsiella oxytoca lysine decarboxylase" Eng. Life Sci. 2016, 16, 299-305.
Zhi-Gang Qian, "Metabolic Engineering of *Escherichia coli* for the Production of Cadaverine: A Five Carbon Diamine", Biotechnology and Bioengineering, vol. 108, No. 1, Jan. 1, 2011.
Lothar F. Fecker, "Cloning and characterization of a lysine decarboxylase gene from Hafnia alvei" Mot Gen Genet (1986) 203:177-184.
"WP_009652676.1" NCBI Reference Sequence, (1 page) Mar. 13, 2020.

\* cited by examiner

FIG. 1

| Name | Sequence (5'-3') | SEQ ID NO: |
|---|---|---|
| KOldc-F | GGCGAGCTCTTTTACCTGGAGATATGACTATGAACGTTATCGCAATCATG | 27 |
| KOldc-R | GGCTCTAGATTATTTGTTATTTTCTTCTTTCAGCAC | 28 |
| ECcadA-F | GGCGAGCTCTTTTACCTGGAGATATGACTATGAAC | 29 |
| ECcadA-R | GGCTCTAGATTATTTTTTGCTTTCTTCTTTCAATAC | 30 |
| XhoI-F | CAATTAATGTCTCGAGTTAGCTCACTC | 31 |
| XhoI-R | GAGTGAGCTAACTCGAGACATTAATTG | 32 |
| Pbad-F | GGCCTCGAGTTATGACAACTTGACGGCTA | 33 |
| Pbad-R | GGCGAGCTCACAGTAGAGAGTTGCGATAAAAAG | 34 |
| Ptac-F | GGC CTCGAGGCGCCTGATGCGGTATTTTC | 35 |
| Ptac-R | GGC GAGCTCCATTATACGAGCCGATGATTAATTGTC | 36 |
| RBS-F | TTTTACCTNNNNNNNATGACT*ATG*AATGTTATTGCGATTATG | 37 |
| RBS-R | GTTCATAATCGCAATAACATTCAT | 38 |
| epPCR-F | GGCGAGCTCTTTTACCTTGGAGGATGACT*ATG*AATG | 39 |
| epPCR-R | GGCTCTAGATTATTTGTTGTTCTCTTCCTTGAG | 40 |
| RBS-out-F | GGCTGTGCAGGTCGTAAATC | 41 |
| ldc-out-F | TTGACAATTAATCATCGGCT | 42 |
| ldc-out-R | GTTGTAAAACGACGGCCAGT | 43 |

FIG. 2

| Strain | Plasmid | Enzyme | Gene | Promoter | RBS DNA sequence |
|---|---|---|---|---|---|
| CIB60 | pUC18-cadA | E. coli CadA | E. coli cadA | Plac | GGAGAT |
| LN18 | pUC18-KOldc | K. oxytoca Ldc | K. oxytoca ldc | Plac | GGAGAT |
| LN20 | pUC18-KOldc-co1 | K. oxytoca Ldc | K. oxytoca ldc-co1 | Plac | GGAGAT |
| LN22 | pUC18-KOldc-co1-Pbad | K. oxytoca Ldc | K. oxytoca ldc-co1 | Pbad | GGAGAT |
| LN24 | pUC18-KOldc-co1-Ptac | K. oxytoca Ldc | K. oxytoca ldc-co1 | Ptac | GGAGAT |
| LN1100 | pLN140 | K. oxytoca Ldc | K. oxytoca ldc-co1 | Ptac | AGGACT |
| LN1101 | pLN301 | K. oxytoca Ldc | K. oxytoca ldc-co1 | Ptac | GAGGAG |
| LN1102 | pLN499 | K. oxytoca Ldc | K. oxytoca ldc-co1 | Ptac | GAGGAA |
| LN1103 | pLN637 | K. oxytoca Ldc | K. oxytoca ldc-co1 | Ptac | TGGAGG |
| LN1104 | pLN770 | K. oxytoca Ldc | K. oxytoca ldc-co1 | Ptac | CAGGAG |
| LN3010 | pLN2377 | K. oxytoca Ldc K287E | K. oxytoca ldc-co1 A859G | Ptac | TGGAGG |
| LN3011 | pLN2453 | K. oxytoca Ldc R436G | K. oxytoca ldc-co1 C1193G | Ptac | TGGAGG |
| LN3012 | pLN2768 | K. oxytoca Ldc F607Y | K. oxytoca ldc-co1 C1306G | Ptac | TGGAGG |
| LN3013 | pLN2888 | K. oxytoca Ldc T398S | K. oxytoca ldc-co1 C1521G | Ptac | TGGAGG |
| LN3014 | pLN2964 | K. oxytoca Ldc F507L | K. oxytoca ldc-co1 T1820A | Ptac | TGGAGG |

SEQUENCE LISTING

<160> NUMBER OF SEQ ID NOS: 43

<210> SEQ ID NO 1
<211> LENGTH: 2148
<212> TYPE: DNA
<213> ORGANISM: Klebsiella oxytoca

<400> SEQUENCE: 1

| | |
|---|---|
| atgaacgtta tcgcaatcat gaatcacatg ggtgtctact tcaaagaaga acccatccgt | 60 |
| gaactgcatc gcgccctcga acgcctggac ttccgtattg tctacccgaa cgaccgtgaa | 120 |
| gacttattaa aacttatcga aaacaatgcg cgtctgtgcg gcgtgatctt cgactgggat | 180 |
| aaatataatc tcgaactgtg cgaagacatc agcaaaatga cgaatacat gccgctgtac | 240 |
| gcctttgcga acacttactc aacgctggac gtgagcctca acgatctgcg gatgcaggtt | 300 |
| cgcttcttcg aatatgcgct gggcgcagcg gaagacattg ccaacaaaat caaacagaat | 360 |
| accgacgagt atatcgacac cattctgccg ccgctgacca agcgctgtt taaatacgtg | 420 |
| cgtgaaggca aatacacctt ctgtacccca ggccatatgg gcggtaccgc gttccagaaa | 480 |
| agcccagtcg gcagcatctt ctacgatttc tttggttcca ataccatgaa atccgatatc | 540 |
| tcgatttcgg tttctgaact cggttctctg ctggaccaca gcggcccgca caagaagcg | 600 |
| gaagagtaca tcgcccgcgt cttcaacgcg gaacgcagct acatggtgac caacgggacc | 660 |
| tctaccgcca acaaaattgt cggcatgtat tccgccccgg ccggtagcac cgtgctgatt | 720 |
| gaccgtaact gccataaatc gctgacccat ctgatgatga tgagcgacat tacgccaatc | 780 |
| tacttccgcc cgacccgcaa cgcctacggt atcctcggcg gtatcccgca gagcgaattc | 840 |
| cagcatgcga ccatcgcgaa gcgcgtgaaa gaaaccccga acgcgacctg ccgggtgcac | 900 |
| gcggttatca ccaactccac ctatgacggt ctgctgtaca acacggacta catcaagaaa | 960 |
| accctggatg tgaaatccat ccactttgac tccgcgtggg tgccttacac caacttctcg | 1020 |
| ccgatttatg aaggcaaatg cgggatgagc ggcggccgcg tcgaagggaa agtgatttac | 1080 |
| gaaacccagt ccacgcacaa actgctggcg gcgttctctc aggcctcgat gattcacgtt | 1140 |
| aaaggcgacg tgaacgaaga gaccttaac gaagcctaca tgatgcacac caccacttct | 1200 |
| ccgcactacg gcgtggtggc ctcgacggaa accgcggcgg cgatgatgaa aggcaacgcc | 1260 |
| ggtaagcgcc tgattgacgg ctctatcgaa cgttcaatca gttccgtaa agagatcaaa | 1320 |
| cgtctgaaag cgagtccga cggctggttc ttcgacgtct ggcagccgga acatatcgat | 1380 |
| ggcgctgaat gctggccgct cgctccgac agcgcgtggc acggcttcaa aaacatcgat | 1440 |
| aacgagcaca tgtatctcga cccgattaaa gtcacgctgc tgactccggg gatgaagaaa | 1500 |
| gacggcacca tggatgagtt cggtattccg gcgagcatcg tggcgaagta tctcgacgag | 1560 |
| cacggtatcg tggtcgaaaa aaccggtccg tacaacctgc tgttcctgtt cagtatcggt | 1620 |
| atcgacaaaa ccaaagcgct gagcctgctg cgtgcgctga ccgatttcaa acgcgcgttc | 1680 |
| gacctgaacc tgcgggtgaa aaacatgctg ccgtcgctgt atcgtgaaga tccggaattc | 1740 |
| tacgaaaaca tgcgcgttca ggaactggcg cagaacatta taaactgat tgagcaccac | 1800 |
| aacctgccgg atctgatgtt ccgcgcgttc gaagtgctgc cgaccatgat gatcacgccg | 1860 |
| tacgccgcgt tccagaaaga gctgcacggt cagaccgaag aggtgtatct cgaagagatg | 1920 |
| gtgggccgcg tcaacgccaa tatgatcctg ccgtatcctc cgggagtgcc gctggtgatg | 1980 |
| ccgggtgaaa tgatcaccga agagagccgt ccggtgctgg agttcctgca gatgctgtgc | 2040 |
| gaaatcggcg cccactatcc gggcttcgaa accgatatcc acgcgccta tcgtcaggcg | 2100 | gatggtcgtt acaccgttaa agtgctgaaa gaagaaaata acaaataa 2148

<210> SEQ ID NO 2
<211> LENGTH: 715
<212> TYPE: PRT
<213> ORGANISM: Klebsiella oxytoca

<400> SEQUENCE: 2

```
Met Asn Val Ile Ala Ile Met Asn His Met Gly Val Tyr Phe Lys Glu
1               5                   10                  15

Glu Pro Ile Arg Glu Leu His Arg Ala Leu Glu Arg Leu Asp Phe Arg
            20                  25                  30

Ile Val Tyr Pro Asn Asp Arg Glu Asp Leu Leu Lys Leu Ile Glu Asn
        35                  40                  45

Asn Ala Arg Leu Cys Gly Val Ile Phe Asp Trp Asp Lys Tyr Asn Leu
    50                  55                  60

Glu Leu Cys Glu Asp Ile Ser Lys Met Asn Glu Tyr Met Pro Leu Tyr
65                  70                  75                  80

Ala Phe Ala Asn Thr Tyr Ser Thr Leu Asp Val Ser Leu Asn Asp Leu
                85                  90                  95

Arg Met Gln Val Arg Phe Phe Glu Tyr Ala Leu Gly Ala Ala Glu Asp
            100                 105                 110

Ile Ala Asn Lys Ile Lys Gln Asn Thr Asp Glu Tyr Ile Asp Thr Ile
        115                 120                 125

Leu Pro Pro Leu Thr Lys Ala Leu Phe Lys Tyr Val Arg Glu Gly Lys
    130                 135                 140

Tyr Thr Phe Cys Thr Pro Gly His Met Gly Gly Thr Ala Phe Gln Lys
145                 150                 155                 160

Ser Pro Val Gly Ser Ile Phe Tyr Asp Phe Phe Gly Ser Asn Thr Met
                165                 170                 175

Lys Ser Asp Ile Ser Ile Ser Val Ser Glu Leu Gly Ser Leu Leu Asp
            180                 185                 190

His Ser Gly Pro His Lys Glu Ala Glu Glu Tyr Ile Ala Arg Val Phe
        195                 200                 205

Asn Ala Glu Arg Ser Tyr Met Val Thr Asn Gly Thr Ser Thr Ala Asn
    210                 215                 220

Lys Ile Val Gly Met Tyr Ser Ala Pro Ala Gly Ser Thr Val Leu Ile
225                 230                 235                 240

Asp Arg Asn Cys His Lys Ser Leu Thr His Leu Met Met Met Ser Asp
                245                 250                 255

Ile Thr Pro Ile Tyr Phe Arg Pro Thr Arg Asn Ala Tyr Gly Ile Leu
            260                 265                 270

Gly Gly Ile Pro Gln Ser Glu Phe Gln His Ala Thr Ile Ala Lys Arg
        275                 280                 285

Val Lys Glu Thr Pro Asn Ala Thr Trp Pro Val His Ala Val Ile Thr
    290                 295                 300

Asn Ser Thr Tyr Asp Gly Leu Leu Tyr Asn Thr Asp Tyr Ile Lys Lys
305                 310                 315                 320

Thr Leu Asp Val Lys Ser Ile His Phe Asp Ser Ala Trp Val Pro Tyr
                325                 330                 335

Thr Asn Phe Ser Pro Ile Tyr Glu Gly Lys Cys Gly Met Ser Gly Gly
            340                 345                 350

Arg Val Glu Gly Lys Val Ile Tyr Glu Thr Gln Ser Thr His Lys Leu
        355                 360                 365
```

Leu Ala Ala Phe Ser Gln Ala Ser Met Ile His Val Lys Gly Asp Val
    370                 375                 380

Asn Glu Glu Thr Phe Asn Glu Ala Tyr Met Met His Thr Thr Thr Ser
385                 390                 395                 400

Pro His Tyr Gly Val Val Ala Ser Thr Glu Thr Ala Ala Ala Met Met
                405                 410                 415

Lys Gly Asn Ala Gly Lys Arg Leu Ile Asp Gly Ser Ile Glu Arg Ser
            420                 425                 430

Ile Lys Phe Arg Lys Glu Ile Lys Arg Leu Lys Gly Glu Ser Asp Gly
        435                 440                 445

Trp Phe Phe Asp Val Trp Gln Pro Glu His Ile Asp Gly Ala Glu Cys
    450                 455                 460

Trp Pro Leu Arg Ser Asp Ser Ala Trp His Gly Phe Lys Asn Ile Asp
465                 470                 475                 480

Asn Glu His Met Tyr Leu Asp Pro Ile Lys Val Thr Leu Leu Thr Pro
                485                 490                 495

Gly Met Lys Lys Asp Gly Thr Met Asp Glu Phe Gly Ile Pro Ala Ser
            500                 505                 510

Ile Val Ala Lys Tyr Leu Asp Glu His Gly Ile Val Val Glu Lys Thr
        515                 520                 525

Gly Pro Tyr Asn Leu Leu Phe Leu Phe Ser Ile Gly Ile Asp Lys Thr
    530                 535                 540

Lys Ala Leu Ser Leu Leu Arg Ala Leu Thr Asp Phe Lys Arg Ala Phe
545                 550                 555                 560

Asp Leu Asn Leu Arg Val Lys Asn Met Leu Pro Ser Leu Tyr Arg Glu
                565                 570                 575

Asp Pro Glu Phe Tyr Glu Asn Met Arg Val Gln Glu Leu Ala Gln Asn
            580                 585                 590

Ile His Lys Leu Ile Glu His His Asn Leu Pro Asp Leu Met Phe Arg
        595                 600                 605

Ala Phe Glu Val Leu Pro Thr Met Met Ile Thr Pro Tyr Ala Ala Phe
    610                 615                 620

Gln Lys Glu Leu His Gly Gln Thr Glu Glu Val Tyr Leu Glu Glu Met
625                 630                 635                 640

Val Gly Arg Val Asn Ala Asn Met Ile Leu Pro Tyr Pro Pro Gly Val
                645                 650                 655

Pro Leu Val Met Pro Gly Glu Met Ile Thr Glu Glu Ser Arg Pro Val
            660                 665                 670

Leu Glu Phe Leu Gln Met Leu Cys Glu Ile Gly Ala His Tyr Pro Gly
        675                 680                 685

Phe Glu Thr Asp Ile His Gly Ala Tyr Arg Gln Ala Asp Gly Arg Tyr
    690                 695                 700

Thr Val Lys Val Leu Lys Glu Glu Asn Asn Lys
705                 710                 715

<210> SEQ ID NO 3
<211> LENGTH: 2148
<212> TYPE: DNA
<213> ORGANISM: Artifical
<220> FEATURE:
<223> OTHER INFORMATION: synthetic

<400> SEQUENCE: 3
atgaatgtta ttgcgattat gaaccacatg ggcgtatact tcaaggagga accgatccgc        60

```
gaactgcatc gtgccctgga acgtctggat ttccgcatcg tctatccaaa tgaccgtgag    120
gatctcctca agctcatcga gaataatgcg cgcctgtgtg gtgttatctt tgactgggac    180
aaatacaatc tggaactgtg cgaggacatc tctaagatga acgaatatat gccgctgtac    240
gcgtttgcca acacctactc taccctcgac gttagcctga atgacctgcg catgcaggtt    300
cgtttctttg aatacgcgct gggtgcggcg aagacattg caaacaagat caaacaaaac     360
accgacgagt acattgatac gatcctccct cctctcacca agctctgtt caagtacgtc     420
cgcgagggca agtacacttt tgcacccct ggtcatatgg gcggcactgc gtttcagaaa     480
agcccggttg gttccatttt ctatgacttt tttggttcta atacgatgaa atctgatatc    540
tctatctctg tttccgaact cggctccctg ctggaccact ctggtccgca taagaagca     600
gaagaataca tcgcgcgtgt tttcaacgcg aacgctctt acatggtaac gaacggcacc     660
agcaccgcga ataagattgt tggtatgtat agcgctccag cgggctctac cgtactcatt    720
gaccgtaact gccataaaag cctgactcac ctcatgatga tgtccgacat cactccaatt    780
tacttccgtc cgacccgtaa tgcctatggc atcctgggtg cattcctca gtctgaattt     840
caacacgcca ctattgctaa gcgtgtaaag gagactccaa acgctacgtg gcctgtccac    900
gccgttatca ccaactccac ctacgacggt ctcctgtaca atactgatta catcaaaaaa    960
accctggatg taaaatccat tcacttcgat agcgcatggg ttccttacac taacttcagc   1020
ccaatctatg agggtaagtg cggtatgagc ggtggtcgtg tcgaaggcaa agttatctac   1080
gagacgcaaa gcactcacaa actcctggca gcgttctctc aagcgtccat gattcatgtt   1140
aagggtgacg tgaatgaaga gaccttcaac gaagcgtaca tgatgcatac caccacctct   1200
ccgcactacg gtgtcgttgc gtccacggaa acggcggctg ctatgatgaa aggtaatgcg   1260
ggtaaacgcc tgatcgacgg ttctattgag cgtagcatca aatttcgtaa agaaatcaaa   1320
cgtctcaaag gtgaaagcga cggctggttt ttcgatgtgt ggcagccaga acatattgat   1380
ggtgctgaat gctggccgct gcgttctgac tccgcttggc acggtttcaa aaacatcgac   1440
aatgaacaca tgtacctgga cccgatcaag gttacgctcc tgaccccagg tatgaaaaaa   1500
gacggtacta tggatgaatt cggtattccg gcctccatcg tggcgaagta tctcgacgaa   1560
catggcattg ttgtggagaa gacgggtccg tataacctgc tgtttctgtt ttccatcggc   1620
attgacaaaa cgaaagcgct gtctctgctg cgtgcgctga ccgactttaa acgtgcgttc   1680
gacctgaatc tccgtgttaa gaacatgctc ccgtctctgt accgtgaaga cccggaattc   1740
tacgaaaaca tgcgtgttca ggaactggcg cagaatatcc acaagctgat tgagcatcac   1800
aacctcccgg atctcatgtt ccgtgccttt gaagttctcc aacgatgat gattactccg    1860
tatgcggcgt tccaaaaaga gctgcatggc caaacggaag aggtgtacct cgaagaaatg   1920
gtcggtcgcg ttaatgctaa tatgattctc ccgtatccac ctggtgtgcc tctcgttatg   1980
ccaggcgaaa tgatcactga agagtcccgc ccagtgctcg aatttctgca aatgctgtgt   2040
gaaattggcg cccactaccc aggcttcgaa accgatattc atggcgctta ccgccaagca   2100
gatggtcgct acacggttaa agtactcaag gaagagaaca acaaataa                2148
```

<210> SEQ ID NO 4
<211> LENGTH: 2148
<212> TYPE: DNA
<213> ORGANISM: Artifical
<220> FEATURE:
<223> OTHER INFORMATION: synthetic

<400> SEQUENCE: 4

-continued

```
atgaatgtta ttgcgattat gaaccacatg ggcgtatact tcaaggagga accgatccgc    60
gaactgcatc gtgccctgga acgtctggat ttccgcatcg tctatccaaa tgaccgtgag   120
gatctcctca agctcatcga gaataatgcg cgcctgtgtg gtgttatctt tgactgggac   180
aaatacaatc tggaactgtg cgaggacatc tctaagatga acgaatatat gccgctgtac   240
gcgtttgcca acacctactc taccctcgac gttagcctga atgacctgcg catgcaggtt   300
cgtttctttg aatacgcgct gggtgcggcg aagacattg caaacaagat caaacaaaac    360
accgacgagt acattgatac gatcctccct cctctcacca agctctgtt caagtacgtc    420
cgcgagggca agtacacttt tgcaccccct ggtcatatgg gcggcactgc gtttcagaaa   480
agcccggttg gttccatttt ctatgacttt tttggttcta atacgatgaa atctgatatc   540
tctatctctg tttccgaact cggctccctg ctggaccact ctggtccgca taagaagca    600
gaagaataca tcgcgcgtgt tttcaacgcg aacgctctt acatggtaac gaacggcacc    660
agcaccgcga ataagattgt tggtatgtat agcgctccag cgggctctac cgtactcatt   720
gaccgtaact gccataaaag cctgactcac ctcatgatga tgtccgacat cactccaatt   780
tacttccgtc cgacccgtaa tgcctatggc atcctgggtg cattcctca gtctgaattt    840
caacacgcca ctattgctga gcgtgtaaag gagactccaa acgctacgtg gcctgtccac   900
gccgttatca ccaactccac ctacgacggt ctcctgtaca atactgatta catcaaaaaa   960
accctggatg taaaatccat tcacttcgat agcgcatggg ttccttacac taacttcagc  1020
ccaatctatg agggtaagtg cggtatgagc ggtggtcgtg tcgaaggcaa agttatctac  1080
gagacgcaaa gcactcacaa actcctggca gcgttctctc aagcgtccat gattcatgtt  1140
aagggtgacg tgaatgaaga gaccttcaac gaagcgtaca tgatgcatac caccacctct  1200
ccgcactacg gtgtcgttgc gtccacggaa acggcggctg ctatgatgaa aggtaatgcg  1260
ggtaaacgcc tgatcgacgg ttctattgag cgtagcatca aatttcgtaa agaaatcaaa  1320
cgtctcaaag gtgaaagcga cggctggttt ttcgatgtgt ggcagccaga acatattgat  1380
ggtgctgaat gctggccgct gcgttctgac tccgcttggc acggtttcaa aaacatcgac  1440
aatgaacaca tgtacctgga cccgatcaag gttacgctcc tgaccccagg tatgaaaaaa  1500
gacggtacta tggatgaatt cggtattccg gcctccatcg tggcgaagta tctcgacgaa  1560
catggcattg ttgtggagaa gacgggtccg tataacctgc tgtttctgtt ttccatcggc  1620
attgacaaaa cgaaagcgct gtctctgctg cgtgcgctga ccgactttaa acgtgcgttc  1680
gacctgaatc tccgtgttaa gaacatgctc cgtctctgt accgtgaaga cccggaattc   1740
tacgaaaaca tgcgtgttca ggaactggcg cagaatatcc acaagctgat tgagcatcac  1800
aacctcccgg atctcatgtt ccgtgccttt gaagttctcc aacgatgat gattactccg    1860
tatgcggcgt tccaaaaaga gctgcatggc caaacggaag aggtgtacct cgaagaaatg  1920
gtcggtcgcg ttaatgctaa tatgattctc ccgtatccac ctggtgtgcc tctcgttatg  1980
ccaggcgaaa tgatcactga gagtcccgc ccagtgctcg aatttctgca aatgctgtgt    2040
gaaattggcg cccactaccc aggcttcgaa accgatattc atggcgctta ccgccaagca  2100
gatggtcgct acacggttaa agtactcaag gaagagaaca caaataa                2148
```

<210> SEQ ID NO 5
<211> LENGTH: 715
<212> TYPE: PRT
<213> ORGANISM: Artifical
<220> FEATURE:

<223> OTHER INFORMATION: synthetic

<400> SEQUENCE: 5

```
Met Asn Val Ile Ala Ile Met Asn His Met Gly Val Tyr Phe Lys Glu
1               5                   10                  15

Glu Pro Ile Arg Glu Leu His Arg Ala Leu Glu Arg Leu Asp Phe Arg
            20                  25                  30

Ile Val Tyr Pro Asn Asp Arg Glu Asp Leu Leu Lys Leu Ile Glu Asn
        35                  40                  45

Asn Ala Arg Leu Cys Gly Val Ile Phe Asp Trp Asp Lys Tyr Asn Leu
    50                  55                  60

Glu Leu Cys Glu Asp Ile Ser Lys Met Asn Glu Tyr Met Pro Leu Tyr
65                  70                  75                  80

Ala Phe Ala Asn Thr Tyr Ser Thr Leu Asp Val Ser Leu Asn Asp Leu
                85                  90                  95

Arg Met Gln Val Arg Phe Phe Glu Tyr Ala Leu Gly Ala Ala Glu Asp
            100                 105                 110

Ile Ala Asn Lys Ile Lys Gln Asn Thr Asp Glu Tyr Ile Asp Thr Ile
        115                 120                 125

Leu Pro Pro Leu Thr Lys Ala Leu Phe Lys Tyr Val Arg Glu Gly Lys
    130                 135                 140

Tyr Thr Phe Cys Thr Pro Gly His Met Gly Gly Thr Ala Phe Gln Lys
145                 150                 155                 160

Ser Pro Val Gly Ser Ile Phe Tyr Asp Phe Phe Gly Ser Asn Thr Met
                165                 170                 175

Lys Ser Asp Ile Ser Ile Ser Val Ser Glu Leu Gly Ser Leu Leu Asp
            180                 185                 190

His Ser Gly Pro His Lys Glu Ala Glu Glu Tyr Ile Ala Arg Val Phe
        195                 200                 205

Asn Ala Glu Arg Ser Tyr Met Val Thr Asn Gly Thr Ser Thr Ala Asn
    210                 215                 220

Lys Ile Val Gly Met Tyr Ser Ala Pro Ala Gly Ser Thr Val Leu Ile
225                 230                 235                 240

Asp Arg Asn Cys His Lys Ser Leu Thr His Leu Met Met Met Ser Asp
                245                 250                 255

Ile Thr Pro Ile Tyr Phe Arg Pro Thr Arg Asn Ala Tyr Gly Ile Leu
            260                 265                 270

Gly Gly Ile Pro Gln Ser Glu Phe Gln His Ala Thr Ile Ala Glu Arg
        275                 280                 285

Val Lys Glu Thr Pro Asn Ala Thr Trp Pro Val His Ala Val Ile Thr
    290                 295                 300

Asn Ser Thr Tyr Asp Gly Leu Leu Tyr Asn Thr Asp Tyr Ile Lys Lys
305                 310                 315                 320

Thr Leu Asp Val Lys Ser Ile His Phe Asp Ser Ala Trp Val Pro Tyr
                325                 330                 335

Thr Asn Phe Ser Pro Ile Tyr Glu Gly Lys Cys Gly Met Ser Gly Gly
            340                 345                 350

Arg Val Glu Gly Lys Val Ile Tyr Glu Thr Gln Ser Thr His Lys Leu
        355                 360                 365

Leu Ala Ala Phe Ser Gln Ala Ser Met Ile His Val Lys Gly Asp Val
    370                 375                 380

Asn Glu Glu Thr Phe Asn Glu Ala Tyr Met Met His Thr Thr Thr Ser
385                 390                 395                 400
```

```
Pro His Tyr Gly Val Ala Ser Thr Glu Thr Ala Ala Ala Met Met
            405                 410                 415

Lys Gly Asn Ala Gly Lys Arg Leu Ile Asp Gly Ser Ile Glu Arg Ser
        420                 425                 430

Ile Lys Phe Arg Lys Glu Ile Lys Arg Leu Lys Gly Glu Ser Asp Gly
        435                 440                 445

Trp Phe Phe Asp Val Trp Gln Pro Glu His Ile Asp Gly Ala Glu Cys
        450                 455                 460

Trp Pro Leu Arg Ser Asp Ser Ala Trp His Gly Phe Lys Asn Ile Asp
465                 470                 475                 480

Asn Glu His Met Tyr Leu Asp Pro Ile Lys Val Thr Leu Leu Thr Pro
                485                 490                 495

Gly Met Lys Lys Asp Gly Thr Met Asp Glu Phe Gly Ile Pro Ala Ser
            500                 505                 510

Ile Val Ala Lys Tyr Leu Asp Glu His Gly Ile Val Val Glu Lys Thr
        515                 520                 525

Gly Pro Tyr Asn Leu Leu Phe Leu Phe Ser Ile Gly Ile Asp Lys Thr
        530                 535                 540

Lys Ala Leu Ser Leu Leu Arg Ala Leu Thr Asp Phe Lys Arg Ala Phe
545                 550                 555                 560

Asp Leu Asn Leu Arg Val Lys Asn Met Leu Pro Ser Leu Tyr Arg Glu
                565                 570                 575

Asp Pro Glu Phe Tyr Glu Asn Met Arg Val Gln Glu Leu Ala Gln Asn
            580                 585                 590

Ile His Lys Leu Ile Glu His His Asn Leu Pro Asp Leu Met Phe Arg
        595                 600                 605

Ala Phe Glu Val Leu Pro Thr Met Met Ile Thr Pro Tyr Ala Ala Phe
        610                 615                 620

Gln Lys Glu Leu His Gly Gln Thr Glu Glu Val Tyr Leu Glu Glu Met
625                 630                 635                 640

Val Gly Arg Val Asn Ala Asn Met Ile Leu Pro Tyr Pro Pro Gly Val
                645                 650                 655

Pro Leu Val Met Pro Gly Glu Met Ile Thr Glu Glu Ser Arg Pro Val
            660                 665                 670

Leu Glu Phe Leu Gln Met Leu Cys Glu Ile Gly Ala His Tyr Pro Gly
        675                 680                 685

Phe Glu Thr Asp Ile His Gly Ala Tyr Arg Gln Ala Asp Gly Arg Tyr
        690                 695                 700

Thr Val Lys Val Leu Lys Glu Glu Asn Asn Lys
705                 710                 715

<210> SEQ ID NO 6
<211> LENGTH: 2148
<212> TYPE: DNA
<213> ORGANISM: Artifical
<220> FEATURE:
<223> OTHER INFORMATION: synthetic

<400> SEQUENCE: 6
atgaatgtta ttgcgattat gaaccacatg ggcgtatact tcaaggagga accgatccgc      60
gaactgcatc gtgccctgga acgtctggat ttccgcatcg tctatccaaa tgaccgtgag     120
gatctcctca agctcatcga gaataatgcg cgcctgtgtg gtgttatctt tgactgggac     180
aaatacaatc tggaactgtg cgaggacatc tctaagatga cgaatatat gccgctgtac     240 gcgtttgcca acacctactc taccctcgac gttagcctga tgacctgcg catgcaggtt     300
```

```
cgtttctttg aatacgcgct gggtgcggcg aagacattg caaacaagat caaacaaaac      360
accgacgagt acattgatac gatcctccct cctctcacca agctctgtt caagtacgtc      420
cgcgagggca agtacacttt ttgcacccct ggtcatatgg gcggcactgc gtttcagaaa     480
agcccggttg gttccatttt ctatgacttt tttggttcta atacgatgaa atctgatatc     540
tctatctctg tttccgaact cggctccctg ctggaccact ctggtccgca taagaagca      600
gaagaataca tcgcgcgtgt tttcaacgcg aacgctctt acatggtaac gaacggcacc      660
agcaccgcga ataagattgt tggtatgtat agcgctccag cgggctctac cgtactcatt     720
gaccgtaact gccataaaag cctgactcac ctcatgatga tgtccgacat cactccaatt     780
tacttccgtc cgacccgtaa tgcctatggc atcctgggtg gcattcctca gtctgaattt     840
caacacgcca ctattgctaa gcgtgtaaag gagactccaa acgctacgtg gcctgtccac     900
gccgttatca ccaactccac ctacgacggt ctcctgtaca atactgatta tcaaaaaaa      960
accctggata taaatccat tcacttcgat agcgcatggg ttccttacac taacttcagc     1020
ccaatctatg agggtaagtg cggtatgagc ggtggtcgtg tcgaaggcaa agttatctac     1080
gagacgcaaa gcactcacaa actcctggca gcgttctctc aagcgtccat gattcatgtt     1140
aagggtgacg tgaatgaaga gaccttcaac gaagcgtaca tgatgcatac cagcacctct     1200
ccgcactacg tgtcgttgc gtccacggaa acggcggctg ctatgatgaa aggtaatgcg     1260
ggtaaacgcc tgatcgacgg ttctattgag cgtagcatca aatttcgtaa agaaatcaaa     1320
cgtctcaaag gtgaaagcga cggctggttt ttcgatgtgt ggcagccaga acatattgat     1380
ggtgctgaat gctggccgct gcgttctgac tccgcttggc acggttcaa aaacatcgac     1440
aatgaacaca tgtacctgga cccgatcaag gttacgctcc tgaccccagg tatgaaaaaa    1500
gacggtacta tggatgaatt cggtattccg gcctccatcg tggcgaagta tctcgacgaa    1560
catggcattg ttgtggagaa acggggtccg tataacctgc tgtttctgtt ttccatcggc    1620
attgacaaaa cgaaagcgct gtctctgctg cgtgcgctga ccgactttaa acgtgcgttc    1680
gacctgaatc tccgtgttaa gaacatgctc ccgtctctgt accgtgaaga cccggaattc    1740
tacgaaaaca tgcgtgttca ggaactggcg cagaatatcc acaagctgat tgagcatcac    1800
aacctcccgg atctcatgtt ccgtgccttt gaagttctcc caacgatgat gattactccg    1860
tatgcggcgt tccaaaaaga gctgcatggc caaacggaag aggtgtacct cgaagaaatg    1920
gtcggtcgcg ttaatgctaa tatgattctc ccgtatccac ctggtgtgcc tctcgttatg    1980
ccaggcgaaa tgatcactga agagtcccgc ccagtgctcg aatttctgca aatgctgtgt    2040
gaaattggcg cccactaccc aggcttcgaa accgatattc atggcgctta ccgccaagca    2100
gatggtcgct acacggttaa agtactcaag gaagagaaca acaaataa                 2148
```

<210> SEQ ID NO 7
<211> LENGTH: 715
<212> TYPE: PRT
<213> ORGANISM: Artifical
<220> FEATURE:
<223> OTHER INFORMATION: synthetic

<400> SEQUENCE: 7

Met Asn Val Ile Ala Ile Met Asn His Met Gly Val Tyr Phe Lys Glu
1               5                   10                  15

Glu Pro Ile Arg Glu Leu His Arg Ala Leu Glu Arg Leu Asp Phe Arg
            20                  25                  30

```
Ile Val Tyr Pro Asn Asp Arg Glu Asp Leu Leu Lys Leu Ile Glu Asn
                35                  40                  45

Asn Ala Arg Leu Cys Gly Val Ile Phe Asp Trp Asp Lys Tyr Asn Leu
 50                  55                  60

Glu Leu Cys Glu Asp Ile Ser Lys Met Asn Glu Tyr Met Pro Leu Tyr
 65                  70                  75                  80

Ala Phe Ala Asn Thr Tyr Ser Thr Leu Asp Val Ser Leu Asn Asp Leu
                85                  90                  95

Arg Met Gln Val Arg Phe Phe Glu Tyr Ala Leu Gly Ala Ala Glu Asp
                100                 105                 110

Ile Ala Asn Lys Ile Lys Gln Asn Thr Asp Glu Tyr Ile Asp Thr Ile
                115                 120                 125

Leu Pro Pro Leu Thr Lys Ala Leu Phe Lys Tyr Val Arg Glu Gly Lys
                130                 135                 140

Tyr Thr Phe Cys Thr Pro Gly His Met Gly Gly Thr Ala Phe Gln Lys
145                 150                 155                 160

Ser Pro Val Gly Ser Ile Phe Tyr Asp Phe Phe Gly Ser Asn Thr Met
                165                 170                 175

Lys Ser Asp Ile Ser Ile Ser Val Ser Glu Leu Gly Ser Leu Leu Asp
                180                 185                 190

His Ser Gly Pro His Lys Glu Ala Glu Glu Tyr Ile Ala Arg Val Phe
                195                 200                 205

Asn Ala Glu Arg Ser Tyr Met Val Thr Asn Gly Thr Ser Thr Ala Asn
                210                 215                 220

Lys Ile Val Gly Met Tyr Ser Ala Pro Ala Gly Ser Thr Val Leu Ile
225                 230                 235                 240

Asp Arg Asn Cys His Lys Ser Leu Thr His Leu Met Met Met Ser Asp
                245                 250                 255

Ile Thr Pro Ile Tyr Phe Arg Pro Thr Arg Asn Ala Tyr Gly Ile Leu
                260                 265                 270

Gly Gly Ile Pro Gln Ser Glu Phe Gln His Ala Thr Ile Ala Lys Arg
                275                 280                 285

Val Lys Glu Thr Pro Asn Ala Thr Trp Pro Val His Ala Val Ile Thr
290                 295                 300

Asn Ser Thr Tyr Asp Gly Leu Leu Tyr Asn Thr Asp Tyr Ile Lys Lys
305                 310                 315                 320

Thr Leu Asp Val Lys Ser Ile His Phe Asp Ser Ala Trp Val Pro Tyr
                325                 330                 335

Thr Asn Phe Ser Pro Ile Tyr Glu Gly Lys Cys Gly Met Ser Gly Gly
                340                 345                 350

Arg Val Glu Gly Lys Val Ile Tyr Glu Thr Gln Ser Thr His Lys Leu
                355                 360                 365

Leu Ala Ala Phe Ser Gln Ala Ser Met Ile His Val Lys Gly Asp Val
                370                 375                 380

Asn Glu Glu Thr Phe Asn Glu Ala Tyr Met Met His Thr Ser Thr Ser
385                 390                 395                 400

Pro His Tyr Gly Val Val Ala Ser Thr Glu Thr Ala Ala Ala Met Met
                405                 410                 415

Lys Gly Asn Ala Gly Lys Arg Leu Ile Asp Gly Ser Ile Glu Arg Ser
                420                 425                 430

Ile Lys Phe Arg Lys Glu Ile Lys Arg Leu Lys Gly Glu Ser Asp Gly
                435                 440                 445

Trp Phe Phe Asp Val Trp Gln Pro Glu His Ile Asp Gly Ala Glu Cys
```

```
               450              455              460
Trp Pro Leu Arg Ser Asp Ser Ala Trp His Gly Phe Lys Asn Ile Asp
465              470              475              480

Asn Glu His Met Tyr Leu Asp Pro Ile Lys Val Thr Leu Leu Thr Pro
                 485              490              495

Gly Met Lys Lys Asp Gly Thr Met Asp Glu Phe Gly Ile Pro Ala Ser
                 500              505              510

Ile Val Ala Lys Tyr Leu Asp Glu His Gly Ile Val Val Glu Lys Thr
             515              520              525

Gly Pro Tyr Asn Leu Leu Phe Leu Phe Ser Ile Gly Ile Asp Lys Thr
         530              535              540

Lys Ala Leu Ser Leu Leu Arg Ala Leu Thr Asp Phe Lys Arg Ala Phe
545              550              555              560

Asp Leu Asn Leu Arg Val Lys Asn Met Leu Pro Ser Leu Tyr Arg Glu
                 565              570              575

Asp Pro Glu Phe Tyr Glu Asn Met Arg Val Gln Glu Leu Ala Gln Asn
                 580              585              590

Ile His Lys Leu Ile Glu His His Asn Leu Pro Asp Leu Met Phe Arg
             595              600              605

Ala Phe Glu Val Leu Pro Thr Met Met Ile Thr Pro Tyr Ala Ala Phe
         610              615              620

Gln Lys Glu Leu His Gly Gln Thr Glu Glu Val Tyr Leu Glu Glu Met
625              630              635              640

Val Gly Arg Val Asn Ala Asn Met Ile Leu Pro Tyr Pro Pro Gly Val
                 645              650              655

Pro Leu Val Met Pro Gly Glu Met Ile Thr Glu Glu Ser Arg Pro Val
                 660              665              670

Leu Glu Phe Leu Gln Met Leu Cys Glu Ile Gly Ala His Tyr Pro Gly
             675              680              685

Phe Glu Thr Asp Ile His Gly Ala Tyr Arg Gln Ala Asp Gly Arg Tyr
         690              695              700

Thr Val Lys Val Leu Lys Glu Glu Asn Asn Lys
705              710              715
```

<210> SEQ ID NO 8
<211> LENGTH: 2148
<212> TYPE: DNA
<213> ORGANISM: Artifical
<220> FEATURE:
<223> OTHER INFORMATION: synthetic

<400> SEQUENCE: 8

```
atgaatgtta ttgcgattat gaaccacatg ggcgtatact tcaaggagga accgatccgc    60
gaactgcatc gtgccctgga acgtctggat ttccgcatcg tctatccaaa tgaccgtgag   120
gatctcctca agctcatcga gaataatgcg cgcctgtgtg gtgttatctt tgactgggac   180
aaatacaatc tggaactgtg cgaggacatc tctaagatga cgaatatat gccgctgtac   240
gcgtttgcca cacctactc tacccctcgac gttagcctga tgacctgcg catgcaggtt   300
cgtttctttg aatacgcgct gggtgcggcg aagacattg caaacaagat caaacaaaac   360
accgacgagt acattgatac gatcctccct cctctcacca agctctgtt caagtacgtc   420
cgcgagggca agtacacttt ttgcacccct ggtcatatgg gcggcactgc gtttcagaaa   480
agcccggttg ttccattttt ctatgacttt tttggttcta atacgatgaa atctgatatc   540
tctatctctg tttccgaact cggctccctg ctggaccact ctggtccgca taagaagca   600
```

```
gaagaataca tcgcgcgtgt tttcaacgcg gaacgctctt acatggtaac gaacggcacc      660
agcaccgcga ataagattgt tggtatgtat agcgctccag cgggctctac cgtactcatt      720
gaccgtaact gccataaaag cctgactcac ctcatgatga tgtccgacat cactccaatt      780
tacttccgtc cgaccgtaa tgcctatggc atcctgggtg cattcctca gtctgaattt       840 caacacgcca ctattgctaa gcgtgtaaag gagactccaa acgctacgtg gcctgtccac      900
gccgttatca ccaactccac ctacgacggt ctcctgtaca atactgatta catcaaaaaa      960
accctggatg taaaatccat tcacttcgat agcgcatggg ttccttacac taacttcagc     1020
ccaatctatg agggtaagtg cggtatgagc ggtggtcgtg tcgaaggcaa agttatctac     1080
gagacgcaaa gcactcacaa actcctggca gcgttctctc aagcgtccat gattcatgtt     1140
aagggtgacg tgaatgaaga gaccttcaac gaagcgtaca tgatgcatac caccacctct     1200
ccgcactacg gtgtcgttgc gtccacggaa acggcggctg ctatgatgaa aggtaatgcg     1260
ggtaaacgcc tgatcgacgg ttctattgag cgtagcatca aatttggtaa agaaatcaaa     1320
cgtctcaaag gtgaaagcga cggctggttt ttcgatgtgt ggcagccaga acatattgat     1380
ggtgctgaat gctggccgct gcgttctgac tccgcttggc acggtttcaa aaacatcgac     1440
aatgaacaca tgtacctgga cccgatcaag gttacgctcc tgaccccagg tatgaaaaaa     1500
gacggtacta tggatgaatt cggtattccg gcctccatcg tggcgaagta tctcgacgaa     1560
catggcattg ttgtggagaa gacgggtccg tataacctgc tgtttctgtt ttccatcggc     1620
attgacaaaa cgaaagcgct gtctctgctg cgtgcgctga ccgactttaa acgtgcgttc     1680
gacctgaatc tccgtgttaa gaacatgctc ccgtctctgt accgtgaaga cccggaattc     1740
tacgaaaaca tgcgtgttca ggaactggcg cagaatatcc acaagctgat tgagcatcac     1800
aacctcccgg atctcatgtt ccgtgccttt gaagttctcc caacgatgat gattactccg     1860
tatgcggcgt tccaaaaaga gctgcatggc caaacggaag aggtgtacct cgaagaaatg     1920
gtcggtcgcg ttaatgctaa tatgattctc ccgtatccac ctggtgtgcc tctcgttatg     1980
ccaggcgaaa tgatcactga agagtcccgc ccagtgctcg aatttctgca aatgctgtgt     2040
gaaattggcg cccactaccc aggcttcgaa accgatattc atggcgctta ccgccaagca     2100
gatggtcgct acacggttaa agtactcaag gaagagaaca acaaataa                  2148
```

<210> SEQ ID NO 9
<211> LENGTH: 715
<212> TYPE: PRT
<213> ORGANISM: Artifical
<220> FEATURE:
<223> OTHER INFORMATION: synthetic

<400> SEQUENCE: 9

Met Asn Val Ile Ala Ile Met Asn His Met Gly Val Tyr Phe Lys Glu
1               5                   10                  15

Glu Pro Ile Arg Glu Leu His Arg Ala Leu Glu Arg Leu Asp Phe Arg
            20                  25                  30

Ile Val Tyr Pro Asn Asp Arg Glu Asp Leu Leu Lys Leu Ile Glu Asn
        35                  40                  45

Asn Ala Arg Leu Cys Gly Val Ile Phe Asp Trp Asp Lys Tyr Asn Leu
    50                  55                  60

Glu Leu Cys Glu Asp Ile Ser Lys Met Asn Glu Tyr Met Pro Leu Tyr
65                  70                  75                  80

Ala Phe Ala Asn Thr Tyr Ser Thr Leu Asp Val Ser Leu Asn Asp Leu

```
                    85                  90                  95
Arg Met Gln Val Arg Phe Phe Glu Tyr Ala Leu Gly Ala Ala Glu Asp
                100                 105                 110

Ile Ala Asn Lys Ile Lys Gln Asn Thr Asp Glu Tyr Ile Asp Thr Ile
                115                 120                 125

Leu Pro Pro Leu Thr Lys Ala Leu Phe Lys Tyr Val Arg Glu Gly Lys
            130                 135                 140

Tyr Thr Phe Cys Thr Pro Gly His Met Gly Gly Thr Ala Phe Gln Lys
145                 150                 155                 160

Ser Pro Val Gly Ser Ile Phe Tyr Asp Phe Phe Gly Ser Asn Thr Met
                165                 170                 175

Lys Ser Asp Ile Ser Ile Ser Val Ser Glu Leu Gly Ser Leu Leu Asp
                180                 185                 190

His Ser Gly Pro His Lys Glu Ala Glu Glu Tyr Ile Ala Arg Val Phe
                195                 200                 205

Asn Ala Glu Arg Ser Tyr Met Val Thr Asn Gly Thr Ser Thr Ala Asn
            210                 215                 220

Lys Ile Val Gly Met Tyr Ser Ala Pro Ala Gly Ser Thr Val Leu Ile
225                 230                 235                 240

Asp Arg Asn Cys His Lys Ser Leu Thr His Leu Met Met Met Ser Asp
                245                 250                 255

Ile Thr Pro Ile Tyr Phe Arg Pro Thr Arg Asn Ala Tyr Gly Ile Leu
                260                 265                 270

Gly Gly Ile Pro Gln Ser Glu Phe Gln His Ala Thr Ile Ala Lys Arg
            275                 280                 285

Val Lys Glu Thr Pro Asn Ala Thr Trp Pro Val His Ala Val Ile Thr
290                 295                 300

Asn Ser Thr Tyr Asp Gly Leu Leu Tyr Asn Thr Asp Tyr Ile Lys Lys
305                 310                 315                 320

Thr Leu Asp Val Lys Ser Ile His Phe Asp Ser Ala Trp Val Pro Tyr
                325                 330                 335

Thr Asn Phe Ser Pro Ile Tyr Glu Gly Lys Cys Gly Met Ser Gly Gly
            340                 345                 350

Arg Val Glu Gly Lys Val Ile Tyr Glu Thr Gln Ser Thr His Lys Leu
            355                 360                 365

Leu Ala Ala Phe Ser Gln Ala Ser Met Ile His Val Lys Gly Asp Val
            370                 375                 380

Asn Glu Glu Thr Phe Asn Glu Ala Tyr Met Met His Thr Thr Thr Ser
385                 390                 395                 400

Pro His Tyr Gly Val Val Ala Ser Thr Glu Thr Ala Ala Ala Met Met
                405                 410                 415

Lys Gly Asn Ala Gly Lys Arg Leu Ile Asp Gly Ser Ile Glu Arg Ser
                420                 425                 430

Ile Lys Phe Gly Lys Glu Ile Lys Arg Leu Lys Gly Glu Ser Asp Gly
            435                 440                 445

Trp Phe Phe Asp Val Trp Gln Pro Glu His Ile Asp Gly Ala Glu Cys
            450                 455                 460

Trp Pro Leu Arg Ser Asp Ser Ala Trp His Gly Phe Lys Asn Ile Asp
465                 470                 475                 480

Asn Glu His Met Tyr Leu Asp Pro Ile Lys Val Thr Leu Leu Thr Pro
                485                 490                 495

Gly Met Lys Lys Asp Gly Thr Met Asp Glu Phe Gly Ile Pro Ala Ser
                500                 505                 510
```

Ile Val Ala Lys Tyr Leu Asp Glu His Gly Ile Val Val Glu Lys Thr
            515                 520                 525

Gly Pro Tyr Asn Leu Leu Phe Leu Phe Ser Ile Gly Ile Asp Lys Thr
        530                 535                 540

Lys Ala Leu Ser Leu Leu Arg Ala Leu Thr Asp Phe Lys Arg Ala Phe
545                 550                 555                 560

Asp Leu Asn Leu Arg Val Lys Asn Met Leu Pro Ser Leu Tyr Arg Glu
                565                 570                 575

Asp Pro Glu Phe Tyr Glu Asn Met Arg Val Gln Glu Leu Ala Gln Asn
            580                 585                 590

Ile His Lys Leu Ile Glu His His Asn Leu Pro Asp Leu Met Phe Arg
        595                 600                 605

Ala Phe Glu Val Leu Pro Thr Met Met Ile Thr Pro Tyr Ala Ala Phe
    610                 615                 620

Gln Lys Glu Leu His Gly Gln Thr Glu Glu Val Tyr Leu Glu Glu Met
625                 630                 635                 640

Val Gly Arg Val Asn Ala Asn Met Ile Leu Pro Tyr Pro Pro Gly Val
                645                 650                 655

Pro Leu Val Met Pro Gly Glu Met Ile Thr Glu Glu Ser Arg Pro Val
            660                 665                 670

Leu Glu Phe Leu Gln Met Leu Cys Glu Ile Gly Ala His Tyr Pro Gly
        675                 680                 685

Phe Glu Thr Asp Ile His Gly Ala Tyr Arg Gln Ala Asp Gly Arg Tyr
    690                 695                 700

Thr Val Lys Val Leu Lys Glu Glu Asn Asn Lys
705                 710                 715

<210> SEQ ID NO 10
<211> LENGTH: 2148
<212> TYPE: DNA
<213> ORGANISM: Artifical
<220> FEATURE:
<223> OTHER INFORMATION: synthetic

<400> SEQUENCE: 10
atgaatgtta ttgcgattat gaaccacatg gcgtatact tcaaggagga accgatccgc      60
gaactgcatc gtgccctgga acgtctggat ttccgcatcg tctatccaaa tgaccgtgag     120
gatctcctca agctcatcga gaataatgcg cgcctgtgtg gtgttatctt tgactgggac     180
aaatacaatc tggaactgtg cgaggacatc tctaagatga cgaatatat gccgctgtac     240 gcgtttgcca acacctactc taccctcgac gttagcctga tgacctgcg catgcaggtt     300 cgttttcttg aatacgcgct gggtgcggcg aagacattg caaacaagat caaacaaaac     360
accgacgagt acattgatac gatcctccct cctctcacca agctctgtt caagtacgtc     420 cgcgagggca agtacacttt tgcacccct ggtcatatgg gcggcactgc gttcagaaa      480 agcccggttg gttccattt ctatgacttt tttggttcta atcgatgaa atctgatatc      540 tctatctctg tttccgaact cggctccctg ctggaccact ctggtccgca taagaagca     600 gaagaataca tcgcgcgtgt tttcaacgcg aacgctctt acatggtaac gaacggcacc      660
agcaccgcga ataagattgt tggtatgtat agcgctccag cgggctctac cgtactcatt     720
gaccgtaact gccataaaag cctgactcac ctcatgatga tgtccgacat cactccaatt     780
tacttccgtc cgaccgtaa tgcctatggc atctgggtg cattcctca gtctgaattt       840 caacacgcca ctattgctaa gcgtgtaaag gagactccaa acgctacgtg gcctgtccac     900

```
gccgttatca ccaactccac ctacgacggt ctcctgtaca atactgatta catcaaaaaa    960
accctggatg taaaatccat tcacttcgat agcgcatggg ttccttacac taacttcagc   1020
ccaatctatg agggtaagtg cggtatgagc ggtggtcgtg tcgaaggcaa agttatctac   1080
gagacgcaaa gcactcacaa actcctggca gcgttctctc aagcgtccat gattcatgtt   1140
aagggtgacg tgaatgaaga gaccttcaac gaagcgtaca tgatgcatac caccacctct   1200
ccgcactacg gtgtcgttgc gtccacggaa acggcggctg ctatgatgaa aggtaatgcg   1260
ggtaaacgcc tgatcgacgg ttctattgag cgtagcatca aatttcgtaa agaaatcaaa   1320
cgtctcaaag gtgaaagcga cggctggttt ttcgatgtgt ggcagccaga acatattgat   1380
ggtgctgaat gctggccgct gcgttctgac tccgcttggc acggtttcaa aacatcgac    1440
aatgaacaca tgtacctgga cccgatcaag gttacgctcc tgaccccagg tatgaaaaaa   1500
gacggtacta tggatgaatt gggtattccg gcctccatcg tggcgaagta tctcgacgaa   1560
catggcattt tgtgtgagaa gacgggtccg tataacctgc tgtttctgtt ttccatcggc   1620
attgacaaaa cgaaagcgct gtctctgctg cgtgcgctga ccgactttaa acgtgcgttc   1680
gacctgaatc tccgtgttaa gaacatgctc ccgtctctgt accgtgaaga cccggaattc   1740
tacgaaaaca tgcgtgttca ggaactggcg cagaatatcc acaagctgat tgagcatcac   1800
aacctcccgg atctcatgtt ccgtgccttt gaagttctcc caacgatgat gattactccg   1860
tatgcggcgt tccaaaaaga gctgcatggc caaacggaag aggtgtacct cgaagaaatg   1920
gtcggtcgcg ttaatgctaa tatgattctc ccgtatccac ctggtgtgcc tctcgttatg   1980
ccaggcgaaa tgatcactga agagtcccgc ccagtgctcg aatttctgca aatgctgtgt   2040
gaaattggcg cccactaccc aggcttcgaa accgatattc atggcgctta ccgccaagca   2100
gatggtcgct acacggttaa agtactcaag gaagagaaca caaataa                 2148
```

<210> SEQ ID NO 11
<211> LENGTH: 715
<212> TYPE: PRT
<213> ORGANISM: Artifical
<220> FEATURE:
<223> OTHER INFORMATION: synthetic

<400> SEQUENCE: 11

```
Met Asn Val Ile Ala Ile Met Asn His Met Gly Val Tyr Phe Lys Glu
1               5                   10                  15

Glu Pro Ile Arg Glu Leu His Arg Ala Leu Glu Arg Leu Asp Phe Arg
            20                  25                  30

Ile Val Tyr Pro Asn Asp Arg Glu Asp Leu Leu Lys Leu Ile Glu Asn
        35                  40                  45

Asn Ala Arg Leu Cys Gly Val Ile Phe Asp Trp Asp Lys Tyr Asn Leu
    50                  55                  60

Glu Leu Cys Glu Asp Ile Ser Lys Met Asn Glu Tyr Met Pro Leu Tyr
65                  70                  75                  80

Ala Phe Ala Asn Thr Tyr Ser Thr Leu Asp Val Ser Leu Asn Asp Leu
                85                  90                  95

Arg Met Gln Val Arg Phe Phe Glu Tyr Ala Leu Gly Ala Ala Glu Asp
            100                 105                 110

Ile Ala Asn Lys Ile Lys Gln Asn Thr Asp Glu Tyr Ile Asp Thr Ile
        115                 120                 125

Leu Pro Pro Leu Thr Lys Ala Leu Phe Lys Tyr Val Arg Glu Gly Lys
    130                 135                 140
```

```
Tyr Thr Phe Cys Thr Pro Gly His Met Gly Gly Thr Ala Phe Gln Lys
145                 150                 155                 160

Ser Pro Val Gly Ser Ile Phe Tyr Asp Phe Phe Gly Ser Asn Thr Met
                165                 170                 175

Lys Ser Asp Ile Ser Ile Ser Val Ser Glu Leu Gly Ser Leu Leu Asp
                180                 185                 190

His Ser Gly Pro His Lys Glu Ala Glu Glu Tyr Ile Ala Arg Val Phe
            195                 200                 205

Asn Ala Glu Arg Ser Tyr Met Val Thr Asn Gly Thr Ser Thr Ala Asn
210                 215                 220

Lys Ile Val Gly Met Tyr Ser Ala Pro Ala Gly Ser Thr Val Leu Ile
225                 230                 235                 240

Asp Arg Asn Cys His Lys Ser Leu Thr His Leu Met Met Met Ser Asp
                245                 250                 255

Ile Thr Pro Ile Tyr Phe Arg Pro Thr Arg Asn Ala Tyr Gly Ile Leu
                260                 265                 270

Gly Gly Ile Pro Gln Ser Glu Phe Gln His Ala Thr Ile Ala Lys Arg
                275                 280                 285

Val Lys Glu Thr Pro Asn Ala Thr Trp Pro Val His Ala Val Ile Thr
290                 295                 300

Asn Ser Thr Tyr Asp Gly Leu Leu Tyr Asn Thr Asp Tyr Ile Lys Lys
305                 310                 315                 320

Thr Leu Asp Val Lys Ser Ile His Phe Asp Ser Ala Trp Val Pro Tyr
                325                 330                 335

Thr Asn Phe Ser Pro Ile Tyr Glu Gly Lys Cys Gly Met Ser Gly Gly
                340                 345                 350

Arg Val Glu Gly Lys Val Ile Tyr Glu Thr Gln Ser Thr His Lys Leu
                355                 360                 365

Leu Ala Ala Phe Ser Gln Ala Ser Met Ile His Val Lys Gly Asp Val
    370                 375                 380

Asn Glu Glu Thr Phe Asn Glu Ala Tyr Met Met His Thr Thr Thr Ser
385                 390                 395                 400

Pro His Tyr Gly Val Val Ala Ser Thr Glu Thr Ala Ala Ala Met Met
                405                 410                 415

Lys Gly Asn Ala Gly Lys Arg Leu Ile Asp Gly Ser Ile Glu Arg Ser
                420                 425                 430

Ile Lys Phe Arg Lys Glu Ile Lys Arg Leu Lys Gly Glu Ser Asp Gly
                435                 440                 445

Trp Phe Phe Asp Val Trp Gln Pro Glu His Ile Asp Gly Ala Glu Cys
                450                 455                 460

Trp Pro Leu Arg Ser Asp Ser Ala Trp His Gly Phe Lys Asn Ile Asp
465                 470                 475                 480

Asn Glu His Met Tyr Leu Asp Pro Ile Lys Val Thr Leu Leu Thr Pro
                485                 490                 495

Gly Met Lys Lys Asp Gly Thr Met Asp Glu Leu Gly Ile Pro Ala Ser
                500                 505                 510

Ile Val Ala Lys Tyr Leu Asp Glu His Gly Ile Val Val Glu Lys Thr
                515                 520                 525

Gly Pro Tyr Asn Leu Leu Phe Leu Phe Ser Ile Gly Ile Asp Lys Thr
                530                 535                 540

Lys Ala Leu Ser Leu Leu Arg Ala Leu Thr Asp Phe Lys Arg Ala Phe
545                 550                 555                 560
```

Asp Leu Asn Leu Arg Val Lys Asn Met Leu Pro Ser Leu Tyr Arg Glu
             565                 570                 575

Asp Pro Glu Phe Tyr Glu Asn Met Arg Val Gln Glu Leu Ala Gln Asn
         580                 585                 590

Ile His Lys Leu Ile Glu His His Asn Leu Pro Asp Leu Met Phe Arg
     595                 600                 605

Ala Phe Glu Val Leu Pro Thr Met Met Ile Thr Pro Tyr Ala Ala Phe
 610                 615                 620

Gln Lys Glu Leu His Gly Gln Thr Glu Glu Val Tyr Leu Glu Glu Met
625                 630                 635                 640

Val Gly Arg Val Asn Ala Asn Met Ile Leu Pro Tyr Pro Pro Gly Val
             645                 650                 655

Pro Leu Val Met Pro Gly Glu Met Ile Thr Glu Glu Ser Arg Pro Val
         660                 665                 670

Leu Glu Phe Leu Gln Met Leu Cys Glu Ile Gly Ala His Tyr Pro Gly
     675                 680                 685

Phe Glu Thr Asp Ile His Gly Ala Tyr Arg Gln Ala Asp Gly Arg Tyr
 690                 695                 700

Thr Val Lys Val Leu Lys Glu Glu Asn Asn Lys
705                 710                 715

<210> SEQ ID NO 12
<211> LENGTH: 2148
<212> TYPE: DNA
<213> ORGANISM: Artifical
<220> FEATURE:
<223> OTHER INFORMATION: synthetic

<400> SEQUENCE: 12
atgaatgtta ttgcgattat gaaccacatg ggcgtatact tcaaggagga accgatccgc     60
gaactgcatc gtgccctgga acgtctggat ttccgcatcg tctatccaaa tgaccgtgag    120
gatctcctca agctcatcga gaataatgcg cgcctgtgtg gtgttatctt tgactgggac    180
aaatacaatc tggaactgtg cgaggacatc tctaagatga cgaatatat gccgctgtac    240
gcgtttgcca cacctactc tacccctcgac gttagcctga tgacctgcg catgcaggtt    300
cgtttctttg aatacgcgct gggtgcggcg aagacattg caaacaagat caaacaaaac    360
accgacgagt acattgatac gatcctccct cctctcacca aagctctgtt caagtacgtc    420
cgcgagggca agtacacttt ttgcacccct ggtcatatgg gcggcactgc gtttcagaaa    480
agcccggttg gttccatttt ctatgacttt tttggttcta atacgatgaa atctgatatc    540
tctatctctg tttccgaact cggctccctg ctggaccact ctggtccgca taagaagca    600
gaagaataca tcgcgcgtgt tttcaacgcg aacgctcctt acatggtaac gaacggcacc    660
agcaccgcga ataagattgt tggtatgtat agcgctccag cgggctctac cgtactcatt    720
gaccgtaact gccataaaag cctgactcac ctcatgatga tgtccgacat cactccaatt    780
tacttccgtc cgacccgtaa tgcctatggc atcctgggtg cattcctca gtctgaattt    840
caacacgcca ctattgctaa gcgtgtaaag gagactccaa acgctacgtg gcctgtccac    900
gccgttatca ccaactccac ctacgacggt ctcctgtaca atactgatta tcaaaaaaa    960
accctggatg taaaatccat tcacttcgat agcgcatggg ttccttacac taacttcagc   1020
ccaatctatg agggtaagtg cggtatgagc ggtggtcgtg tcgaaggcaa agttatctac   1080
gagacgcaaa gcactcacaa actcctggca gcgttctctc aagcgtccat gattcatgtt   1140
aagggtgacg tgaatgaaga gaccttcaac gaagcgtaca tgatgcatac caccacctct   1200

```
ccgcactacg gtgtcgttgc gtccacggaa acggcggctg ctatgatgaa aggtaatgcg    1260
ggtaaacgcc tgatcgacgg ttctattgag cgtagcatca aatttcgtaa agaaatcaaa    1320
cgtctcaaag gtgaaagcga cggctggttt tcgatgtgt ggcagccaga acatattgat    1380
ggtgctgaat gctggccgct gcgttctgac tccgcttggc acggtttcaa aaacatcgac    1440
aatgaacaca tgtacctgga cccgatcaag gttacgctcc tgaccccagg tatgaaaaaa    1500
gacggtacta tggatgaatt cggtattccg gcctccatcg tggcgaagta tctcgacgaa    1560
catggcattg ttgtggagaa gacgggtccg tataacctgc tgtttctgtt ttccatcggc    1620
attgacaaaa cgaaagcgct gtctctgctg cgtgcgctga ccgactttaa acgtgcgttc    1680
gacctgaatc tccgtgttaa gaacatgctc ccgtctctgt accgtgaaga cccggaattc    1740
tacgaaaaca tgcgtgttca ggaactggcg cagaatatcc acaagctgat tgagcatcac    1800
aacctcccgg atctcatgta ccgtgccttt gaagttctcc caacgatgat gattactccg    1860
tatgcggcgt tccaaaaaga gctgcatggc caaacggaag aggtgtacct cgaagaaatg    1920
gtcggtcgcg ttaatgctaa tatgattctc ccgtatccac ctggtgtgcc tctcgttatg    1980
ccaggcgaaa tgatcactga agagtcccgc ccagtgctcg aatttctgca aatgctgtgt    2040
gaaattggcg cccactaccc aggcttcgaa accgatattc atggcgctta ccgccaagca    2100
gatggtcgct acacggttaa agtactcaag gaagagaaca caaataa                  2148
```

<210> SEQ ID NO 13
<211> LENGTH: 715
<212> TYPE: PRT
<213> ORGANISM: Artifical
<220> FEATURE:
<223> OTHER INFORMATION: synthetic

<400> SEQUENCE: 13

```
Met Asn Val Ile Ala Ile Met Asn His Met Gly Val Tyr Phe Lys Glu
1               5                   10                  15

Glu Pro Ile Arg Glu Leu His Arg Ala Leu Glu Arg Leu Asp Phe Arg
            20                  25                  30

Ile Val Tyr Pro Asn Asp Arg Glu Asp Leu Leu Lys Leu Ile Glu Asn
        35                  40                  45

Asn Ala Arg Leu Cys Gly Val Ile Phe Asp Trp Asp Lys Tyr Asn Leu
    50                  55                  60

Glu Leu Cys Glu Asp Ile Ser Lys Met Asn Glu Tyr Met Pro Leu Tyr
65                  70                  75                  80

Ala Phe Ala Asn Thr Tyr Ser Thr Leu Asp Val Ser Leu Asn Asp Leu
                85                  90                  95

Arg Met Gln Val Arg Phe Phe Glu Tyr Ala Leu Gly Ala Ala Glu Asp
            100                 105                 110

Ile Ala Asn Lys Ile Lys Gln Asn Thr Asp Glu Tyr Ile Asp Thr Ile
        115                 120                 125

Leu Pro Pro Leu Thr Lys Ala Leu Phe Lys Tyr Val Arg Glu Gly Lys
    130                 135                 140

Tyr Thr Phe Cys Thr Pro Gly His Met Gly Gly Thr Ala Phe Gln Lys
145                 150                 155                 160

Ser Pro Val Gly Ser Ile Phe Tyr Asp Phe Phe Gly Ser Asn Thr Met
                165                 170                 175

Lys Ser Asp Ile Ser Ile Ser Val Ser Glu Leu Gly Ser Leu Leu Asp
            180                 185                 190
```

-continued

His Ser Gly Pro His Lys Glu Ala Glu Glu Tyr Ile Ala Arg Val Phe
        195                 200                 205

Asn Ala Glu Arg Ser Tyr Met Val Thr Asn Gly Thr Ser Thr Ala Asn
    210                 215                 220

Lys Ile Val Gly Met Tyr Ser Ala Pro Ala Gly Ser Thr Val Leu Ile
225                 230                 235                 240

Asp Arg Asn Cys His Lys Ser Leu Thr His Leu Met Met Met Ser Asp
                245                 250                 255

Ile Thr Pro Ile Tyr Phe Arg Pro Thr Arg Asn Ala Tyr Gly Ile Leu
            260                 265                 270

Gly Gly Ile Pro Gln Ser Glu Phe Gln His Ala Thr Ile Ala Lys Arg
        275                 280                 285

Val Lys Glu Thr Pro Asn Ala Thr Trp Pro Val His Ala Val Ile Thr
    290                 295                 300

Asn Ser Thr Tyr Asp Gly Leu Leu Tyr Asn Thr Asp Tyr Ile Lys Lys
305                 310                 315                 320

Thr Leu Asp Val Lys Ser Ile His Phe Asp Ser Ala Trp Val Pro Tyr
                325                 330                 335

Thr Asn Phe Ser Pro Ile Tyr Glu Gly Lys Cys Gly Met Ser Gly Gly
            340                 345                 350

Arg Val Glu Gly Lys Val Ile Tyr Glu Thr Gln Ser Thr His Lys Leu
        355                 360                 365

Leu Ala Ala Phe Ser Gln Ala Ser Met Ile His Val Lys Gly Asp Val
    370                 375                 380

Asn Glu Glu Thr Phe Asn Glu Ala Tyr Met Met His Thr Thr Thr Ser
385                 390                 395                 400

Pro His Tyr Gly Val Val Ala Ser Thr Glu Thr Ala Ala Ala Met Met
                405                 410                 415

Lys Gly Asn Ala Gly Lys Arg Leu Ile Asp Gly Ser Ile Glu Arg Ser
            420                 425                 430

Ile Lys Phe Arg Lys Glu Ile Lys Arg Leu Lys Gly Glu Ser Asp Gly
        435                 440                 445

Trp Phe Phe Asp Val Trp Gln Pro Glu His Ile Asp Gly Ala Glu Cys
    450                 455                 460

Trp Pro Leu Arg Ser Asp Ser Ala Trp His Gly Phe Lys Asn Ile Asp
465                 470                 475                 480

Asn Glu His Met Tyr Leu Asp Pro Ile Lys Val Thr Leu Leu Thr Pro
                485                 490                 495

Gly Met Lys Lys Asp Gly Thr Met Asp Glu Phe Gly Ile Pro Ala Ser
            500                 505                 510

Ile Val Ala Lys Tyr Leu Asp Glu His Gly Ile Val Val Glu Lys Thr
        515                 520                 525

Gly Pro Tyr Asn Leu Leu Phe Leu Phe Ser Ile Gly Ile Asp Lys Thr
    530                 535                 540

Lys Ala Leu Ser Leu Leu Arg Ala Leu Thr Asp Phe Lys Arg Ala Phe
545                 550                 555                 560

Asp Leu Asn Leu Arg Val Lys Asn Met Leu Pro Ser Leu Tyr Arg Glu
                565                 570                 575

Asp Pro Glu Phe Tyr Glu Asn Met Arg Val Gln Glu Leu Ala Gln Asn
            580                 585                 590

Ile His Lys Leu Ile Glu His His Asn Leu Pro Asp Leu Met Phe Arg
        595                 600                 605

Ala Phe Glu Val Leu Pro Thr Met Met Ile Thr Pro Tyr Ala Ala Phe

```
                610                 615                 620
Gln Lys Glu Leu His Gly Gln Thr Glu Glu Val Tyr Leu Glu Glu Met
625                 630                 635                 640

Val Gly Arg Val Asn Ala Asn Met Ile Leu Pro Tyr Pro Pro Gly Val
                645                 650                 655

Pro Leu Val Met Pro Gly Glu Met Ile Thr Glu Glu Ser Arg Pro Val
                660                 665                 670

Leu Glu Phe Leu Gln Met Leu Cys Glu Ile Gly Ala His Tyr Pro Gly
                675                 680                 685

Phe Glu Thr Asp Ile His Gly Ala Tyr Arg Gln Ala Asp Gly Arg Tyr
                690                 695                 700

Thr Val Lys Val Leu Lys Glu Glu Asn Asn Lys
705                 710                 715

<210> SEQ ID NO 14
<211> LENGTH: 10
<212> TYPE: DNA
<213> ORGANISM: Artifical
<220> FEATURE:
<223> OTHER INFORMATION: synthetic
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (9)..(10)
<223> OTHER INFORMATION: n is a, c, g, or t

<400> SEQUENCE: 14 nnggagatnn                                                                10

<210> SEQ ID NO 15
<211> LENGTH: 10
<212> TYPE: DNA
<213> ORGANISM: Artifical
<220> FEATURE:
<223> OTHER INFORMATION: synthetic
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (9)..(10)
<223> OTHER INFORMATION: n is a, c, g, or t

<400> SEQUENCE: 15 nnaggactnn                                                                10

<210> SEQ ID NO 16
<211> LENGTH: 10
<212> TYPE: DNA
<213> ORGANISM: Artifical
<220> FEATURE:
<223> OTHER INFORMATION: synthetic
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (9)..(10)
<223> OTHER INFORMATION: n is a, c, g, or t

<400> SEQUENCE: 16 nngaggagnn                                                                10
```

```
<210> SEQ ID NO 17
<211> LENGTH: 10
<212> TYPE: DNA
<213> ORGANISM: Artifical
<220> FEATURE:
<223> OTHER INFORMATION: synthetic
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (9)..(10)
<223> OTHER INFORMATION: n is a, c, g, or t

<400> SEQUENCE: 17 nngaggaann                                                              10

<210> SEQ ID NO 18
<211> LENGTH: 10
<212> TYPE: DNA
<213> ORGANISM: Artifical
<220> FEATURE:
<223> OTHER INFORMATION: synthetic
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (9)..(10)
<223> OTHER INFORMATION: n is a, c, g, or t

<400> SEQUENCE: 18 nntggaggnn                                                              10

<210> SEQ ID NO 19
<211> LENGTH: 10
<212> TYPE: DNA
<213> ORGANISM: Artifical
<220> FEATURE:
<223> OTHER INFORMATION: synthetic
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (9)..(10)
<223> OTHER INFORMATION: n is a, c, g, or t

<400> SEQUENCE: 19 nncaggagnn                                                              10

<210> SEQ ID NO 20
<211> LENGTH: 31
<212> TYPE: DNA
<213> ORGANISM: Artifical
<220> FEATURE:
<223> OTHER INFORMATION: synthetic

<400> SEQUENCE: 20
tttacacttt atgcttccgg ctcgtatgtt g                                      31

<210> SEQ ID NO 21
<211> LENGTH: 28
<212> TYPE: DNA
<213> ORGANISM: Artifical
<220> FEATURE:
```

<223> OTHER INFORMATION: synthetic

<400> SEQUENCE: 21
gacgcttttt atcgcaactc tctactgt                                          28

<210> SEQ ID NO 22
<211> LENGTH: 29
<212> TYPE: DNA
<213> ORGANISM: Artifical
<220> FEATURE:
<223> OTHER INFORMATION: synthetic

<400> SEQUENCE: 22
ttgacaatta atcatcggct cgtataatg                                         29

<210> SEQ ID NO 23
<211> LENGTH: 1333
<212> TYPE: DNA
<213> ORGANISM: Hafnia alvei

<400> SEQUENCE: 23
ttgactttgt taaaagtcag gcataagatc aaaatactgt atatataaca atgtatttat        60
atacagtatt ttatactttt tatctaacgt cagagagggc aatattatga gtggtggaga       120
tggcaagggt cacaatagtg gagcacatga ttccggtggc agcattaatg gaacttctgg       180
gaaaggtggg ccatcaagcg gaggagcatc agataattct gggtggagtt cggaaaataa       240
cccgtggggc ggtggtaact cgggaatgat tggtggcagt caaggaggta acggagctaa       300
tcatggtggc gaaaatacat cttctaacta tgggaaagat gtatcacgcc aaatcggtga       360
tgcgatagcc agaaaggaag gcatcaatcc gaaaatattc actgggtact ttatccgttc       420
agatggatat ttgatcggaa taacgccact tgtcagtggt gatgcctttg gcgttaatct       480
tggcctgttc aataacaatc aaaatagtag tagtgaaaat aagggatgga atggaaggaa       540
tggagatggc attaaaaata gtagccaagg tggatggaag attaaaacta atgaacttac       600
ttcaaaccaa gtagctgctg ctaaatccgt tccagaacct aaaaatagta atattataa        660
gtccatgaga gaagctagcg atgaggttat taattctaat ttaaaccaag ggcatggagt       720
tggtgaggca gctagagctg aaagagatta cagagaaaaa gtaaagaacg caatcaatga       780
taatagtccc aatgtgctac aggatgctat taaatttaca gcagattttt ataaggaagt       840
ttttaacgct tacggagaaa aagccgaaaa actagccaag ttattagctg atcaagctaa       900
aggtaaaaag atccgcaatg tagaagatgc attgaaatct tatgaaaaac acaaggctaa       960
cattaacaaa aaaatcaatg cgaaagatcg cgaagctatc gccaaggctt tggagtctat      1020
ggatgtagaa aaagccgcaa aaatatatc caagttcagc aaaggactag gttgggttgg      1080
cccagctatc gatataactg attggtttac agaattatac aaagcagtga aaactgataa      1140
ttggagatct ctttatgtta aaactgaaac tattgcagta gggctagctg caacccatgt      1200
caccgcctta gcattcagtg ctgtcttggg tgggcctata ggtattttag ttatggtttt      1260
gattatggct ggggttgggg cgttagttaa cgagacaata gttgacgagg caaataaggt      1320
cattgggatt taa                                                        1333

<210> SEQ ID NO 24
<211> LENGTH: 336
<212> TYPE: DNA
<213> ORGANISM: Hafnia alvei

<400> SEQUENCE: 24

```
ctatattttta gcggtcacat tttttatttc aaaacaaaca gaaagaacac caataggaat      60
tgatgtcata aaaataaaaa taaaatacaa agtcattaaa tatgttttttg gcacaccatc     120 cttaaaaaaa cctgttttcc aaaattcttt tttcgtatat ctaagcgctg ctttctctat     180
tagaaaccga gagaaaggaa atagaatagc gctagccaaa ccaagattc tgagcgcaat      240 tattttaggt tcgtcatcac cataactggc gtaaagaata caagcagcca taaagtatcc     300
ccaaaacata ttatgtatgt aatatttcct tgtcat                                336
```

<210> SEQ ID NO 25
<211> LENGTH: 1077
<212> TYPE: DNA
<213> ORGANISM: Hafnia alvei

<400> SEQUENCE: 25

```
atgagtggtg gagacggtaa aggtcacaat agtggagcac atgattccgg tggcagcatt      60
aatggaactt cggggaaagg tggacctgat tctggtggcg gatattggga caaccatcca     120
catattacaa tcaccggtgg acgggaagta ggtcaagggg gagctggtat caactggggt     180
ggtggttctg gtcatggtaa cggcgggggc tcagttgcca tccaagaata taacacgagt     240
aaatatccta acacgggagg atttcctcct cttggagacg ctagctggct gttaaatcct     300
ccaaaatggt cggttattga agtaaaatca gaaaactcag catggcgctc ttatattact     360
catgttcaag gtcatgttta caaattgact tttgatggta cgggtaagct cattgatacc     420
gcgtatgtta attatgaacc cagtgatgat actcgttgga gcccgcttaa aagttttaaa     480
tataataaag gaaccgctga aaaacaggtt agggatgcca ttaacaatga aaaagaagca     540
gttaaggacg ctgttaaatt tactgcagac ttctataaag aggtttttaa ggtttacgga     600
gaaaaagccg agaagctcgc taagttatta gcagatcaag ctaaaggcaa aaaggttcgc     660
aacgtagaag atgccttgaa atcttatgaa aaatataaga ctaacattaa caaaaaaatc     720
aatgcgaaag atcgcgaagc tattgctaaa gccttggagt ctatggatgt aggaaaagcc     780
gcaaaaaata tagccaagtt cagtaaagga ctaggttggg ttggccctgc tatcgatata     840
actgattggt ttacagaatt atacaaggca gtggaaactg ataattggag atcttttat     900 gttaaaactg aaactattgc agtagggcta gctgcaaccc atgttgccgc cttggcattc     960
agcgctgtct tgggtgggcc tgtaggtatt ttggttatgg ttgattat ggctggggtt     1020 ggggcgttag ttaatgagac aatagttgac gaggcaaata aggttattgg gctttaa      1077
```

<210> SEQ ID NO 26
<211> LENGTH: 336
<212> TYPE: DNA
<213> ORGANISM: Hafnia alvei

<400> SEQUENCE: 26

```
ctataattta gcggtcacat tttttatttc aaaaaaaaca gaaataacac ctataggaat      60
tgatgtcata aaaataaaaa ttaaatacaa agtcattaaa tatgttttttg gcacgccatc     120 cttaaaaaaa ccagttttccc aaaattcttt tttcgtatat ctaagcgcgg ttttctctat     180
taaaaaccga gagaaaggga ataggatagc actagccaaa ccaagattc tgagcgcaat      240 tattttaggt tcgttatccc cataactggc gtaaagaata caacagcca taaagtaccc     300 ccaaaacata ttatgtatat aatatttcct tgtcat                                336
```

<210> SEQ ID NO 27

```
<211> LENGTH: 50
<212> TYPE: DNA
<213> ORGANISM: Artificial
<220> FEATURE:
<223> OTHER INFORMATION: primer KOldc-F

<400> SEQUENCE: 27
ggcgagctct tttacctgga gatatgacta tgaacgttat cgcaatcatg          50

<210> SEQ ID NO 28
<211> LENGTH: 36
<212> TYPE: DNA
<213> ORGANISM: Artificial
<220> FEATURE:
<223> OTHER INFORMATION: primer KOldc-R

<400> SEQUENCE: 28
ggctctagat tatttgttat tttcttcttt cagcac                         36

<210> SEQ ID NO 29
<211> LENGTH: 35
<212> TYPE: DNA
<213> ORGANISM: Artificial
<220> FEATURE:
<223> OTHER INFORMATION: primer ECcadA-F

<400> SEQUENCE: 29
ggcgagctct tttacctgga gatatgacta tgaac                          35

<210> SEQ ID NO 30
<211> LENGTH: 36
<212> TYPE: DNA
<213> ORGANISM: Artificial
<220> FEATURE:
<223> OTHER INFORMATION: primer ECcadA-R

<400> SEQUENCE: 30
ggctctagat tattttttgc tttcttcttt caatac                         36

<210> SEQ ID NO 31
<211> LENGTH: 27
<212> TYPE: DNA
<213> ORGANISM: Artificial
<220> FEATURE:
<223> OTHER INFORMATION: primer XhoI-F

<400> SEQUENCE: 31
caattaatgt ctcgagttag ctcactc                                   27

<210> SEQ ID NO 32
<211> LENGTH: 27
<212> TYPE: DNA
<213> ORGANISM: Artificial
<220> FEATURE:
<223> OTHER INFORMATION: primer XhoI-R

<400> SEQUENCE: 32
gagtgagcta actcgagaca ttaattg                                   27

<210> SEQ ID NO 33
<211> LENGTH: 29
<212> TYPE: DNA
<213> ORGANISM: Artificial
<220> FEATURE:
<223> OTHER INFORMATION: primer Pbad-F

<400> SEQUENCE: 33
```
ggcctcgagt tatgacaact tgacggcta                                      29

<210> SEQ ID NO 34
<211> LENGTH: 33
<212> TYPE: DNA
<213> ORGANISM: Artificial
<220> FEATURE:
<223> OTHER INFORMATION: primer Pbad-R

<400> SEQUENCE: 34
ggcgagctca cagtagagag ttgcgataaa aag                                 33

<210> SEQ ID NO 35
<211> LENGTH: 29
<212> TYPE: DNA
<213> ORGANISM: Artificial
<220> FEATURE:
<223> OTHER INFORMATION: primer Ptac-F

<400> SEQUENCE: 35
ggcctcgagg cgcctgatgc ggtattttc                                      29

<210> SEQ ID NO 36
<211> LENGTH: 36
<212> TYPE: DNA
<213> ORGANISM: Artificial
<220> FEATURE:
<223> OTHER INFORMATION: primer Ptac-R

<400> SEQUENCE: 36
ggcgagctcc attatacgag ccgatgatta attgtc                              36

<210> SEQ ID NO 37
<211> LENGTH: 41
<212> TYPE: DNA
<213> ORGANISM: Artificial
<220> FEATURE:
<223> OTHER INFORMATION: primer RBS-F
<220> FEATURE:
<221> NAME/KEY: misc_feature
<222> LOCATION: (9)..(14)
<223> OTHER INFORMATION: n is a, c, g, or t

<400> SEQUENCE: 37
ttttacctnn nnnnatgact atgaatgtta ttgcgattat g                        41

<210> SEQ ID NO 38
<211> LENGTH: 24
<212> TYPE: DNA
<213> ORGANISM: Artificial
<220> FEATURE:
<223> OTHER INFORMATION: primer RBS-R

<400> SEQUENCE: 38
gttcataatc gcaataacat tcat                                           24

<210> SEQ ID NO 39
<211> LENGTH: 36
<212> TYPE: DNA
<213> ORGANISM: Artificial
<220> FEATURE:
<223> OTHER INFORMATION: primer epPCR-F

<400> SEQUENCE: 39
ggcgagctct tttaccttgg aggatgacta tgaatg                              36

```
<210> SEQ ID NO 40
<211> LENGTH: 33
<212> TYPE: DNA
<213> ORGANISM: Artificial
<220> FEATURE:
<223> OTHER INFORMATION: primer epPCR-R

<400> SEQUENCE: 40
ggctctagat tatttgttgt tctcttcctt gag                           33

<210> SEQ ID NO 41
<211> LENGTH: 20
<212> TYPE: DNA
<213> ORGANISM: Artificial
<220> FEATURE:
<223> OTHER INFORMATION: primer RBS-out-F

<400> SEQUENCE: 41
ggctgtgcag gtcgtaaatc                                          20

<210> SEQ ID NO 42
<211> LENGTH: 20
<212> TYPE: DNA
<213> ORGANISM: Artificial
<220> FEATURE:
<223> OTHER INFORMATION: primer ldc-out-F

<400> SEQUENCE: 42
ttgacaatta atcatcggct                                          20

<210> SEQ ID NO 43
<211> LENGTH: 20
<212> TYPE: DNA
<213> ORGANISM: Artificial
<220> FEATURE:
<223> OTHER INFORMATION: primer ldc-out-R

<400> SEQUENCE: 43
gttgtaaaac gacggccagt                                          20
```

EXPRESSION OF *KLEBSIELLA OXYTOCA* POLYPEPTIDES INVOLVED IN LYSINE DECARBOXYLATION, AND METHODS AND APPLICATIONS THEREOF

CROSS-REFERENCE TO RELATED APPLICATIONS

The present application is division of U.S. patent application Ser. No. 15/547,323, filed on 28 Jul. 2017 as a national stage filing under 35 U.S.C. § 371 of PCT/CN2015/071978, filed on 30 Jan. 2015. Each application is incorporated herein by reference in its entirety.

BACKGROUND

Cadaverine is a platform chemical involved in the production of various products. Cadaverine can be synthesized via decarboxylation of lysine in microorganisms. Lysine decarboxylases are the enzymes that catalyze production of cadaverine by removing the carboxyl group from lysine. For example, in *Escherichia coli* (*E. coli*), cadaverine is biosynthesized directly from L-lysine by two lysine decarboxylase polypeptides, CadA and LdcC. Current approaches to improve lysine production and the production of lysine-derived products, such as cadaverine, focus on the overexpression or attenuation of proteins involved in cellular metabolism. However, the yield obtained so far is not satisfying. Therefore, there is a need for new techniques resulting in higher yields of cadaverine.

SUMMARY

One aspect provided herein relates to a lysine decarboxylase polypeptide comprising, consisting of, or consisting essentially of an amino acid sequence selected from the group consisting of mutants of SEQ ID NO: 2 (i.e., mutants of *Klebsiella oxytoca* (*K. oxytoca*) Ldc) and fragments thereof, and fragments of SEQ ID NO: 2 (i.e., fragments of *K. oxytoca* Ldc), wherein the mutants or fragments have at least 95% sequence identity with SEQ ID NO: 2. In certain embodiments, the mutant of SEQ ID NO: 2 (i.e., mutant of *K. oxytoca* Ldc) may comprise, consist of, or consist essentially of the amino acid sequence of SEQ ID NO: 2 or a fragment thereof comprising one or more mutations selected from the group consisting of a mutation at amino acid position 287 to $X_1$, a mutation at amino acid position 398 to $X_2$, a mutation at amino acid position 436 to $X_3$, a mutation at amino acid position 507 to $X_4$, and a mutation at amino acid position 607 to $X_5$; $X_1$, $X_2$, $X_3$, $X_4$, and $X_5$ are each independently selected from the group consisting of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine; and with the proviso that $X_1$ is not lysine, $X_2$ is not threonine, $X_3$ is not arginine, $X_4$ is not phenylalanine, and $X_5$ is not phenylalanine. In certain embodiments, the mutant of SEQ ID NO: 2 (i.e., mutant of *K. oxytoca* Ldc) may comprise, consist of, or consist essentially of an amino acid sequence selected from the group consisting of SEQ ID NO: 5 (i.e., *K. oxytoca* Ldc K287E), SEQ ID NO: 7 (i.e., *K. oxytoca* Ldc T398S), SEQ ID NO: 9 (i.e., *K. oxytoca* Ldc R436G), SEQ ID NO: 11 (i.e., *K. oxytoca* Ldc F507L), and SEQ ID NO: 13 (i.e., *K. oxytoca* Ldc F607Y).

Another aspect provided herein relates to a non-naturally occurring DNA polynucleotide comprising, consisting of, or consisting essentially of one or more lysine decarboxylase nucleotide sequences, wherein the lysine decarboxylase nucleotide sequences have at least 95% sequence identity with SEQ ID NO: 1 or SEQ ID NO: 3, and wherein the polynucleotide encodes one or more lysine decarboxylase polypeptides described herein. In certain embodiments, the non-naturally occurring DNA polynucleotide may comprise one or more lysine decarboxylase nucleotide sequences selected from the group consisting of mutants of SEQ ID NO: 1 (i.e., mutants of *K. oxytoca* ldc) and fragments thereof, and fragments of SEQ ID NO: 1 (i.e., fragments of *K. oxytoca* ldc), wherein the lysine decarboxylase nucleotide sequences have at least 95% sequence identity with SEQ ID NO: 1 or SEQ ID NO: 3, and wherein the polynucleotide encodes one or more lysine decarboxylase polypeptides comprising, consisting of, or consisting essentially of an amino acid sequence selected from the group consisting of SEQ ID NO: 2 (i.e., *K. oxytoca* Ldc) and fragments thereof, and mutants of SEQ ID NO: 2 (i.e., mutants of *K. oxytoca* Ldc) and fragments thereof. In certain embodiments, the mutant of SEQ ID NO: 1 (i.e., mutant of *K. oxytoca* ldc) may comprise, consist of, or consist essentially of the lysine decarboxylase nucleotide sequence of SEQ ID NO: 3 (i.e., *K. oxytoca* ldc-co1) or a fragment thereof. In certain embodiments, the lysine decarboxylase nucleotide sequence of SEQ ID NO: 3 comprises one or more mutations selected from the group consisting of a mutation at nucleotide position 859 to $Z_1$, a mutation at nucleotide position 1193 to $Z_2$, a mutation at nucleotide position 1306 to $Z_3$, a mutation at nucleotide position 1521 to $Z_4$, and a mutation at nucleotide position 1820 to $Z_5$; $Z_1$, $Z_2$, $Z_3$, $Z_4$, and $Z_5$ are each independently selected from the group consisting of adenine (A), guanine (G), cytosine (C), and thymine (T), with the proviso that $Z_1$ is not an A, $Z_2$ is not a C, $Z_3$ is not a C, $Z_4$ is not a C or T, and $Z_5$ is not a T. In certain embodiments, the mutant of SEQ ID NO: 1 (i.e., mutant of *K. oxytoca* ldc) comprises, consists of, or consists essentially of a lysine decarboxylase nucleotide sequence selected from the group consisting of SEQ ID NO: 4 (i.e., *K. oxytoca* ldc-co1 A859G), SEQ ID NO: 6 (i.e., *K. oxytoca* ldc-co1 C1193G), SEQ ID NO: 8 (i.e., *K. oxytoca* ldc-co1 C1306G), SEQ ID NO: 10 (i.e., *K. oxytoca* ldc-co1 C1521G), and SEQ ID NO: 12 (i.e., *K. oxytoca* ldc-co1 T1820A).

Another aspect provided herein relates to an expression plasmid vector comprising a DNA polynucleotide as described herein, and a backbone plasmid capable of autonomous replication in a host cell, wherein the expression plasmid vector is used for production of a lysine-derived product.

Another aspect provided herein relates to a transformant comprising one or more expression plasmid vectors as described herein in a host cell.

Another aspect provided herein relates to a mutant host cell comprising a DNA polynucleotide as described herein integrated into a chromosome of the host cell.

Another aspect provided herein relates to a method for producing one or more lysine decarboxylase polypeptides as described herein, wherein the method comprises obtaining the mutant host cell described herein and/or the transformant described herein, culturing the mutant host cell and/or transformant under conditions effective for the expression of the one or more polypeptides, and harvesting the one or more lysine decarboxylase polypeptides.

Another aspect provided herein relates to a method for producing cadaverine (1,5-pentanediamine) comprising 1a) cultivating a mutant host cell and/or a transformant described herein; 1b) producing cadaverine using the culture obtained from step 1a to decarboxylate lysine; and 1c) extracting and purifying cadaverine using the culture obtained from step 1b.

Another aspect provided herein relates to a method for producing cadaverine (1,5-pentanediamine) comprising obtaining one or more lysine decarboxylase polypeptides as described herein and producing cadaverine using the one or more lysine decarboxylase polypeptides to decarboxylate lysine.

BRIEF DESCRIPTION OF THE DRAWINGS

FIG. 1: Table showing primers (SEQ ID NOs: 27-43) used in creating the constructs described in the Examples section below.

FIG. 2: Table showing strains, plasmids, enzymes, genes, promoters, and ribosomal binding site (RBS) deoxyribonucleic acid (DNA) sequences described herein.

DETAILED DESCRIPTION

Figure 3:
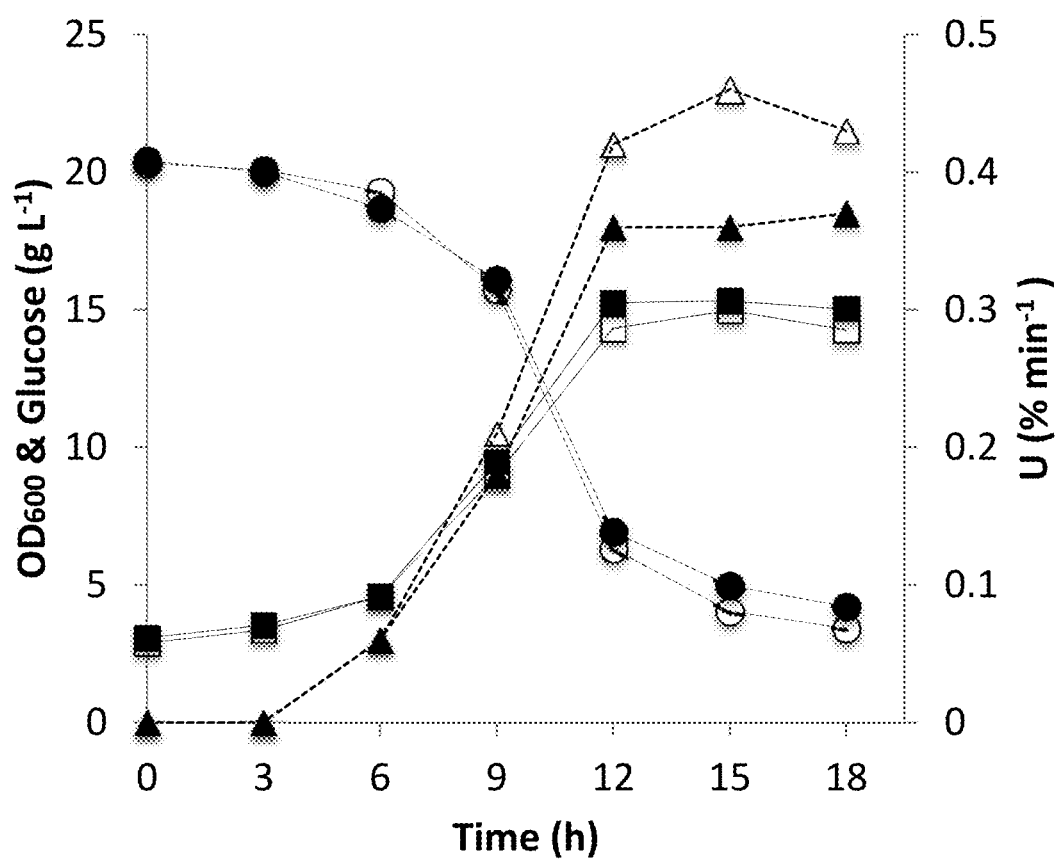
FIG. 3: Batch fermentation results. Strains LN20 (white) and CIB60 (black) were grown using batch fermentation, and the cultures were assayed for their ability to convert lysine-HCl to cadaverine. At each time point, samples were taken to measure $OD_{600}$ (square), glucose (circle), and activity (triangle).

The following description provides specific details for a thorough understanding of, and enabling description for, embodiments of the disclosure. However, one skilled in the art will understand that the disclosure may be practiced without these details. In other instances, well-known structures and functions have not been shown or described in detail to avoid unnecessarily obscuring the description of the embodiments of the disclosure.

*Klebsiella oxytoca* (*K. oxytoca*) is a Gram-negative, rod-shaped bacterium. The *K. oxytoca* E718 genome sequence contains the *K. oxytoca* lysine decarboxylase gene, ldc, which encodes the lysine decarboxylase polypeptide, *K. oxytoca* Ldc. As used herein, the nucleotide sequence of *K. oxytoca* ldc is referred to as "*K. oxytoca* ldc," "ldc," "*K. oxytoca* ldc polynucleotide," or "*K. oxytoca* ldc nucleotide sequence" and has the nucleotide sequence of SEQ ID NO: 1. As used herein, the *K. oxytoca* Ldc polypeptide is referred to as "*K. oxytoca* Ldc," "Ldc," "*K. oxytoca* Ldc polypeptide," or "*K. oxytoca* Ldc protein" and has the amino acid sequence of SEQ ID NO: 2.

One aspect provided herein relates to a lysine decarboxylase polypeptide comprising, consisting of, or consisting essentially of an amino acid sequence selected from the group consisting of SEQ ID NO: 2 (i.e., *K. oxytoca* Ldc) and fragments thereof, and mutants of SEQ ID NO: 2 (i.e., mutants of *K. oxytoca* Ldc) and fragments thereof, wherein the mutants or fragments have at least 95% sequence identity with SEQ ID NO: 2.

In certain embodiments, the mutants of SEQ ID NO: 2 (i.e., mutants of *K. oxytoca* Ldc) or fragments thereof may have at least about 90%, at least about 91%, at least about 92%, at least about 93%, at least about 94%, at least about 95%, at least about 96%, at least about 97%, at least about 98%, at least about 99%, about 90%~99.999%, about 91%~99.999%, about 92%~99.999%, about 93%~99.999%, about 94%~99.999%, about 95%~99.999%, about 96%~99.999%, about 97%~99.999%, about 98%~99.999%, or about 99%~99.999% sequence identity with SEQ ID NO: 2.

The term "about" as used herein means within 5% or 10% of a stated value or a range of values.

In certain embodiments, the mutants of SEQ ID NO: 2 (i.e., mutants of *K. oxytoca* Ldc) may comprise, consist of, or consist essentially of the amino acid sequence of SEQ ID NO: 2 comprising one or more mutations. A mutant of SEQ ID NO: 2 (i.e., mutant of *K. oxytoca* Ldc) may comprise one or more deletions, substitutions, additions, and/or insertions of one or more amino acids within SEQ ID NO: 2, wherein the mutant of SEQ ID NO: 2 (i.e., mutant of *K. oxytoca* Ldc) provides substantially the same lysine decarboxylase activity as *K. oxytoca* Ldc (i.e., the mutant of *K. oxytoca* Ldc has about 80% or higher lysine decarboxylase activity compared to that of *K. oxytoca* Ldc; about 90% or higher lysine decarboxylase activity compared to that of *K. oxytoca* Ldc; about 95% or higher lysine decarboxylase activity compared to that of *K. oxytoca* Ldc; about 97% or higher lysine decarboxylase activity compared to that of *K. oxytoca* Ldc; about 99% or higher lysine decarboxylase activity compared to that of *K. oxytoca* Ldc; or about 100% or higher lysine decarboxylase activity compared to that of *K. oxytoca* Ldc).

Examples of preferred mutants of SEQ ID NO: 2 (i.e., mutants of *K. oxytoca* Ldc) include, without limitation, SEQ ID NO: 5 (i.e., *K. oxytoca* Ldc K287E); SEQ ID NO: 7 (i.e., *K. oxytoca* Ldc T398S); SEQ ID NO: 9 (i.e., *K. oxytoca* Ldc R436G); SEQ ID NO: 11 (i.e., *K. oxytoca* Ldc F507L); and SEQ ID NO: 13 (i.e., *K. oxytoca* Ldc F607Y). Additional examples of mutants of SEQ ID NO: 2 (i.e., mutants of *K. oxytoca* Ldc) include, without limitation, mutants comprising, consisting of, or consisting essentially of the amino acid sequence of SEQ ID NO: 2 comprising one or more mutations selected from the group consisting of a mutation at amino acid position 287 to $X_1$, a mutation at amino acid position 398 to $X_2$, a mutation at amino acid position 436 to $X_3$, a mutation at amino acid position 507 to $X_4$, a mutation at amino acid position 607 to $X_5$; homologous polypeptides of SEQ ID NO: 5 (e.g., *K. oxytoca* Ldc K287$X_1$); homologous polypeptides of SEQ ID NO: 7 (e.g., *K. oxytoca* Ldc T398$X_2$); homologous polypeptides of SEQ ID NO: 9 (e.g., *K. oxytoca* Ldc R436$X_3$); homologous polypeptides of SEQ ID NO: 11 (e.g., *K. oxytoca* Ldc F507$X_4$); and homologous polypeptides of SEQ ID NO: 13 (e.g., *K. oxytoca* Ldc F607$X_5$). $X_1$, $X_2$, $X_3$, $X_4$, and $X_5$ are each independently selected from the group consisting of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine, with the proviso that $X_1$ is not lysine, $X_2$ is not threonine, $X_3$ is not arginine, $X_4$ is not phenylalanine, and $X_5$ is not phenylalanine. As used herein, a homologous polypeptide may have at least about 90%, at least about 91%, at least about 92%, at least about 93%, at least about 94%, at least about 95%, at least about 96%, at least about 97%, at least about 98%, at least about 99%, about 90%~99.999%, about 91%~99.999%, about 92%~99.999%, about 93%~99.999%, about 94%~99.999%, about 95%~99.999%, about 96%~99.999%, about 97%~99.999%, about 98%~99.999%, or about 99%~99.999% sequence homology to a specified polypeptide sequence.

In certain embodiments, a fragment of a polypeptide as used herein provides substantially the same function as the whole unmutated polypeptide from which the fragment is derived. In these embodiments, fragments of K. oxytoca Ldc or mutants of K. oxytoca Ldc possess substantially the same function as K. oxytoca Ldc or the mutant of K. oxytoca from which they are derived (e.g., lysine decarboxylase activity).

Another aspect provided herein relates to a DNA polynucleotide comprising, consisting of, or consisting essentially of one or more lysine decarboxylase nucleotide sequences described herein. In certain embodiments, a DNA polynucleotide may comprise one or more lysine decarboxylase nucleotide sequences selected from the group consisting of SEQ ID NO: 1 (i.e., K. oxytoca ldc) and fragments thereof, and mutants of SEQ ID NO: 1 (i.e., mutants of K. oxytoca ldc) and fragments thereof, wherein the lysine decarboxylase nucleotide sequences have at least 95% sequence identity with SEQ ID NO: 1 or SEQ ID NO: 3, and wherein the polynucleotide encodes one or more lysine decarboxylase polypeptides comprising, consisting of, or consisting essentially of an amino acid sequence selected from the group consisting of SEQ ID NO: 2 (i.e., K. oxytoca Ldc) and fragments thereof, and mutants of SEQ ID NO: 2 (i.e., mutants of K. oxytoca Ldc) and fragments thereof.

In certain embodiments, the lysine decarboxylase polypeptides, K. oxytoca Ldc and mutants of K. oxytoca Ldc are the same as described supra. When there are a plurality of polypeptides, each polypeptide may be the same or different, and the one or more polypeptides may be expressed individually or as a fusion protein.

Examples of preferred mutants of SEQ ID NO: 2 (i.e., mutants of K. oxytoca Ldc) include, without limitation, SEQ ID NO: 5 (i.e., K. oxytoca Ldc K287E); SEQ ID NO: 7 (i.e., K. oxytoca Ldc T398S); SEQ ID NO: 9 (i.e., K. oxytoca Ldc R436G); SEQ ID NO: 11 (i.e., K. oxytoca Ldc F507L); and SEQ ID NO: 13 (i.e., K. oxytoca Ldc F607Y). Additional examples of mutants of SEQ ID NO: 2 (i.e., mutants of K. oxytoca Ldc) include, without limitation, mutants comprising, consisting of, or consisting essentially of the amino acid sequence of SEQ ID NO: 2 comprising one or more mutations selected from the group consisting of a mutation at amino acid position 287 to $X_1$, a mutation at amino acid position 398 to $X_2$, a mutation at amino acid position 436 to $X_3$, a mutation at amino acid position 507 to $X_4$, a mutation at amino acid position 607 to $X_5$; homologous polypeptides of SEQ ID NO: 5 (e.g., K. oxytoca Ldc K287$X_1$); homologous polypeptides of SEQ ID NO: 7 (e.g., K. oxytoca Ldc T398$X_2$); homologous polypeptides of SEQ ID NO: 9 (e.g., K. oxytoca Ldc R436$X_3$); homologous polypeptides of SEQ ID NO: 11 (e.g., K. oxytoca Ldc F507$X_4$); and homologous polypeptides of SEQ ID NO: 13 (e.g., K. oxytoca Ldc F607$X_5$). $X_1$, $X_2$, $X_3$, $X_4$, and $X_5$ are each independently selected from the group consisting of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine, with the proviso that $X_1$ is not lysine, $X_2$ is not threonine, $X_3$ is not arginine, $X_4$ is not phenylalanine, and $X_5$ is not phenylalanine.

In certain embodiments, the DNA polynucleotide sequence may comprise one or more lysine decarboxylase nucleotide sequences selected from the group consisting of mutants of SEQ ID NO: 1 (i.e., mutants of K. oxytoca ldc) and fragments thereof, and fragments of SEQ ID NO: 1 (i.e., fragments of K. oxytoca ldc). A mutant of SEQ ID NO: 1 (i.e., mutant of K. oxytoca ldc) may include one or more deletions, substitutions, additions, and/or insertions of one or more nucleotides to the nucleotide sequence comprising SEQ ID NO: 1 or SEQ ID NO 3, while the lysine decarboxylase polypeptide encoded by the nucleotide sequence provides substantially the same function as K. oxytoca Ldc (i.e., the lysine decarboxylase polypeptide encoded by the mutant of K. oxytoca ldc has about 80% or higher lysine decarboxylase activity compared to that of K. oxytoca Ldc; about 90% or higher lysine decarboxylase activity compared to that of K. oxytoca Ldc; about 95% or higher lysine decarboxylase activity compared to that of K. oxytoca Ldc; about 97% or higher lysine decarboxylase activity compared to that of K. oxytoca Ldc; about 99% or higher lysine decarboxylase activity compared to that of K. oxytoca Ldc; or about 100% or higher lysine decarboxylase activity compared to that of K. oxytoca Ldc).

In certain embodiments, the mutants of SEQ ID NO: 1 (i.e., mutants of K. oxytoca ldc) or fragments thereof may have at least about 90%, at least about 91%, at least about 92%, at least about 93%, at least about 94%, at least about 95%, at least about 96%, at least about 97%, at least about 98%, at least about 99%, about 90%~99.999%, about 91%~99.999%, about 92%~99.999%, about 93%~99.999%, about 94%~99.999%, about 95%~99.999%, about 96%~99.999%, about 97%~99.999%, about 98%~99.999%, or about 99%~99.999% sequence identity with SEQ ID NO: 1 or SEQ ID NO: 3.

An example of a mutant of SEQ ID NO: 1 (i.e., mutant of K. oxytoca ldc) may include, without limitation, the nucleotide sequence of SEQ ID NO: 1 (i.e., K. oxytoca ldc) that has been codon-optimized for expression in E. coli (i.e., K. oxytoca ldc-co1, SEQ ID NO: 3) and that encodes the amino acid sequence of SEQ ID NO: 2 (i.e., K. oxytoca Ldc). Other examples of mutants of SEQ ID NO: 1 (i.e., mutants of K. oxytoca ldc) may include, without limitation, lysine decarboxylase nucleotide sequences that encode amino acid sequences of mutants of SEQ ID NO: 2 (i.e., mutants of K. oxytoca Ldc). Examples of preferred mutants of SEQ ID NO: 1 (i.e., mutants of K. oxytoca ldc) that encode an amino acid sequence of mutants of SEQ ID NO: 2 (i.e., mutants of K. oxytoca Ldc) include, without limitation, SEQ ID NO: 4 (i.e., K. oxytoca ldc-co1 A859G), SEQ ID NO: 6 (i.e., K. oxytoca ldc-co1 C1193G), SEQ ID NO: 8 (i.e., K. oxytoca ldc-co1 C1306G), SEQ ID NO: 10 (i.e., K. oxytoca ldc-co1 C1521G), and SEQ ID NO: 12 (i.e., K. oxytoca ldc-co1 T1820A).

Additional examples of mutants of SEQ ID NO: 1 (i.e., mutants of K. oxytoca ldc) that encode an amino acid sequence of mutants of SEQ ID NO: 2 (i.e., mutants of K. oxytoca Ldc) may include, without limitation, lysine decarboxylase nucleotide sequences comprising, consisting of, or consisting essentially of SEQ ID NO: 1 or SEQ ID NO: 3 comprising one or more mutations selected from the group consisting of a mutation at nucleotide position 859 to $Z_1$, a mutation at nucleotide position 1193 to $Z_2$, a mutation at nucleotide position 1306 to $Z_3$, a mutation at nucleotide position 1521 to $Z_4$, a mutation at nucleotide position 1820 to $Z_5$, and/or any combination thereof; lysine decarboxylase nucleotide sequences comprising, consisting of, or consisting essentially of SEQ ID NO: 1 or SEQ ID NO: 3 comprising one or more mutations selected from the group consisting of a mutation at nucleotide position 859 mutated to a G (guanine), a mutation at nucleotide position 1193 mutated to a G, a mutation at nucleotide position 1306 mutated to a G, a mutation at nucleotide position 1521 mutated to a G or an A (adenine), a mutation at nucleotide position 1820 mutated to an A, and/or any combination thereof; homologous nucleotide sequences of *K. oxytoca* ldc A859G or *K. oxytoca* ldc-co1 A859G (e.g., *K. oxytoca* ldc A859$Z_1$ or *K. oxytoca* ldc-co1 A859$Z_1$); homologous nucleotide sequences of *K. oxytoca* ldc C1193G or *K. oxytoca* ldc-co1 C1193G (e.g., *K. oxytoca* ldc C1193$Z_2$ or *K. oxytoca* ldc-co1 C1193$Z_2$); homologous nucleotide sequences of *K. oxytoca* ldc C1306G or *K. oxytoca* ldc-co1 C1306G (e.g., *K. oxytoca* ldc C1306$Z_3$ or *K. oxytoca* ldc-co1 C1306$Z_3$); homologous nucleotide sequences of *K. oxytoca* ldc C1521G or *K. oxytoca* ldc-co1 C1521G (e.g., *K. oxytoca* ldc C1521$Z_4$ or *K. oxytoca* ldc-co1 C1521$Z_4$); and homologous nucleotide sequences of *K. oxytoca* ldc T1820A or *K. oxytoca* ldc-co1 T1820A (e.g., *K. oxytoca* ldc T1820$Z_5$ or *K. oxytoca* ldc-co1 T1820$Z_5$). $Z_1$, $Z_2$, $Z_3$, $Z_4$, and $Z_5$ are each independently selected from the group consisting of A, G, C (cytosine), and T (thymine), with the proviso that $Z_1$ is not an A, $Z_2$ is not a C, $Z_3$ is not a C, $Z_4$ is not a C or T, and $Z_5$ is not a T. As used herein, a homologous nucleotide sequence may have at least about 90%, at least about 91%, at least about 92%, at least about 93%, at least about 94%, at least about 95%, at least about 96%, at least about 97%, at least about 98%, at least about 99%, about 90%~99.999%, about 91%~99.999%, about 92%~99.999%, about 93%~99.999%, about 94%~99.999%, about 95%~99.999%, about 96%~99.999%, about 97%~99.999%, about 98%~99.999%, or about 99%~99.999% homology to a specified nucleotide sequence.

In certain embodiments, the DNA polynucleotide may be a recombinant or no-naturally occurring polynucleotide. In certain embodiments, the DNA polynucleotide may be cDNA. In certain embodiments, the DNA polynucleotide may be obtained by codon optimization for optimal polypeptide expression in a particular microorganism (e.g., *E. coli*, *H. alvei*, or *K. oxytoca*).

Nucleotide sequences, polynucleotides, and DNA molecules as used herein are not limited to the functional region, and may include at least one of an expression suppression region, a coding region, a leader sequence, an exon, an intron, and an expression cassette (see, e.g. Papadakis et al., "Promoters and Control Elements: Designing Expression Cassettes for Gene Therapy," Current Gene Therapy (2004), 4, 89-113). Further, nucleotide sequences or polynucleotides may include double stranded DNA or single stranded DNA (i.e., a sense chain and an antisense chain constituting the double strand DNA), or ribonucleic acid (RNA). A polynucleotide containing nucleotide sequences may include fragments, and/or mutants of the nucleotide sequences. A fragment of a nucleotide sequence means a part of the nucleotide sequence that encodes a polypeptide which provides substantially the same function as the polypeptide encoded by the whole polynucleotide. Examples of mutants of a nucleotide sequence include naturally occurring allelic mutants; artificial mutants; and nucleotide sequences obtained by deletion, substitution, addition, and/or insertion of one or more nucleotides to the nucleotide sequence. It should be understood that such fragments, and/or mutants of a nucleotide sequence encode a polypeptide having substantially the same function as the polypeptide encoded by the original nucleotide sequence. For example, a fragment and/or mutant of *K. oxytoca* ldc encodes a polypeptide that possesses substantially the same function of *K. oxytoca* Ldc (i.e., lysine decarboxylase activity).

Codon optimization is a technique that may be used to maximize the protein expression in an organism by increasing the translational efficiency of the gene of interest. Different organisms often show particular preferences for one of the several codons that encode the same amino acid due to mutational biases and natural selection. For example, in fast growing microorganisms such as *E. coli*, optimal codons reflect the composition of their respective genomic tRNA pool. Therefore, the codons of low frequency of an amino acid may be replaced with codons for the same amino acid but of high frequency in the fast growing microorganism. Accordingly, the expression of the optimized DNA sequence is improved in the fast growing microorganism. See, e.g. www.guptalab.org/shubhg/pdf/shubhra_codon.pdf for an overview of codon optimization technology, which is incorporated herein by reference in its entirety. As provided herein, polynucleotide sequences may be codon optimized for optimal polypeptide expression in a particular microorganism including, but not limited to, *E. coli*, *H. alvei*, and *K. oxytoca*.

In certain embodiments, mutants of a nucleotide sequence can be obtained from codon optimization of the nucleotide sequence to decrease the G and C nucleotide content thereof for improved protein expression. A genome is considered GC-rich if about 50% or more of its bases are G or C. A high GC content in the nucleotide sequence of interest may lead to the formation of secondary structure in the mRNA, which can result in interrupted translation and lower levels of expression. Thus, changing G and C residues in the coding sequence to A and T residues without changing the amino acids may provide higher expression levels.

In certain embodiments, the DNA polynucleotide described herein may further comprise one or more ribosomal binding site (RBS) DNA nucleotide sequences. As used herein, the RBS DNA nucleotide sequence may be referred to as "RBS DNA," "RBS DNA sequence," "RBS DNA nucleotide sequence," or "RBS DNA polynucleotide sequence." An RBS is an RNA sequence found in messenger RNA (mRNA) to which ribosomes can bind and initiate translation. In prokaryotes, the RBS is called the Shine-Dalgarno sequence and lies upstream from the start codon of the RNA sequence to be translated. Mutations in the RBS sequence can reduce or increase translation in prokaryotes. The RBS DNA nucleotide sequences provided herein have the same base sequence of the RBS sequences except for uracil (U) in the RNA sequence of the RBS sequence is replaced by thymine (T). For example, if the RBS sequence is "GGAGAU", the corresponding RBS DNA nucleotide sequence is "GGAGAT." As shown in the Examples below, expression of *K. oxytoca* Ldc and mutants thereof from various RBS sequences resulted in different levels of cadaverine production activity (see Example 7). As provided below in Example 7, the plasmid pUC18-KOldc-co1-Pbad contains the RBS DNA nucleotide sequence "GGAGAT" (RBS DNA-1, SEQ ID NO: 14) upstream of the *K. oxytoca* ldc-co1 sequence. An RBS DNA library was prepared to use for screening for an optimal RBS sequence for *K. oxytoca* Ldc protein expression that results in increased cadaverine production. At least five plasmids with mutated RBS DNA nucleotide sequences produced higher levels of cadaverine when transformed into *E. coli* K12 compared to the plasmid containing the RBS DNA nucleotide sequence, RBS DNA-1 (SEQ ID NO: 14). The plasmid (pLN637) that contains the RBS DNA nucleotide sequence, "TGGAGG" (RBS DNA-5, SEQ ID NO: 18), produced the highest yield of cadaverine (see Example 7).

As provided herein in certain embodiments, the DNA polynucleotide described herein may further comprise one or more RBS DNA nucleotide sequences selected from the group consisting of SEQ ID NO: 14 (i.e., RBS DNA-1), SEQ ID NO: 15 (i.e., RBS DNA-2), SEQ ID NO: 16 (i.e., RBS DNA-3), SEQ ID NO: 17 (i.e., RBS DNA-4), SEQ ID NO: 18 (i.e., RBS DNA-5), and SEQ ID NO: 19 (i.e., RBS DNA-6). In certain preferred embodiments, the one or more RBS DNA nucleotide sequences may comprise, consist of, or consist essentially of SEQ ID NO: 18 (i.e., RBS DNA-5). In certain embodiments, the RBS DNA nucleotide sequence may be positioned upstream of the lysine decarboxylase nucleotide sequence of SEQ ID NO: 1 (i.e., *K. oxytoca* ldc) and fragments thereof, and mutants of SEQ ID NO: 1 (i.e., *K. oxytoca* ldc) and fragments thereof.

As provided herein in certain embodiments, the DNA polynucleotide described herein may further comprise one or more promoter nucleotide sequences selected from the group consisting of SEQ ID NO: 20 (i.e., Plac promoter sequence), SEQ ID NO: 21 (i.e., Pbad promoter sequence), and SEQ ID NO: 22 (i.e., Ptac promoter sequence). A promoter is a region of DNA that initiates transcription of DNA. The promoter is located upstream of the DNA to be transcribed. In certain preferred embodiments, the one or more promoter nucleotide sequences may comprise, consist of, or consist essentially of SEQ ID NO: 21 (i.e., Pbad promoter sequence). In certain embodiments, the promoter nucleotide sequence may be positioned upstream of the lysine decarboxylase nucleotide sequence of SEQ ID NO: 1 (i.e., *K. oxytoca* ldc) or fragments thereof and mutants of SEQ ID NO: 1 (i.e., *K. oxytoca* ldc) or fragments thereof. When the DNA polynucleotide comprises one or more RBS DNA nucleotide sequences and one or more promoter nucleotide sequences, the one or more promoter nucleotide sequences may be positioned upstream of the lysine decarboxylase nucleotide sequence and the RBS DNA nucleotide sequence.

Another aspect provided herein relates to an expression plasmid vector comprising, consisting of, or consisting essentially of:

a DNA polynucleotide comprising, consisting of, or consisting essentially of one or more lysine decarboxylase nucleotide sequences selected from the group consisting of mutants of SEQ ID NO: 1 (i.e., mutants of *K. oxytoca* ldc) and fragments thereof, and fragments of SEQ ID NO: 1 (i.e., fragments of *K. oxytoca* ldc), wherein the lysine decarboxylase nucleotide sequences have at least 95% sequence identity with SEQ ID NO: 1 or SEQ ID NO: 3, and wherein the polynucleotide encodes one or more lysine decarboxylase polypeptides comprising, consisting of, or consisting essentially of an amino acid sequence selected from the group consisting of SEQ ID NO: 2 (i.e., *K. oxytoca* Ldc) and fragments thereof, and mutants of SEQ ID NO: 2 (i.e., mutants of *K. oxytoca* Ldc) and fragments thereof; and a backbone plasmid capable of autonomous replication in a host cell,
wherein the expression plasmid vector is used for production of a lysine-derived product.

The DNA polynucleotides; lysine decarboxylase nucleotide sequences; *K. oxytoca* ldc, mutants, and fragments thereof; lysine decarboxylase polypeptides; *K. oxytoca* Ldc, mutants, and fragments thereof are the same as described supra. When there are a plurality of polypeptides, each polypeptide may be the same or different, and the one or more polypeptides may be expressed individually or as a fusion protein.

An example of a mutant of SEQ ID NO: 1 (i.e., mutant of *K. oxytoca* ldc) may include, without limitation, the nucleotide sequence of SEQ ID NO: 1 (i.e., *K. oxytoca* ldc) that has been codon-optimized for expression in *E. coli* (i.e., *K. oxytoca* ldc-co1, SEQ ID NO: 3) and that encodes the amino acid sequence of SEQ ID NO: 2 (i.e., *K. oxytoca* Ldc). Other examples of mutants of SEQ ID NO: 1 (i.e., mutants of *K. oxytoca* ldc) may include, without limitation, lysine decarboxylase nucleotide sequences that encode amino acid sequences of mutants of SEQ ID NO: 2 (i.e., mutants of *K. oxytoca* Ldc). Examples of preferred mutants of SEQ ID NO: 1 (i.e., mutants of *K. oxytoca* ldc) that encode an amino acid sequence of mutants of SEQ ID NO: 2 (i.e., mutants of *K. oxytoca* Ldc) include, without limitation, SEQ ID NO: 4 (i.e., *K. oxytoca* ldc-co1 A859G), SEQ ID NO: 6 (i.e., *K. oxytoca* ldc-co1 C1193G), SEQ ID NO: 8 (i.e., *K. oxytoca* ldc-co1 C1306G), SEQ ID NO: 10 (i.e., *K. oxytoca* ldc-co1 C1521G), and SEQ ID NO: 12 (i.e., *K. oxytoca* ldc-co1 T1820A).

Additional examples of mutants of SEQ ID NO: 1 (i.e., mutants of *K. oxytoca* ldc) that encode an amino acid sequence of mutants of SEQ ID NO: 2 (i.e., mutants of *K. oxytoca* Ldc) may include, without limitation, lysine decarboxylase nucleotide sequences comprising, consisting of, or consisting essentially of SEQ ID NO: 1 or SEQ ID NO: 3 comprising one or more mutations selected from the group consisting of a mutation at nucleotide position 859 to $Z_1$, a mutation at nucleotide position 1193 to $Z_2$, a mutation at nucleotide position 1306 to $Z_3$, a mutation at nucleotide position 1521 to $Z_4$, a mutation at nucleotide position 1820 to $Z_5$, and/or any combination thereof; lysine decarboxylase nucleotide sequences comprising, consisting of, or consisting essentially of SEQ ID NO: 1 or SEQ ID NO: 3 comprising one or more mutations selected from the group consisting of a mutation at nucleotide position 859 mutated to a G (guanine), a mutation at nucleotide position 1193 mutated to a G, a mutation at nucleotide position 1306 mutated to a G, a mutation at nucleotide position 1521 mutated to a G or an A (adenine), a mutation at nucleotide position 1820 mutated to an A, and/or any combination thereof; homologous nucleotide sequences of *K. oxytoca* ldc A859G or *K. oxytoca* ldc-co-1 A859G (e.g., *K. oxytoca* ldc A859$Z_1$ or *K. oxytoca* ldc-co1 A859$Z_1$); homologous nucleotide sequences of *K. oxytoca* ldc C1193G or *K. oxytoca* ldc-co1 C1193G (e.g., *K. oxytoca* ldc C1193$Z_2$ or *K. oxytoca* ldc-co1 C1193$Z_2$); homologous nucleotide sequences of *K. oxytoca* ldc C1306G or *K. oxytoca* ldc-co1 C1306G (e.g., *K. oxytoca* ldc C1306$Z_3$ or *K. oxytoca* ldc-co1 C1306$Z_3$); homologous nucleotide sequences of *K. oxytoca* ldc C1521G or *K. oxytoca* ldc-co1 C1521G (e.g., *K. oxytoca* ldc C1521$Z_4$ or *K. oxytoca* ldc-co1 C1521$Z_4$); and homologous nucleotide sequences of *K. oxytoca* ldc T1820A or *K. oxytoca* ldc-co1 T1820A (e.g., *K. oxytoca* ldc T1820$Z_5$ or *K. oxytoca* ldc-co1 T1820$Z_5$). $Z_1$, $Z_2$, $Z_3$, $Z_4$, and $Z_5$ are each independently selected from the group consisting of A, G, C (cytosine), and T (thymine), with the proviso that $Z_1$ is not an A, $Z_2$ is not a C, $Z_3$ is not a C, $Z_4$ is not a C or T, and $Z_5$ is not a T.

Examples of preferred mutants of SEQ ID NO: 2 (i.e., mutants of *K. oxytoca* Ldc) include, without limitation, SEQ ID NO: 5 (i.e., *K. oxytoca* Ldc K287E); SEQ ID NO: 7 (i.e., *K. oxytoca* Ldc T398S); SEQ ID NO: 9 (i.e., *K. oxytoca* Ldc R436G); SEQ ID NO: 11 (i.e., *K. oxytoca* Ldc F507L); and SEQ ID NO: 13 (i.e., *K. oxytoca* Ldc F607Y). Additional examples of mutants of SEQ ID NO: 2 (i.e., mutants of *K. oxytoca* Ldc) include, without limitation, mutants comprising, consisting of, or consisting essentially of the amino acid sequence of SEQ ID NO: 2 comprising one or more mutations selected from the group consisting of a mutation at amino acid position 287 to $X_1$, a mutation at amino acid position 398 to $X_2$, a mutation at amino acid position 436 to $X_3$, a mutation at amino acid position 507 to $X_4$, a mutation at amino acid position 607 to $X_5$; homologous polypeptides of SEQ ID NO: 5 (e.g., *K. oxytoca* Ldc K287$X_1$); homologous polypeptides of SEQ ID NO: 7 (e.g., *K. oxytoca* Ldc T398$X_2$); homologous polypeptides of SEQ ID NO: 9 (e.g., *K. oxytoca* Ldc R436$X_3$); homologous polypeptides of SEQ ID NO: 11 (e.g., *K. oxytoca* Ldc F507$X_4$); and homologous polypeptides of SEQ ID NO: 13 (e.g., *K. oxytoca* Ldc F607$X_5$). $X_1$, $X_2$, $X_3$, $X_4$, and $X_5$ are each independently selected from the group consisting of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine, with the proviso that $X_1$ is not lysine, $X_2$ is not threonine, $X_3$ is not arginine, $X_4$ is not phenylalanine, and $X_5$ is not phenylalanine.

As used herein, the term "host cell" refers to a microorganism cell that may be any cell that can be transformed with an expression plasmid vector (e.g., *Escherichia* (e.g., *E. coli*), *Klebsiella* (e.g., *K. oxytoca*), *Pseudomonas* (e.g., *P. aeruginosa*), *Corynebacterium* (e.g., *Corynebacterium glutamicum*), *Bacilli*, *Hafnia* (e.g., *Hafnia alvei*), *Brevibacterium*, *Lactobacillus* (e.g., *Lactobacillus pentosus*, *Lactobacillus plantarum*, *Lactobacillus saerimneri*), *Lactococcus* (e.g., *Lactococcus lactis*, *Lactococcus lactis* ssp. *cremoris*, *Lactococcus lactis* ssp. *lactis*), and *Streptococcus* (e.g., *Streptococcus thermophilus*)).

An *E. coli* cell may be any of the *E. coli* strains derived from *E. coli* K12 (e.g., MG1655, W3110, DH10b, DH1, BW2952 and strains derived therefrom) or *E. coli* B, or strains derived therefrom.

A lysine derived product as used herein may be cadaverine. For example, the expression plasmid vector described herein may be used for production of cadaverine.

In certain embodiments, the host cell may contain one or more endogenous plasmids. In certain embodiments, the host cell does not contain endogenous plasmids. The term "cure" as used herein means to remove one or more endogenous plasmids from a host cell. In certain embodiments, a host cell may be "cured" of all endogenous plasmids by removing all endogenous plasmids from the host cell. In certain embodiments, a host cell may be "cured" of one or more endogenous plasmids by removing only the one or more endogenous plasmids that is targeted for removal from the cell.

In certain embodiments, the host cell may be a prokaryotic cell (e.g. is, *H. alvei*) containing endogenous plasmids that encode specific toxin/antitoxin gene pairs. Such toxin/antitoxin gene pairs play a role in maintenance of the genetic information and response to stress. (See, Wertz et al. "Chimeric nature of two plasmids of *Hafnia alvei* encoding the bacteriocins alveicins A and B." Journal of Bacteriology, (2004) 186: 1598-1605.) As long as the cell has one or more plasmids comprising an antitoxin gene, the toxin is neutralized by the antitoxin that is continuously expressed by the one or more plasmids to keep the cells alive. In certain prokaryotes, the antitoxin protein degrades faster than the toxin protein. If the plasmid comprising the antitoxin gene is lost from the cell, the toxin protein will exist longer than the antitoxin protein in the cell and kill or inhibit the growth of the cell. Therefore, plasmids comprising the antitoxin or the toxin/antitoxin gene are preferably maintained to keep the host cell alive.

As used herein, a toxin/antitoxin gene pair has two genes, one is a toxin gene which expresses a polypeptide toxic to a host cell, and the other is an antitoxin gene which neutralizes the toxic polypeptide in the host cell. Examples of the toxin/antitoxin gene pair include, without limitation, abt/abi gene pair and aat/aai gene pair, fragments thereof, and mutants thereof. In some embodiments, the toxin polynucleotide sequence comprises, consists of, or consists essentially of the nucleotide sequence of SEQ ID NO: 23 or SEQ ID NO: 25, fragments thereof, or mutants thereof. In some embodiments, the antitoxin polynucleotide sequence comprises, consists of, or consists essentially of the nucleotide sequence of SEQ ID NO: 24 or SEQ ID NO: 26, fragments thereof, or mutants thereof.

In certain embodiments, the host cell may be any *H. alvei* strain, e.g., endogenous plasmid-free *H. alvei* strains or *H. alvei* strains containing endogenous plasmids. For example, the host cell may be an *H. alvei* strain containing one or more pAlvA plasm ids or the cured strains thereof (pAlvA-strains), or an *H. alvei* strain containing one or more pAlvB plasm ids and the cured strains thereof (pAlvB-strains).

In certain embodiments, the expression plasmid vector disclosed herein (e.g. the expression plasmid vector) may further comprise one or more antitoxin genes selected from the group consisting of abi gene, aai gene, mutations and fragments thereof, and/or one or more toxin/antitoxin gene pairs selected from the group consisting of abt/abi gene pair and aat/aai gene pair, and mutations and fragments thereof. For example, in certain embodiments, an expression plasmid vector (e.g. the expression plasmid vector) may further comprise an antitoxin polynucleotide that counteracts a toxin polypeptide that is harmful to the host cell, and a toxin polynucleotide sequence encoding the toxin polypeptide.

In certain embodiments, the host cell may be an industrial strain suitable to be used in industrial-scale or large-scale production. For example, industrial strains may be cultivated in a fermenter. The scale of culture may range from hundreds of liters to millions of liters. On the other hand, a laboratory strain usually is cultivated in a few liters or less. In certain embodiments, an industrial strain may grow in a simpler or more economical medium than laboratory strains.

A backbone plasmid capable of autonomous replication in a host cell may be any plasmid that can replicate in the host cell. In one embodiment, an expression plasmid vector comprises a backbone plasmid that can replicate in *E. coli*. In another embodiment, an expression plasmid vector comprises a backbone plasmid that can replicate in *H. alvei*. Examples of the backbone plasmids include, without limitation, backbone plasmids that can replicate in *E. coli* strains, e.g. pUC (e.g. pUC18 and pUC19 plasmids), pBR322, pSC101, pET, p15a, and pACYC plasmids, and plasmids derived therefrom.

In certain embodiments, the expression plasmid vector may be used for the production of a lysine derived product as described herein. In certain embodiments, a lysine derived product may be cadaverine as described herein.

As provided above, in certain embodiments, the DNA polynucleotide described herein may further comprise one or more RBS DNA nucleotide sequences selected from the group consisting of SEQ ID NO: 14 (i.e., RBS DNA-1), SEQ ID NO: 15 (i.e., RBS DNA-2), SEQ ID NO: 16 (i.e., RBS DNA-3), SEQ ID NO: 17 (i.e., RBS DNA-4), SEQ ID NO: 18 (i.e., RBS DNA-5), and SEQ ID NO: 19 (i.e., RBS DNA-6). In certain preferred embodiments, the one or more RBS DNA nucleotide sequences may comprise, consist of, or consist essentially of SEQ ID NO: 18 (i.e., RBS DNA-5).

As provided above, in certain embodiments, the DNA polynucleotide described herein may further comprise one or more promoter nucleotide sequences selected from the group consisting of SEQ ID NO: 20 (i.e., Plac promoter sequence), SEQ ID NO: 21 (i.e., Pbad promoter sequence), and SEQ ID NO: 22 (i.e., Ptac promoter sequence). In certain preferred embodiments, the one or more promoter nucleotide sequences may comprise, consist of, or consist essentially of SEQ ID NO: 21 (i.e., Pbad promoter sequence).

Another aspect provided herein relates to a transformant comprising, consisting of, or consisting essentially of one or more expression plasmid vectors in a host cell, the expression plasmid vectors comprising, consisting of, or consisting essentially of:

a DNA polynucleotide comprising, consisting of, or consisting essentially of one or more lysine decarboxylase nucleotide sequences selected from the group consisting of mutants of SEQ ID NO: 1 (i.e., mutants of *K. oxytoca* ldc) and fragments thereof, and fragments of SEQ ID NO: 1 (i.e., fragments of *K. oxytoca* ldc), wherein the lysine decarboxylase nucleotide sequences have at least 95% sequence identity with SEQ ID NO: 1 or SEQ ID NO: 3, and wherein the polynucleotide encodes one or more lysine decarboxylase polypeptides comprising, consisting of, or consisting essentially of an amino acid sequence selected from the group consisting of SEQ ID NO: 2 (i.e., *K. oxytoca* Ldc) and fragments thereof, and mutants of SEQ ID NO: 2 (i.e., mutants of *K. oxytoca* Ldc) and fragments thereof; and a backbone plasmid capable of autonomous replication in a host cell, wherein the expression plasmid vector is used for production of a lysine-derived product.

The expression plasmid vectors; host cell; backbone plasmid; DNA polynucleotides; lysine decarboxylase nucleotide sequences; *K. oxytoca* ldc, mutants, and fragments thereof; lysine decarboxylase polypeptides; *K. oxytoca* Ldc, mutants, and fragments thereof are the same as described supra.

An example of a mutant of SEQ ID NO: 1 (i.e., mutant of *K. oxytoca* ldc) may include, without limitation, the nucleotide sequence of SEQ ID NO: 1 (i.e., *K. oxytoca* ldc) that has been codon-optimized for expression in *E. coli* (i.e., *K. oxytoca* ldc-co1, SEQ ID NO: 3) and that encodes the amino acid sequence of SEQ ID NO: 2 (i.e., *K. oxytoca* Ldc). Other examples of mutants of SEQ ID NO: 1 (i.e., mutants of *K. oxytoca* ldc) may include, without limitation, lysine decarboxylase nucleotide sequences that encode amino acid sequences of mutants of SEQ ID NO: 2 (i.e., mutants of *K. oxytoca* Ldc). Examples of preferred mutants of SEQ ID NO: 1 (i.e., mutants of *K. oxytoca* ldc) that encode an amino acid sequence of mutants of SEQ ID NO: 2 (i.e., mutants of *K. oxytoca* Ldc) include, without limitation, SEQ ID NO: 4 (i.e., *K. oxytoca* ldc-co1 A859G), SEQ ID NO: 6 (i.e., *K. oxytoca* ldc-co-1 C1193G), SEQ ID NO: 8 (i.e., *K. oxytoca* ldc-co1 C1306G), SEQ ID NO: 10 (i.e., *K. oxytoca* ldc-co1 C1521G), and SEQ ID NO: 12 (i.e., *K. oxytoca* ldc-co1 T1820A).

Additional examples of mutants of SEQ ID NO: 1 (i.e., mutants of *K. oxytoca* ldc) that encode an amino acid sequence of mutants of SEQ ID NO: 2 (i.e., mutants of *K. oxytoca* Ldc) may include, without limitation, lysine decarboxylase nucleotide sequences comprising, consisting of, or consisting essentially of SEQ ID NO: 1 or SEQ ID NO: 3 comprising one or more mutations selected from the group consisting of a mutation at nucleotide position 859 to $Z_1$, a mutation at nucleotide position 1193 to $Z_2$, a mutation at nucleotide position 1306 to $Z_3$, a mutation at nucleotide position 1521 to $Z_4$, a mutation at nucleotide position 1820 to $Z_5$, and/or any combination thereof; lysine decarboxylase nucleotide sequences comprising, consisting of, or consisting essentially of SEQ ID NO: 1 or SEQ ID NO: 3 comprising one or more mutations selected from the group consisting of a mutation at nucleotide position 859 mutated to a G (guanine), a mutation at nucleotide position 1193 mutated to a G, a mutation at nucleotide position 1306 mutated to a G, a mutation at nucleotide position 1521 mutated to a G or an A (adenine), a mutation at nucleotide position 1820 mutated to an A, and/or any combination thereof; homologous nucleotide sequences of *K. oxytoca* ldc A859G or *K. oxytoca* ldc-co1 A859G (e.g., *K. oxytoca* ldc A859$Z_1$ or *K. oxytoca* ldc-co1 A859$Z_1$); homologous nucleotide sequences of *K. oxytoca* ldc C1193G or *K. oxytoca* ldc-co1 C1193G (e.g., *K. oxytoca* ldc C1193$Z_2$ or *K. oxytoca* ldc-co1 C1193$Z_2$); homologous nucleotide sequences of *K. oxytoca* ldc C1306G or *K. oxytoca* ldc-co1 C1306G (e.g., *K. oxytoca* ldc C1306$Z_3$ or *K. oxytoca* ldc-co1 C1306$Z_3$); homologous nucleotide sequences of *K. oxytoca* ldc C1521G or *K. oxytoca* ldc-co1 C1521G (e.g., *K. oxytoca* ldc C1521$Z_4$ or *K. oxytoca* ldc-co1 C1521$Z_4$); and homologous nucleotide sequences of *K. oxytoca* ldc T1820A or *K. oxytoca* ldc-co1 T1820A (e.g., *K. oxytoca* ldc T1820$Z_5$ or *K. oxytoca* ldc-co1 T1820$Z_5$). $Z_1$, $Z_2$, $Z_3$, $Z_4$, and $Z_5$ are each independently selected from the group consisting of A, G, C (cytosine), and T (thymine), with the proviso that $Z_1$ is not an A, $Z_2$ is not a C, $Z_3$ is not a C, $Z_4$ is not a C or T, and $Z_5$ is not a T.

Examples of preferred mutants of SEQ ID NO: 2 (i.e., mutants of *K. oxytoca* Ldc) include, without limitation, SEQ ID NO: 5 (i.e., *K. oxytoca* Ldc K287E); SEQ ID NO: 7 (i.e., *K. oxytoca* Ldc T398S); SEQ ID NO: 9 (i.e., *K. oxytoca* Ldc R436G); SEQ ID NO: 11 (i.e., *K. oxytoca* Ldc F507L); and SEQ ID NO: 13 (i.e., *K. oxytoca* Ldc F607Y). Additional examples of mutants of SEQ ID NO: 2 (i.e., mutants of *K. oxytoca* Ldc) include, without limitation, mutants comprising, consisting of, or consisting essentially of the amino acid sequence of SEQ ID NO: 2 comprising one or more mutations selected from the group consisting of a mutation at amino acid position 287 to $X_1$, a mutation at amino acid position 398 to $X_2$, a mutation at amino acid position 436 to $X_3$, a mutation at amino acid position 507 to $X_4$, a mutation at amino acid position 607 to $X_5$; homologous polypeptides of SEQ ID NO: 5 (e.g., *K. oxytoca* Ldc K287$X_1$); homologous polypeptides of SEQ ID NO: 7 (e.g., *K. oxytoca* Ldc T398$X_2$); homologous polypeptides of SEQ ID NO: 9 (e.g., *K. oxytoca* Ldc R436$X_3$); homologous polypeptides of SEQ ID NO: 11 (e.g., *K. oxytoca* Ldc F507$X_4$); and homologous polypeptides of SEQ ID NO: 13 (e.g., *K. oxytoca* Ldc F607$X_5$). $X_1$, $X_2$, $X_3$, $X_4$, and $X_5$ are each independently selected from the group consisting of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine, with the proviso that $X_1$ is not lysine, $X_2$ is not threonine, $X_3$ is not arginine, $X_4$ is not phenylalanine, and $X_5$ is not phenylalanine.

As provided above, in certain embodiments, the DNA polynucleotide described herein may further comprise one or more RBS DNA nucleotide sequences selected from the group consisting of SEQ ID NO: 14 (i.e., RBS DNA-1), SEQ ID NO: 15 (i.e., RBS DNA-2), SEQ ID NO: 16 (i.e., RBS DNA-3), SEQ ID NO: 17 (i.e., RBS DNA-4), SEQ ID NO: 18 (i.e., RBS DNA-5), and SEQ ID NO: 19 (i.e., RBS DNA-6). In certain preferred embodiments, the one or more RBS DNA nucleotide sequences may comprise, consist of, or consist essentially of SEQ ID NO: 18 (i.e., RBS DNA-5).

As provided above, in certain embodiments, the DNA polynucleotide described herein may further comprise one or more promoter nucleotide sequences selected from the group consisting of SEQ ID NO: 20 (i.e., Plac promoter sequence), SEQ ID NO: 21 (i.e., Pbad promoter sequence), and SEQ ID NO: 22 (i.e., Ptac promoter sequence). In certain preferred embodiments, the one or more promoter nucleotide sequences may comprise, consist of, or consist essentially of SEQ ID NO: 21 (i.e., Pbad promoter sequence).

As used herein, a transformant may be a host cell that has been altered by introducing one or more expression plasmid vectors in the host cell. In certain embodiments, the transformant may be obtained by introducing an expression plasmid vector through transformation into a host cell displaying competence to the plasmid vector.

In certain embodiments, the transformant may be used for the production of a lysine derived product as described herein. In certain embodiments, a lysine derived product may be cadaverine as described herein.

Another aspect provided herein relates to a mutant host cell comprising, consisting of, consisting essentially of:

a DNA polynucleotide comprising one or more lysine decarboxylase nucleotide sequences selected from the group consisting of mutants of SEQ ID NO: 1 (i.e., mutants of *K. oxytoca* ldc) and fragments thereof, and fragments of SEQ ID NO: 1 (i.e., fragments of *K. oxytoca* ldc), wherein the lysine decarboxylase nucleotide sequences have at least 95% sequence identity with SEQ ID NO: 1 or SEQ ID NO: 3, and wherein the polynucleotide encodes one or more lysine decarboxylase polypeptides comprising an amino acid sequence selected from the group consisting of SEQ ID NO: 2 (i.e., *K. oxytoca* Ldc) and fragments thereof, and mutants of SEQ ID NO: 2 (i.e., mutants of *K. oxytoca* Ldc) and fragments thereof.

The host cell; DNA polynucleotides; lysine decarboxylase nucleotide sequences; *K. oxytoca* ldc, fragments, and mutants thereof; lysine decarboxylase polypeptides; *K. oxytoca* Ldc, fragments, and mutants thereof are the same as described supra.

An example of a mutant of SEQ ID NO: 1 (i.e., mutant of *K. oxytoca* ldc) may include, without limitation, the nucleotide sequence of SEQ ID NO: 1 (i.e., *K. oxytoca* ldc) that has been codon-optimized for expression in *E. coli* (i.e., *K. oxytoca* ldc-co1, SEQ ID NO: 3) and that encodes the amino acid sequence of SEQ ID NO: 2 (i.e., *K. oxytoca* Ldc). Other examples of mutants of SEQ ID NO: 1 (i.e., mutants of *K. oxytoca* ldc) may include, without limitation, lysine decarboxylase nucleotide sequences that encode amino acid sequences of mutants of SEQ ID NO: 2 (i.e., mutants of *K. oxytoca* Ldc). Examples of preferred mutants of SEQ ID NO: 1 (i.e., mutants of *K. oxytoca* ldc) that encode an amino acid sequence of mutants of SEQ ID NO: 2 (i.e., mutants of *K. oxytoca* Ldc) include, without limitation, SEQ ID NO: 4 (i.e., *K. oxytoca* ldc-co1 A859G), SEQ ID NO: 6 (i.e., *K. oxytoca* ldc-co1 C1193G), SEQ ID NO: 8 (i.e., *K. oxytoca* ldc-co1 C1306G), SEQ ID NO: 10 (i.e., *K. oxytoca* ldc-co1 C1521G), and SEQ ID NO: 12 (i.e., *K. oxytoca* ldc-co1 T1820A).

Additional examples of mutants of SEQ ID NO: 1 (i.e., mutants of *K. oxytoca* ldc) that encode an amino acid sequence of mutants of SEQ ID NO: 2 (i.e., mutants of *K. oxytoca* Ldc) may include, without limitation, lysine decarboxylase nucleotide sequences comprising, consisting of, or consisting essentially of SEQ ID NO: 1 or SEQ ID NO: 3 comprising one or more mutations selected from the group consisting of a mutation at nucleotide position 859 to $Z_1$, a mutation at nucleotide position 1193 to $Z_2$, a mutation at nucleotide position 1306 to $Z_3$, a mutation at nucleotide position 1521 to $Z_4$, a mutation at nucleotide position 1820 to $Z_5$, and/or any combination thereof; lysine decarboxylase nucleotide sequences comprising, consisting of, or consisting essentially of SEQ ID NO: 1 or SEQ ID NO: 3 comprising one or more mutations selected from the group consisting of a mutation at nucleotide position 859 mutated to a G (guanine), a mutation at nucleotide position 1193 mutated to a G, a mutation at nucleotide position 1306 mutated to a G, a mutation at nucleotide position 1521 mutated to a G or an A (adenine), a mutation at nucleotide position 1820 mutated to an A, and/or any combination thereof; homologous nucleotide sequences of *K. oxytoca* ldc A859G or *K. oxytoca* ldc-co1 A859G (e.g., *K. oxytoca* ldc A859$Z_1$ or *K. oxytoca* ldc-co1 A859$Z_1$); homologous nucleotide sequences of *K. oxytoca* ldc C1193G or *K. oxytoca* ldc-co1 C1193G (e.g., *K. oxytoca* ldc C1193$Z_2$ or *K. oxytoca* ldc-co1 C1193$Z_2$); homologous nucleotide sequences of *K. oxytoca* ldc C1306G or *K. oxytoca* ldc-co1 C1306G (e.g., *K. oxytoca* ldc C1306$Z_3$ or *K. oxytoca* ldc-co1 C1306$Z_3$); homologous nucleotide sequences of *K. oxytoca* ldc C1521G or *K. oxytoca* ldc-co1 C1521G (e.g., *K. oxytoca* ldc C1521$Z_4$ or *K. oxytoca* ldc-co1 C1521$Z_4$); and homologous nucleotide sequences of *K. oxytoca* ldc T1820A or *K. oxytoca* ldc-co1 T1820A (e.g., *K. oxytoca* ldc T1820$Z_5$ or *K. oxytoca* ldc-co1 T1820$Z_5$). $Z_1$, $Z_2$, $Z_3$, $Z_4$, and $Z_5$ are each independently selected from the group consisting of A, G, C (cytosine), and T (thymine), with the proviso that $Z_1$ is not an A, $Z_2$ is not a C, $Z_3$ is not a C, $Z_4$ is not a C or T, and $Z_5$ is not a T.

Examples of preferred mutants of SEQ ID NO: 2 (i.e., mutants of *K. oxytoca* Ldc) include, without limitation, SEQ ID NO: 5 (i.e., *K. oxytoca* Ldc K287E); SEQ ID NO: 7 (i.e., *K. oxytoca* Ldc T398S); SEQ ID NO: 9 (i.e., *K. oxytoca* Ldc R436G); SEQ ID NO: 11 (i.e., *K. oxytoca* Ldc F507L); and SEQ ID NO: 13 (i.e., *K. oxytoca* Ldc F607Y). Additional examples of mutants of SEQ ID NO: 2 (i.e., mutants of *K. oxytoca* Ldc) include, without limitation, mutants comprising, consisting of, or consisting essentially of the amino acid sequence of SEQ ID NO: 2 comprising one or more mutations selected from the group consisting of a mutation at amino acid position 287 to $X_1$, a mutation at amino acid position 398 to $X_2$, a mutation at amino acid position 436 to $X_3$, a mutation at amino acid position 507 to $X_4$, a mutation at amino acid position 607 to $X_5$; homologous polypeptides of SEQ ID NO: 5 (e.g., *K. oxytoca* Ldc K287$X_1$); homologous polypeptides of SEQ ID NO: 7 (e.g., *K. oxytoca* Ldc T398$X_2$); homologous polypeptides of SEQ ID NO: 9 (e.g., *K. oxytoca* Ldc R436$X_3$); homologous polypeptides of SEQ ID NO: 11 (e.g., *K. oxytoca* Ldc F507$X_4$); and homologous polypeptides of SEQ ID NO: 13 (e.g., *K. oxytoca* Ldc F607$X_5$). $X_1$, $X_2$, $X_3$, $X_4$, and $X_5$ are each independently selected from the group consisting of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine, with the proviso that $X_1$ is not lysine, $X_2$ is not threonine, $X_3$ is not arginine, $X_4$ is not phenylalanine, and $X_5$ is not phenylalanine.

As provided above, in certain embodiments, the DNA polynucleotide described herein may further comprise one or more RBS DNA nucleotide sequences selected from the group consisting of SEQ ID NO: 14 (i.e., RBS DNA-1), SEQ ID NO: 15 (i.e., RBS DNA-2), SEQ ID NO: 16 (i.e., RBS DNA-3), SEQ ID NO: 17 (i.e., RBS DNA-4), SEQ ID NO: 18 (i.e., RBS DNA-5), and SEQ ID NO: 19 (i.e., RBS DNA-6).

As provided above, in certain embodiments, the DNA polynucleotide described herein may further comprise, consist of, or consist essentially of one or more promoter nucleotide sequences selected from the group consisting of SEQ ID NO: 20 (i.e., Plac promoter sequence), SEQ ID NO: 21 (i.e., Pbad promoter sequence), and SEQ ID NO: 22 (i.e., Ptac promoter sequence). In certain preferred embodiments, the one or more promoter nucleotide sequences may comprise, consist of, or consist essentially of SEQ ID NO: 21 (i.e., Pbad promoter sequence).

In certain embodiments, the mutant host cell may be used for the production of a lysine derived product as described herein. In certain embodiments, a lysine derived product may be cadaverine as described herein.

In certain embodiments, the DNA polynucleotide may be integrated into the host cell chromosome according to the PCR-mediated gene replacement method (see, e.g. Datsenko, 2000 for an overview of the PCR-mediated gene replacement method, which is incorporated herein by reference in its entirety). Integrated chromosomes may also be produced by other suitable methods.

Another aspect of the invention relates to a method for producing one or more lysine decarboxylase polypeptides described herein comprising:
obtaining a mutant host cell and/or the transformant as described herein;
culturing the mutant host cell and/or transformant under conditions effective for the expression of the one or more lysine decarboxylase polypeptides; and
harvesting the one or more lysine decarboxylase polypeptides.

The lysine decarboxylase polypeptides; *K. oxytoca* Ldc, mutants, and fragments thereof; mutant host cell and/or transformants are the same as described supra.

In certain embodiments, the transformant and/or mutant host cell may be any of those as described herein. For example, the transformant used to produce one or more lysine decarboxylase polypeptides may be obtained by transforming one or more expression plasmid vectors as disclosed herein into a host cell.

The transformant and/or mutant host cell may be cultured using a medium containing carbon sources and non-carbon nutrient sources. Examples of carbon sources include, without limitation, sugar (e.g. carbohydrates such as glucose and fructose), oil and/or fat, fatty acid, and/or derivatives thereof. The oil and fat may contain saturated and/or unsaturated fatty acids having 10 or more carbon atoms, e.g. coconut oil, palm oil, palm kernel oil, and the like. The fatty acid may be a saturated and/or unsaturated fatty acid, e.g. hexanoic acid, octanoic acid, decanoic acid, lauric acid, oleic acid, palmitic acid, linoleic acid, linolenic acid, myristic acid, and the like. Examples of derivatives of a fatty acid include, without limitation, esters and salts thereof. Examples of non-carbon sources include, without limitation, nitrogen sources, inorganic salts, and other organic nutrient sources.

For example, a medium may contain a carbon source assimilable by the transformant and/or mutant host cell, optionally with one or more other source selected from the group consisting of a nitrogen source, an inorganic salt and another organic nutrient source. In certain embodiments, the weight percentage of the nitrogen source is about 0.01 to about 0.1% of the medium. Examples of the nitrogen source may comprise ammonia, ammonium salts (e.g. ammonium chloride, ammonium sulfate and ammonium phosphate), peptone, meat extract, yeast extract, and the like. Examples of the inorganic salts include, without limitation, potassium dihydrogen phosphate, dipotassium hydrogen phosphate, magnesium phosphate, magnesium sulfate, sodium chloride, and the like. Examples of the other organic nutrient source include, without limitation, amino acids (e.g. glycine, alanine, serine, threonine and proline), vitamins (e.g. vitamin B1, vitamin B12 and vitamin C), and the like.

The culture may be carried out at any temperature as long as the cells can grow, and preferably at about 20° C. to about 40° C., or about 35° C. The culture period may be about 1, about 2, about 3, about 4, about 5, about 6, about 7, about 8, about 9, or about 10 days.

In one embodiment, the transformant and/or mutant host cell is cultured in a medium containing peptides, peptones, vitamins (e.g. B vitamins), trace elements (e.g. nitrogen, sulfur, magnesium), and minerals. Examples of such medium include, without limitation, commonly known Lysogeny broth (LB) mediums comprising tryptone, yeast extract and NaCl suspended in water (e.g. distilled or deionized).

Another aspect provided herein relates to a method for producing cadaverine (1,5-pentanediamine) comprising, consisting of, or consisting essentially of:
1a) cultivating a transformant and/or mutant host cell as disclosed herein,
1b) producing cadaverine using the culture obtained from step 1a to decarboxylate lysine, and
1c) extracting and purifying cadaverine using the culture obtained from step 1b.

In certain embodiments, the transformant and/or mutant host cell may be any of those as described herein.

Cultivating the transformant and/or mutant host cell may comprise the steps of culturing the transformant as described supra.

For example, the transformant and/or mutant host cell may be cultured using a medium containing carbon sources and non-carbon nutrient sources. Examples of carbon sources include, without limitation, sugar (e.g. carbohydrates such as glucose and fructose), oil and/or fat, fatty acid, and/or derivatives thereof. The oil and fat may contain saturated and/or unsaturated fatty acids having 10 or more carbon atoms, e.g. coconut oil, palm oil, palm kernel oil, and the like. The fatty acid may be a saturated and/or unsaturated fatty acid, e.g. hexanoic acid, octanoic acid, decanoic acid, lauric acid, oleic acid, palmitic acid, linoleic acid, linolenic acid, myristic acid, and the like. Examples of derivatives of a fatty acid include, without limitation, esters and salts thereof. Examples of non-carbon sources include, without limitation, nitrogen sources, inorganic salts, and other organic nutrient sources.

For example, a medium may contain a carbon source assimilable by the transformant and/or mutant host cell, optionally with one or more other source selected from the group consisting of a nitrogen source, an inorganic salt and another organic nutrient source. In certain embodiments, the weight percentage of the nitrogen source is about 0.01 to about 0.1% of the medium. Examples of the nitrogen source may comprise ammonia, ammonium salts (e.g. ammonium chloride, ammonium sulfate and ammonium phosphate), peptone, meat extract, yeast extract, and the like. Examples of the inorganic salts include, without limitation, potassium dihydrogen phosphate, dipotassium hydrogen phosphate, magnesium phosphate, magnesium sulfate, sodium chloride, and the like. Examples of the other organic nutrient source include, without limitation, amino acids (e.g. glycine, alanine, serine, threonine and proline), vitamins (e.g. vitamin B1, vitamin B12 and vitamin C), and the like.

The culture may be carried out at any temperature as long as the cells can grow, and preferably at about 20° C. to about 40° C., or about 35° C. The culture period may be about 1, about 2, about 3, about 4, about 5, about 6, about 7, about 8, about 9, or about 10 days.

In one embodiment, the transformant and/or mutant host cell is cultured in a medium containing peptides, peptones, vitamins (e.g. B vitamins), trace elements (e.g. nitrogen, sulfur, magnesium), and minerals. Examples of such medium include, without limitation, commonly known Lysogeny broth (LB) mediums comprising tryptone, yeast extract and NaCl suspended in water (e.g. distilled or deionized).

As used herein, "using the culture obtained from step 1a" may comprise further processes of the culture obtained from step 1a. For example, using a buffer solution to dilute the culture; centrifuging the culture to collect the cells; resuspending the cells in a buffer solution; or lysing the cells into cell lysate; or/and purifying lysine decarboxylase from the cell lysate.

In another embodiment, step 1c of the method further comprises the following steps:

1d) separating the solid and liquid components of the reaction obtained from step 1b;

1e) adjusting the pH of the liquid component obtained from step 1d to about 14 or higher;

1f) removing water from the liquid component obtained from step 1e; and 1g) recovering cadaverine.

In step 1d, the separation of the solid and liquid components of the In step 1e, the pH of the liquid component of step 1d may be adjusted by adding a base, e.g. NaOH. NaOH may be added as a solid and/or a solution (e.g. an aqueous solution).

In step 1f, the water may be removed by distillation at ambient pressure or under vacuum.

In step 1g, cadaverine may be recovered by distillation at ambient pressure or under vacuum.

Another aspect provided herein relates to a method for producing cadaverine (1,5-pentanediamine) comprising, consisting of, or consisting essentially of:

2a) obtaining one or more lysine decarboxylase polypeptides comprising the amino acid sequence selected from the group consisting of SEQ ID NO: 2 (i.e., *K. oxytoca* Ldc) and fragments thereof, and mutants of SEQ ID NO: 2 (i.e., mutants of *K. oxytoca* Ldc) and fragments thereof; and 2b) producing cadaverine using the one or more lysine decarboxylase polypeptides obtained in step 2a to decarboxylate lysine.

The lysine decarboxylase polypeptides; *K. oxytoca* Ldc, mutants, and fragments thereof are the same as described supra.

In certain embodiments, the method for producing cadaverine may further include the step of 2c comprising extracting and purifying cadaverine produced in step 2b.

In another embodiment, step 2c of the method further comprises the following steps:

2d) separating the solid and liquid components of the reaction obtained from step 2b;

2e) adjusting the pH of the liquid component obtained from step 2d to about 14 or higher;

2f) removing water from the liquid component obtained from step 2e; and 2g) recovering cadaverine.

In step 2d, the separation of the solid and liquid components of the reaction of step 2b may be accomplished by conventional centrifugation and/or filtration.

In step 2e, the pH of the liquid component of step 2d may be adjusted by adding a base, e.g. NaOH. NaOH may be added as a solid and/or a solution (e.g. an aqueous solution).

In step 2f, the water may be removed by distillation at ambient pressure or under vacuum.

In step 2g, cadaverine may be recovered by distillation at ambient pressure or under vacuum.

In certain embodiments, the one or more lysine decarboxylase polypeptides used to produce cadaverine may be immobilized. In certain embodiments, the one or more lysine decarboxylase polypeptides may be confined to a matrix. In certain embodiments, the one or more lysine decarboxylase polypeptides may be immobilized using any suitable method known to one of ordinary skill in the art. Examples of immobilization techniques include, without limitation, adsorption (e.g., from ionic or hydrophobic interactions), covalent binding, affinity immobilization (e.g., the matrix is coupled to an affinity ligand for the one or more lysine decarboxylase polypeptides, or the one or more lysine decarboxylase polypeptides are conjugated to a molecule having affinity for the matrix), and entrapment (i.e. caging of the one or more lysine decarboxylase polypeptides by covalent or noncovalent interactions with the matrix). Examples of materials that may be used as a matrix include, without limitation, alginate, chitosan, chitin, collagen, carrageenan, gelatin, cellulose, starch, pectin, sepharose, zeolites, ceramics, celite, silica, glass, activated carbon, and charcoal.

Another aspect provided herein relates to biobased cadaverine prepared according to the method disclosed herein.

As used herein, a "biobased" compound means the compound is considered biobased under Standard ASTM D6866.

Another aspect provided herein relates to a polyamide having a structure of Structure 1:

Structure 1

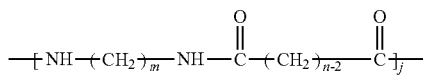

including stereoisomers thereof, wherein:

m=4, 5, 6, 7, 8, 9, 10, 11, 12, 13, 14, 15, 16, 17, 18, 19, 20, 21, or 22;

n=4, 5, 6, 7, 8, 9, 10, 11, 12, 13, 14, 15, 16, 17, 18, 19, 20, 21, or 22;

j=about 100~about 1,000,000; and the polyamide is prepared from one or more diamines having carbon numbers of m and one or more dicarboxylic acids having carbon numbers of n, at least one of the diamines and dicarboxylic acids comprises biobased carbon under Standard ASTM D6866, and the m or n of each diamine or dicarboxylic acid can be the same or different.

In one embodiment, the diamine is biobased cadaverine, more preferably biobased cadaverine prepared according to the method disclosed herein. Examples of the dicarboxylic acids include, without limitation, $C_{10}$dicarboxylic acid, $C_{11}$dicarboxylic acid, $C_{12}$dicarboxylic acid, $C_{13}$dicarboxylic acid, $C_{14}$dicarboxylic acid, $C_{16}$dicarboxylic acid, $C_{18}$dicarboxylic acid, and any combinations thereof. In certain embodiments, all or part of the $C_n$dicarboxylic acids are biobased.

In another embodiments, the polyamide has a structure described above, wherein:

the polyamide is formed by reacting biobased cadaverine with one or more dicarboxylic acids, more preferably the biobased cadaverine is prepared according to the method disclosed herein;

n=4, 5, 6, 7, 8, 9, 10, 11, 12, 13, 14, 15, 16, 17, 18, 19, 20, 21, or 22;

j=about 100~about 1,000,000, about 1000~about 100,000, or about 1000~about 10,000; and the dicarboxylic acids comprise biobased carbon under Standard ASTM D6866.

Another aspect provided herein relates to a method of making the polyamides disclosed herein comprising preparing biobased cadaverine as the $C_m$ diamine according to the method disclosed herein.

In one embodiment, the method further comprises preparing one or more biobased $C_n$ dicarboxylic acids.

In another embodiment, the method further comprises preparing the polyamide by reacting biobased cadaverine with one or more biobased $C_n$ dicarboxylic acids.

Another aspect provided herein relates to a composition comprising one or more polyamides disclosed herein.

In one embodiment, the diamine is biobased cadaverine, more preferably biobased cadaverine prepared according to the method disclosed herein. Examples of the dicarboxylic acids include, without limitation, $C_{10}$ dicarboxylic acid, $C_{11}$ dicarboxylic acid, $C_{12}$ dicarboxylic acid, $C_{13}$ dicarboxylic acid, $C_{14}$ dicarboxylic acid, $C_{16}$ dicarboxylic acid, $C_{18}$ dicarboxylic acid, and any combinations thereof. In certain embodiments, all or part of the $C_n$ dicarboxylic acids are biobased.

In another embodiment, the polyamide has a structure described above, wherein:

the polyamide is formed by reacting biobased cadaverine with one or more dicarboxylic acids, more preferably the biobased cadaverine is prepared according to the method disclosed herein;

n=4, 5, 6, 7, 8, 9, 10, 11, 12, 13, 14, 15, 16, 17, 18, 19, 20, 21, or 22;

j=about 100~about 1,000,000, about 1000~about 100,000, or about 1000~about 10,000; and the dicarboxylic acids comprise biobased carbon under Standard ASTM D6866.

Another aspect provided herein relates to a method of preparing 1,5-diisocyanatopentane comprising:

3a) preparing biobased cadaverine as disclosed herein; and 3b) converting biobased cadaverine obtained from step 3a to 1,5-diisocyanatopentane.

Step 3b may comprise using any known method to convert diamine into isocyanate. An example of said method is the traditional phosgene method, which includes one-step high temperature phosgene method (i.e. mixing phosgene with diamine at high temperature to obtain isocyanate), the improved two-step phosgene method, and the triphosgene method in which triphosgene is used instead of phosgene. There are also other methods that do not use phosgene as a raw material. An example of said method is hexanediamine carbonylation which uses $CO_2$ instead of phosgene: $CO_2$ is added into a solution of a primary amine and an organic base, then a proper amount of phosphorus electrophilic reagents is added into the reaction solution to start an exothermic dehydration reaction to obtain isocyanate. Another example is carbamate thermal decomposition method wherein a primary amine is converted to a carbamate, and then the carbamate is heated to decompose and generate isocyanate.

The abbreviations used for the amino acids, polypeptides, base sequences, and nucleic acids are based on the abbreviations specified in the IUPAC-IUB Communication on Biochemical Nomenclature, Eur. J. Biochem., 138:9 (1984), "Guideline for Preparing Specifications Including Base Sequences and Amino Acid Sequences" (United States Patent and Trademark Office), and those commonly used in this technical field.

Unless the context clearly requires otherwise, throughout the description and the claims, the words "comprise," "comprising," and the like are to be construed in an inclusive sense (i.e., to say, in the sense of "including, but not limited to"), as opposed to an exclusive or exhaustive sense. The words "herein," "above," "below," "supra," and words of similar import; when used in this application, refer to this application as a whole and not to any particular portions of this application. Where the context permits, words in the above Detailed Description using the singular or plural number may also include the plural or singular number respectively. The words "or," and "and/or" in reference to a list of two or more items, covers all of the following interpretations of the word: any of the items in the list, all of the items in the list, and any combination of the items in the list.

The following examples are intended to illustrate various embodiments of the invention. As such, the specific embodiments discussed are not to be construed as limitations on the scope of the invention. It will be apparent to one skilled in the art that various equivalents, changes, and modifications may be made without departing from the scope of invention, and it is understood that such equivalent embodiments are to be included herein. Further, all references cited in the disclosure are hereby incorporated by reference in their entirety, as if fully set forth herein.

EXAMPLES

Example 1: Overexpression of *K. Oxytoca* Lysine Decarboxylase in *E. Coli*

*K. oxytoca* genomic DNA was purchased from DSMZ (DSM 6673). The genomic DNA was used as a template in a PCR reaction with the primers KOldc-F and KOldc-R (see FIG. 1). The primers were designed based on GenBank accession CP003683.1, which is the portion of the *K. oxytoca* E718 genome that contains the wild-type lysine decarboxylase (ldc) gene. The *K. oxytoca* ldc nucleotide sequence (SEQ ID NO: 1) encodes the lysine decarboxylase protein, *K. oxytoca* Ldc (SEQ ID NO: 2). The amplified PCR product was cloned into the plasmid pUC18 using the restriction enzymes SacI and XbaI to create pUC18-KOldc. After the lysine decarboxylase sequence was verified, pUC18-KOldc was transformed into *E. coli* MG1655 K12 (DSM 18039) (K12) to create strain LN18 (see FIG. 2). The sequence of *K. oxytoca* ldc was codon optimized for expression in *E. coli* (*K. oxytoca* ldc-co-1; SEQ ID NO: 3). The codon-optimized gene (*K. oxytoca* ldc-co-1) was cloned into pUC18 as described above to create the plasmid pUC18-KOldc-co1, and the plasmid was transformed into *E. coli* K12 to make the strain LN20 (see FIG. 2). A plasmid vector containing wild-type *E. coli* cadA, which encodes the lysine decarboxylase polypeptide CadA, was constructed by cloning wild-type *E. coli* cadA into pUC18 to generate the positive control, pCIB60. pCIB60 was transformed into *E. coli* K12 to generate strain CIB60 (see FIG. 2).

Three colonies of each strain were grown overnight in LB medium with ampicillin in a 3 mL culture at 37° C. The following day, 40 µL of each overnight culture was inoculated into 3 mL fresh LB medium with ampicillin to a final $OD_{600}$~0.05, grown for 3 hours to an $OD_{600}$~0.4, and 0.5 mM isopropyl β-D-1-thiogalactopyranoside (IPTG) was added. Each culture was incubated at 37° C. for an additional 8 hours. To test activity, 0.9 mL of culture was mixed with lysine-HCl (15 mg) and pyridoxal 5-phosphate (PLP) (0.1 mM final concentration) to give a final reaction volume of 1 mL. Each reaction was allowed to proceed at 37° C. for 2 hours. The reaction was stopped by boiling the sample for 5 minutes. Samples were processed immediately using NMR.

TABLE 1

Cadaverine production using strain CIB60 (*E. coli* strain comprising *E. coli* cadA), strain LN18 (*E. coli* strain comprising *K. oxytoca* ldc), and strain LN20 (*E. coli* strain comprising *K. oxytoca* ldc-co1).

| Strain | Plasmid | Enzyme | Gene | Cadaverine (g/kg) |
|---|---|---|---|---|
| N.C. 1 | None | None | None | n.d. |
| N.C. 2 | pUC18 | None | None | n.d. |
| CIB60 | pUC18-CadA | CadA | *E. coli* cadA | 5.69 ± 0.2 |
| LN18 | pUC18-KOldc | *K. oxytoca* Ldc | *K. oxytoca* ldc | 4.41 ± 0.4 |
| LN20 | pUC18-Koldc-co1 | *K. oxytoca* Ldc | *K. oxytoca* ldc-co1 | 6.63 ± 0.2 |

N.C. 1 = negative control of host strain MG1655 K12 without any plasmid.
N.C. 2 = negative control of host strain MG1655 K12 with pUC18 plasmid.
n.d. = not detected As shown in Table 1, cells expressing the *K. oxytoca* Ldc protein encoded by *K. oxytoca* ldc-co1 DNA produced the highest yield of cadaverine (6.63 g/kg) compared to cells expressing the *K. oxytoca* Ldc protein encoded by wild-type *K. oxytoca* ldc DNA (4.41 g/kg) or cells expressing the *E. coli* CadA protein (5.69 g/kg).

Example 2: Cadaverine Production Using the LN20 Strain Comprising *K. Oxytoca* lcd-co1 and a Plac Promoter Three colonies of the LN20 strain comprising *K. oxytoca* ldc-co1 and a Plac promoter (see FIG. 2) were grown overnight in LB medium with ampicillin in a 3 mL culture at 37° C. The following day, 160 µL of each overnight culture was inoculated into 12 mL fresh LB medium with ampicillin to a final $OD_{600}$~0.05, and grown for 3 hours to an $OD_{600}$~0.4. At an $OD_{600}$~0.4, each 12 mL culture was split into four separate 3 mL cultures, and IPTG was added to each culture at the following final concentrations: 0, 0.1, 0.2, and 0.5 mM. Each culture was incubated at 37° C. for additional 8 hours. The same protocol was used as described in Example 1 to test cadaverine production.

TABLE 2

Cadaverine production using strain LN20 (*E. coli* strain comprising *K. oxytoca* ldc-co1 and a Plac promoter)

| IPTG concentration (mM) | Cadaverine (g/kg) |
|---|---|
| 0 | 3.35 ± 0.5 |
| 0.1 | 5.96 ± 0.4 |

TABLE 2-continued

Cadaverine production using strain LN20 (*E. coli* strain comprising *K. oxytoca* ldc-co1 and a Plac promoter)

| IPTG concentration (mM) | Cadaverine (g/kg) |
|---|---|
| 0.2 | 6.68 ± 0.1 |
| 0.5 | 6.82 ± 0.3 |

As shown in Table 2, the highest yield of cadaverine was produced when the LN20 cells (*E. coli* strain comprising *K. oxytoca* ldc-co-1 and a Plac promoter) were induced at an IPTG concentration of 0.5 mM.

Example 3: Cadaverine Production Using the LN22 Strain Comprising *K. Oxytoca* ldc-co1 and a Pbad Promoter Next, a strain was created comprising *K. oxytoca* ldc-co1 and a Pbad promoter (LN22 strain, see FIG. 2). A XhoI restriction site was inserted 27 base pairs upstream of the start of the lac promoter in the plasmid pUC18-KOldc-co1 using the primers XhoI-F and XhoI-R (see FIG. 1). Quick-Change PCR was performed using pUC18-KOldc-co1, the plasmid containing the *K. oxytoca* ldc-co1 gene, as the template DNA. The resulting plasmid containing the inserted XhoI sequence was called pUC18-KOldc-co1-XhoI. The Pbad promoter and the upstream araC gene were amplified from a pKD46 expression plasmid using the primers Pbad-F and Pbad-R (see FIG. 1), and cloned into pUC18-KOldc-co1-XhoI using the restriction enzymes XhoI and SacI to create the plasmid pUC18-KOldc-co1-Pbad. The plasmid pUC18-KOldc-co1-Pbad was transformed into the *E. coli* strain K12 to create the strain LN22 (see FIG. 2). Cadaverine production and analyses experiments were performed in the same way as described in Example 2, except arabinose was added instead of IPTG at the following final concentrations: 0, 2.5 5.0, and 10.0 mM.

TABLE 3

Cadaverine production using strain LN22 (*E. coli* strain comprising *K. oxytoca* ldc-co1 and a Pbad promoter).

| Arabinose concentration (mM) | Cadaverine (g/kg) |
|---|---|
| 0 | 0.49 ± 0.4 |
| 2.5 | 2.35 ± 0.4 |
| 5.0 | 6.09 ± 0.1 |
| 10.0 | 6.45 ± 0.1 |

As shown in Table 3, the highest yield of cadaverine was produced when the LN22 cells (*E. coli* strain comprising *K. oxytoca* ldc-co-1 and a Pbad promoter) were induced at an arabinose concentration of 10 mM.

Example 4: Cadaverine Production Using the LN24 Strain (*E. Coli* Strain Comprising *K. Oxytoca* ldc-co1 and a Ptac Promoter)

Next, a strain was created comprising *K. oxytoca* ldc-co1 and a Ptac promoter (LN24 strain, see FIG. 2). Similarly, the Ptac promoter and upstream lacIq gene were amplified from pGEXT43 using the primers Ptac-F and Ptac-R (see FIG. 1), and cloned into pUC18-KOldc-co1-XhoI to create the plasmid, pUC18-KOldc-co1-Ptac. pUC18-KOldc-co1-Ptac was transformed into K12 to create strain LN24 (see FIG. 2). Cadaverine production and analyses experiments were performed in the same way as described in Example 2.

TABLE 4

Cadaverine production using strain LN24 (*E. coli* strain comprising *K. oxytoca* ldc-co1 and a Ptac promoter)

| IPTG concentration (mM) | Cadaverine (g/kg) |
|---|---|
| 0 | 1.61 ± 0.4 |
| 0.1 | 7.57 ± 0.1 |
| 0.2 | 7.57 ± 0.1 |
| 0.5 | 7.20 ± 0.2 |

As shown in Table 4, the highest yield of cadaverine was produced when the LN24 cells (*E. coli* strain comprising *K. oxytoca* ldc-co-1 and a Ptac promoter) were induced at an IPTG concentration of 0.1 or 0.2 mM.

Example 5: Cadaverine Production Comparing Strains Expressing *K. Oxytoca* Ldc or *E. Coli* CadA During Batch Fermentation Batch fermentation was performed using cells expressing the *K. oxytoca* Ldc protein (strain LN20, *E. coli* cells comprising *K. oxytoca* ldc-co-1 and a Plac promoter, see FIG. 2) and cells expressing the *E. coli* CadA protein (strain CIB60, *E. coli* cells comprising *E. coli* cadA and a Plac promoter, see FIG. 2). Batch cultures were carried out at 37° C. in a 10-L jar fermenter containing 7 L of fermentation medium that consists of 20 g $L^{-1}$ glucose, 30 g $L^{-1}$ corn steeped liquor, 10 g $L^{-1}$ yeast extract, 5 g $L^{-1}$ ammonium sulfate, 10 g $L^{-1}$ MgSO4, 0.05 g $L^{-1}$ FeSO4, 0.05 g $L^{-1}$ MnSO4, 5 g $L^{-1}$ CaCl2, and 0.1 g $L^{-1}$ ampicillin. One colony was inoculated into 50 mL LB medium, and grown for 24 hours at 100 rpm and 37° C. in a shaking incubator. The fermenter was inoculated with 50 mL of the seed culture, and pH was controlled at ~7.0 by adding 20% (w/v) NaOH. The aeration was maintained at 3.5 L $min^{-1}$ with an agitation speed of 400 rpm and a pressure of 0.05 MPa. 0.2 mM IPTG was added at exponential phase. The total fermentation time was 18 hrs. Samples were taken periodically in order to measure the biomass concentration, and the lysine to cadaverine conversion ability. Data are shown in FIG. 3.

Under batch fermentation conditions, cells expressing *E. coli* CadA (strain CIB60) reached a final $OD_{600}$ of 15.02 after 18 hours (see FIG. 3, black squares). Cells expressing *K. oxytoca* Ldc (strain LN20) achieved a lower $OD_{600}$ of 14.26 (see FIG. 3, white squares). The rate of glucose utilization is similar amongst the two strains (see FIG. 3: LN20, white circles; CIB60, black circles). However, the cells expressing *K. oxytoca* Ldc (strain LN20) were able to convert lysine-HCl to cadaverine at a rate of 0.43% $min^{-1}$, which is 24% higher when compared to the cells expressing *E. coli* CadA (strain CIB60), which had an activity of 0.37% $min^{-1}$ (see FIG. 3, white triangles and black triangles, respectively).

Example 6: Cadaverine Production Using Strain Expressing *K. Oxytoca* Ldc During Fed-Batch Fermentation Fed-batch fermentation was performed using cells expressing the *K. oxytoca* Ldc protein (strain LN24, *E. coli* cells comprising *K. oxytoca* ldc-co-1 and a Ptac promoter, see FIG. 2). Fed-batch cultivation was carried out at 37° C. in a 10-L jar fermenter containing 5 L of fermentation medium that consists of 8 g $L^{-1}$ glucose, 30 g $L^{-1}$ corn steeped liquor, 10 g $L^{-1}$ yeast extract, 5 g $L^{-1}$ ammonium sulfate, 10 g $L^{-1}$ MgSO4, 0.05 g $L^{-1}$ FeSO4, 0.05 g $L^{-1}$ MnSO4, 5 g $L^{-1}$ CaCl2, and 0.1 g $L^{-1}$ ampicillin. The feeding solution contained 50% glucose in water in order to keep the glucose concentration in the fermentation broth at 5-8 g $L^{-1}$. A 25% ammonia solution was added to maintain the pH at ~7.0. The aeration was maintained at 3.5 L $min^{-1}$ with an agitation speed of 400 rpm and a pressure of 0.05 MPa. 0.1 mM IPTG was added every 10 hours during exponential phase. The total fermentation time was 58 hours. Samples were taken periodically over the 58 hours in order to measure the biomass concentration, and the lysine to cadaverine conversion ability. Data are shown in FIG. 4.

Figure 4:
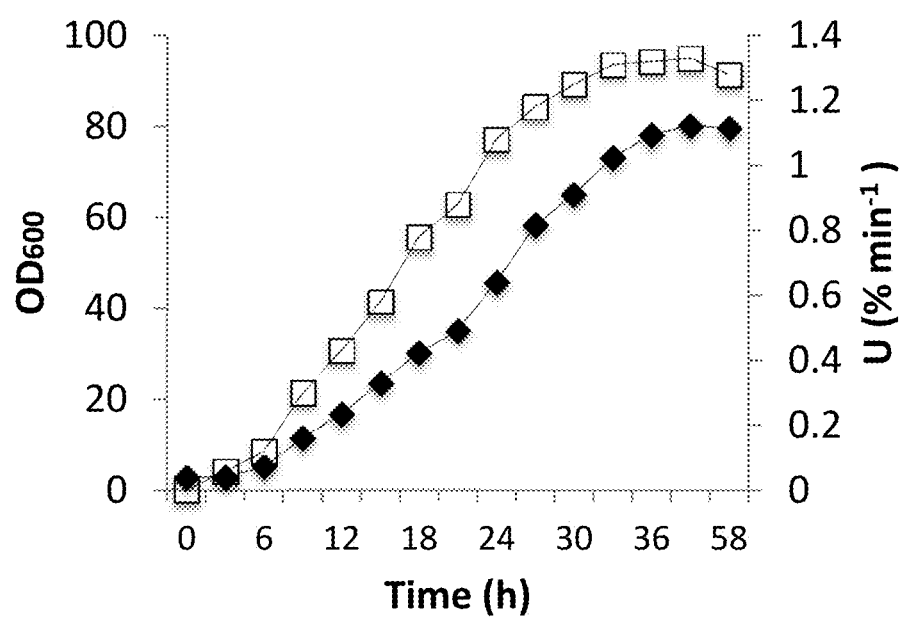
FIG. 4: Fed batch fermentation results. Strain LN24 was grown in a fed batch fermentation, and the culture was assayed for its ability to convert lysine-HCl to cadaverine. At each time point, samples were taken to measure $OD_{600}$ (white square), and activity (black diamond).

Under fed-batch fermentation conditions, cells expressing *K. oxytoca* Ldc protein (strain LN24) reached an $OD_{600}$ of ~80 after 58 hours (see FIG. 4, white squares), and maximum activity of 1.33% $min^{-1}$ was observed for the 10 g sample assayed (0.133% $min^{-1}$ $g^{-1}$) (see FIG. 4, black diamonds).

Example 7: Screening a Ribosomal Binding Site Library for Increased Cadaverine Production A ribosomal binding site (RBS) DNA library was prepared to use for screening for an optimal RBS sequence for *K. oxytoca* Ldc protein expression that results in increased cadaverine production. The primers RBS-F and RBS-R (see FIG. 1) were used to modify the nucleotides in the RBS DNA region of *K. oxytoca* ldc-co1 (SEQ ID NO: 3) in pUC18-KOldc-co1-Ptac. RBS-F was designed to allow for random nucleotide sequences to be generated at nucleotide positions −7 to −12 relative to the first nucleotide of *K. oxytoca* ldc-co1. Five PCR reactions were pooled together, treated with the restriction enzyme Dpnl in order to remove any template DNA, and PCR clean-up was performed. One μg of purified DNA was transformed into *E. coli* MG1655 K12, and the transformation was plated to allow for single colonies to be screened. One thousand colonies were screened and were labeled LN100-1099. Cadaverine production using strains LN100-1099 was compared to that from LN24 (*E. coli* strain comprising *K. oxytoca* ldc-co1 and Ptac, see FIG. 2).

Five strains obtained from the screening library (LN140, LN301, LN499, LN637, and LN770) demonstrated the highest cadaverine production out of the one thousand strains screened. The plasmids from these strains were purified and labeled pLN140, pLN301, pLN499, pLN637, and pLN770. The plasmids were sequenced using the primer RBS-out-F (see FIG. 1) to determine the novel RBS DNA sequences in the RBS DNA region of *K. oxytoca* ldc-co-1. The five plasmids from the top five producers were transformed into *E. coli* MG1655 K12 to produce strains LN1100, LN1101, LN1102, LN1103, and LN1104 (see FIG. 2). Cadaverine production using the strains with mutated RBS DNA sequences (LN1100, LN1101, LN1102, LN1103, and LN1104) was compared to cadaverine production using the strain with the wild-type RBS DNA sequence (strain LN24, *E. coli* strain comprising *K. oxytoca* ldc-co1 and a Ptac promoter, FIG. 2). Cadaverine production and analysis was performed as described in Example 1, except 0.1 mM IPTG and 25 mg lysine-HCl was used.

TABLE 5

Cadaverine production using strain LN24 and strains obtained from the RBS DNA screening library.

| Strain | Plasmid | Cadaverine (g/kg) | RBS DNA Sequence | Name and SEQ ID NO: |
|---|---|---|---|---|
| LN24 | pUC18-KOldc-c01-Ptac | 7.45 ± 0.2 | GGAGAT | RBS DNA-1 (SEQ ID NO: 14) |
| LN1100 | pLN140 | 8.26 ± 0.8 | AGGACT | RBS DNA-2 (SEQ ID NO: 15) |
| LN1101 | pLN301 | 9.0 ± 0.5 | GAGGAG | RBS DNA-3 (SEQ ID NO: 16) |
| LN1102 | pLN499 | 8.7 ± 0.4 | GAGGAA | RBS DNA-4 (SEQ ID NO: 17) |
| LN1103 | pLN637 | 10.0 ± 0.6 | TGGAGG | RBS DNA-5 (SEQ ID NO: 18) |
| LN1104 | pLN770 | 8.8 ± 0.6 | CAGGAG | RBS DNA-6 (SEQ ID NO: 19) |

As shown in Table 5, the plasmids with the mutated RBS DNA sequences when transformed into *E. coli* K12 (LN1100, LN1101, LN1102, LN1103, and LN1104) produced higher yields of cadaverine when compared to the strain with the wild-type RBS DNA sequence (LN24). The highest yield of cadaverine was produced from strain LN1103 (i.e., 10.0±0.6 g/kg), which had the RBS DNA-5 sequence (i.e., TGGAGG; SEQ ID NO: 18).

Example 8: Screening epPCR Library for Increased Cadaverine Production

The plasmid from the strain that produced the highest yield of cadaverine in Example 7 (plasmid pLN637, strain LN1103) was used for introducing random mutations into the *K. oxytoca* ldc-co-1 polynucleotide sequence (SEQ ID NO: 3) using error-prone PCR (epPCR). Based on the sequencing result of pLN637, the primer epPCR-F (see FIG. 1) was designed to amplify the region upstream *K. oxytoca* ldc-co-1. The primers epPCR-F and epPCR-R (FIG. 1) were used to amplify the *K. oxytoca* ldc-co1 sequence from pLN637 using epPCR. epPCR was accomplished with the GeneMorph II Random Mutagenesis Kit by following the manufacturer's instructions. Five PCR reactions were pooled together, treated with the restriction enzyme DpnI in order to remove any template DNA, and purified. The amplified product was cloned into pUC18-KOldc-co1-Ptac to replace the *K. oxytoca* ldc-co1 polynucleotide sequence using the restriction enzymes SacI and XbaI. The purified DNA was transformed into *E. coli* MG1655 K12, and the transformation was plated to allow for single colonies to be screened for increased cadaverine production. One thousand single colonies from the transformation were screened in order to identify strains with the increased ability to convert lysine-HCl to cadaverine compared to LN1103. These one thousand mutants generated from epPCR were labeled LN2000-2999.

Five strains obtained from epPCR (i.e., LN2377, LN2453, LN2768, LN2888, and LN2964) demonstrated the highest cadaverine production out of the one thousand mutants generated by epPCR that were screened. The plasmids from these strains were purified, and labeled pLN2377, pLN2453, pLN2768, pLN2888, and pLN2964. The lysine decarboxylase gene on each of these plasmids was sequenced using the primers ldc-out-F and ldc-out-R (FIG. 1). The five plasmids were transformed into *E. coli* MG1655 K12 to produce strains LN3010, LN3011, LN3012, LN3013, and LN3014 (FIG. 2). Cadaverine production and analysis was performed as described Example 7.

TABLE 6

Cadaverine production using strain LN1103 and strains obtained from the epPCR screening library.

| Strain | *K. oxytoca* Ldc Protein mutation | *K. oxytoca* ldc-co1 Gene mutation | RBS DNA sequence | Cadaverine (g/kg) |
|---|---|---|---|---|
| LN1103 | No mutation (SEQ ID NO: 2) | No mutation (SEQ ID NO: 3) | TGGAGG | 9.29 ± 1.0 |
| LN3010 | K287E (SEQ ID NO: 5) | A859G (SEQ ID NO: 4) | TGGAGG | 9.62 ± 0.4 |
| LN3011 | R436G (SEQ ID NO: 9) | C1306G (SEQ ID NO: 8) | TGGAGG | 10.0 ± 0.9 |
| LN3012 | F607Y (SEQ ID NO: 13) | T1820A (SEQ ID NO: 12) | TGGAGG | 9.74 ± 0.6 |

TABLE 6-continued

Cadaverine production using strain LN1103 and strains obtained from the epPCR screening library.

| Strain | K. oxytoca Ldc Protein mutation | K. oxytoca ldc-co1 Gene mutation | RBS DNA sequence | Cadaverine (g/kg) |
|---|---|---|---|---|
| LN3013 | T398S (SEQ ID NO: 7) | C1193G (SEQ ID NO: 6) | TGGAGG | 10.7 ± 0.3 |
| LN3014 | F507L (SEQ ID NO: 11) | C1521G (SEQ ID NO: 10) | TGGAGG | 11.2 ± 1.0 |

As shown in Table 6, *E. coli* K12 transformed with the plasmids that have mutations in the sequence of *K. oxytoca* ldc-co1 (i.e., strain LN3010, LN3011, LN3012, LN3013, and LN3014) led to higher yields of cadaverine when compared to the strain with no mutations in the sequence of *K. oxytoca* ldc-co-1 (i.e., strain LN24). The highest yield of cadaverine was produced from strain LN3014, the strain expressing the mutant *K. oxytoca* Ldc F507L protein (SEQ ID NO: 11), which resulted in a yield of 11.2±1.0 g/kg cadaverine.

Figure 5:
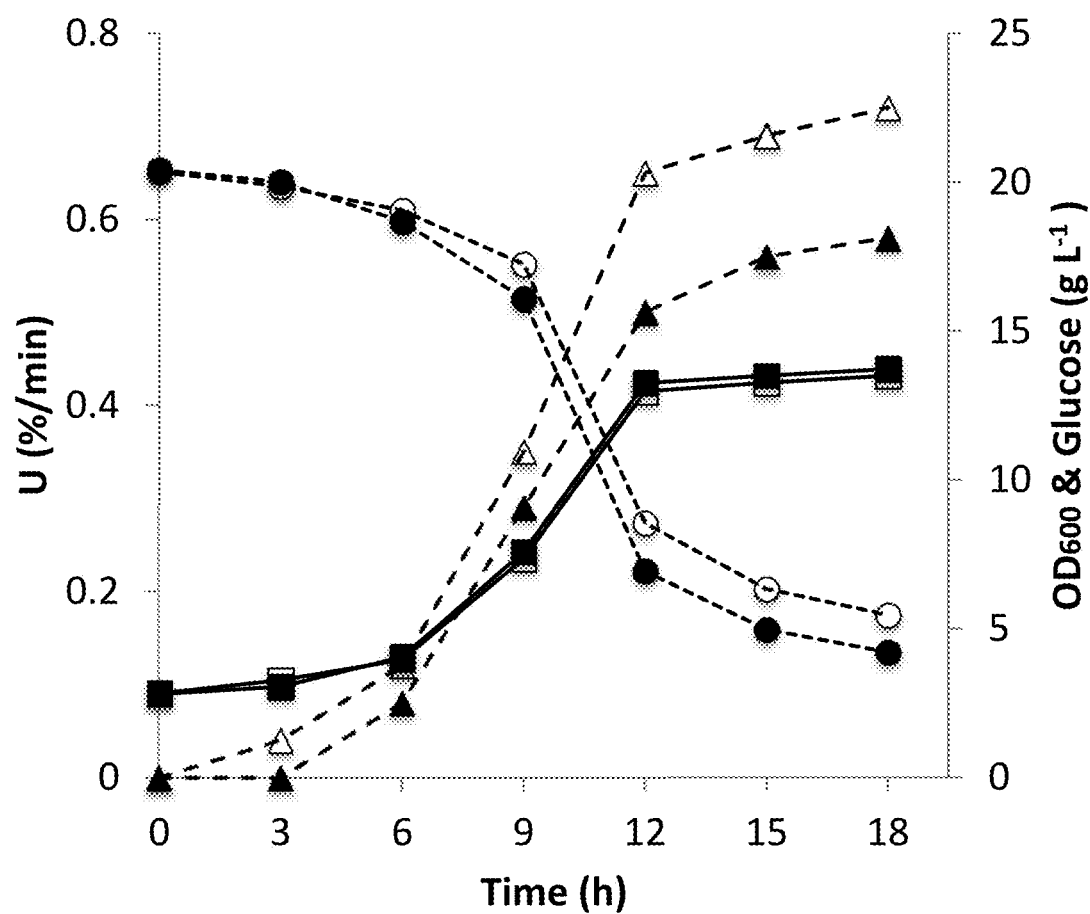
FIG. 5: Batch fermentation results. LN24 (black) and LN3014 (white) were grown using batch fermentation, and the cultures were assayed for their ability to convert lysine-HCl to cadaverine. At each time point, samples were taken to measure $OD_{600}$ (square), glucose (circle), and activity (triangle).

Example 9: Cadaverine Production Comparing Strains Expressing *K. Oxytoca* Ldc or *K. Oxytoca* Ldc F507L During Batch Fermentation Batch fermentation of cells expressing either *K. oxytoca* Ldc (strain LN24, FIG. 2) or cells expressing *K. oxytoca* Ldc F507L (strain LN3014, FIG. 2) was performed in the same way as described in Example 5. Data are shown in FIG. 5. Under batch fermentation conditions, cells expressing *K. oxytoca* Ldc (strain LN24) and cells expressing *K. oxytoca* Ldc F507L (strain LN3014) reached a similar final $OD_{600}$ of around 13.6±0.1 after 18 hours (see FIG. 5, black squares and white squares, respectively). The rate of glucose utilization is slightly higher in cells expressing *K. oxytoca* Ldc (strain LN24) compared to cells expressing *K. oxytoca* Ldc F507L (strain LN3014) (see FIG. 5, black circles and white circles, respectively). However, the cells expressing *K. oxytoca* Ldc F507L (strain LN3014) had a 25% higher rate of lysine-HCl to cadaverine conversion compared to cells expressing *K. oxytoca* Ldc (strain LN24) (see FIG. 5, white triangles and black triangles, respectively). Cells expressing *K. oxytoca* Ldc (strain LN24) achieved an activity of 0.58% min-1, while cells expressing *K. oxytoca* Ldc F507L (strain LN3014) achieved an activity of 0.72% min-1 (see FIG. 5 at the 18 hour time point, black triangles and white triangles, respectively).

Figure 6:
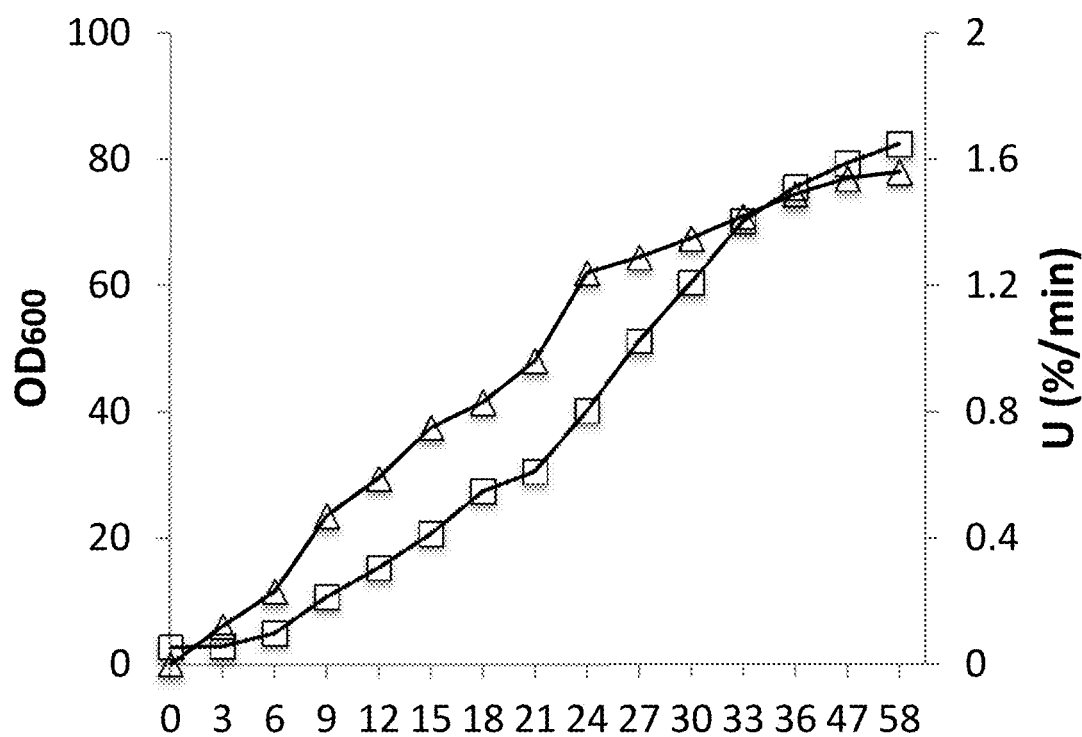
FIG. 6: Fed batch fermentation results. Strain LN3014 was grown in a fed batch fermentation, and the culture was assayed for its ability to convert lysine-HCl to cadaverine. At each time point, samples were taken to measure $OD_{600}$ (white square), and activity (white triangle).

Example 10: Cadaverine Production of Strain Expressing *K. Oxytoca* Ldc F507L During Fed-Batch Fermentation Fed-batch fermentation of cells expressing *K. oxytoca* Ldc F507L (strain LN3014, FIG. 2) was performed in the same way as provided in Example 6. Data are shown in FIG. 6. Cells expressing *K. oxytoca* Ldc F507L (strain LN3014) were tested in fed-batch fermentation for 58 hours. The $OD_{600}$ reached~82 after 58 hours, and maximum activity of 1.56% min-1 was observed for the 10 g sample assayed (0.156% min-1 g-1) (see FIG. 6, square and triangle, respectively, at 58 hour time point).

REFERENCES

The references, patents and published patent applications listed below, and all references cited in the specification above are hereby incorporated by reference in their entirety, as if fully set forth herein.
1. Wertz et al. Chimeric nature of two plasm ids of *H. alvei* encoding the bacteriocins alveicins A and B. Journal of Bacteriology, (2004) 186: 1598-1605.
2. Datsenko K A & Wanner B L. One-step inactivation of chromosomal genes in *Escherichia coli* K-12 using PCR products. PNAS, (2000) 6640-6645.
3. Papadakis et al. Promoters and Control Elements: Designing Expression Cassettes for Gene Therapy. Current Gene Therapy, (2004) 4: 89-113.

```
SEQUENCE LISTING
(K. oxytoca ldc nucleotide sequence)
                                                          SEQ ID NO: 1
ATGAACGTTATCGCAATCATGAATCACATGGGTGTCTACTTCAAAGAAGAACCCAT

CCGTGAACTGCATCGCGCCCTCGAACGCCTGGACTTCCGTATTGTCTACCCGAAC

GACCGTGAAGACTTATTAAAACTTATCGAAAACAATGCGCGTCTGTGCGGCGTGAT

CTTCGACTGGGATAAATATAATCTCGAACTGTGCGAAGACATCAGCAAAATGAACG

AATACATGCCGCTGTACGCCTTTGCGAACACTTACTCAACGCTGGACGTGAGCCTC

AACGATCTGCGGATGCAGGTTCGCTTCTTCGAATATGCGCTGGGCGCAGCGGAAG

ACATTGCCAACAAAATCAAACAGAATACCGACGAGTATATCGACACCATTCTGCCG

CCGCTGACCAAAGCGCTGTTTAAATACGTGCGTGAAGGCAAATACACCTTCTGTAC

CCCAGGCCATATGGGCGGTACCGCGTTCCAGAAAAGCCCAGTCGGCAGCATCTTC

TACGATTTCTTTGGTTCCAATACCATGAAATCCGATATCTCGATTTCGGTTTCTGAA
```

```
CTCGGTTCTCTGCTGGACCACAGCGGCCCGCACAAAGAAGCGGAAGAGTACATCG
CCCGCGTCTTCAACGCGGAACGCAGCTACATGGTGACCAACGGGACCTCTACCGC
CAACAAAATTGTCGGCATGTATTCCGCCCCGGCCGGTAGCACCGTGCTGATTGAC
CGTAACTGCCATAAATCGCTGACCCATCTGATGATGATGAGCGACATTACGCCAAT
CTACTTCCGCCCGACCCGCAACGCCTACGGTATCCTCGGCGGTATCCCGCAGAGC
GAATTCCAGCATGCGACCATCGCGAAGCGCGTGAAAGAAACCCCGAACGCGACCT
GGCCGGTGCACGCGGTTATCACCAACTCCACCTATGACGGTCTGCTGTACAACAC
GGACTACATCAAGAAAACCCTGGATGTGAAATCCATCCACTTTGACTCCGCGTGGG
TGCCTTACACCAACTTCTCGCCGATTTATGAAGGCAAATGCGGGATGAGCGGCGG
CCGCGTCGAAGGGAAAGTGATTTACGAAACCCAGTCCACGCACAAACTGCTGGCG
GCGTTCTCTCAGGCCTCGATGATTCACGTTAAAGGCGACGTGAACGAAGAGACCT
TTAACGAAGCCTACATGATGCACACCACCACTTCTCCGCACTACGGCGTGGTGGC
CTCGACGGAAACCGCGGCGGCGATGATGAAAGGCAACGCCGGTAAGCGCCTGAT
TGACGGCTCTATCGAACGTTCAATCAAGTTCCGTAAAGAGATCAAACGTCTGAAAG
GCGAGTCCGACGGCTGGTTCTTCGACGTCTGGCAGCCGGAACATATCGATGGCG
CTGAATGCTGGCCGCTGCGCTCCGACAGCGCGTGGCACGGCTTCAAAAACATCGA
TAACGAGCACATGTATCTCGACCCGATTAAAGTCACGCTGCTGACTCCGGGGATG
AAGAAAGACGGCACCATGGATGAGTTCGGTATTCCGGCGAGCATCGTGGCGAAGT
ATCTCGACGAGCACGGTATCGTGGTCGAAAAAACCGGTCCGTACAACCTGCTGTT
CCTGTTCAGTATCGGTATCGACAAAACCAAAGCGCTGAGCCTGCTGCGTGCGCTG
ACCGATTTCAAACGCGCGTTCGACCTGAACCTGCGGGTGAAAAACATGCTGCCGT
CGCTGTATCGTGAAGATCCGGAATTCTACGAAAACATGCGCGTTCAGGAACTGGC
GCAGAACATTCATAAACTGATTGAGCACCACAACCTGCCGGATCTGATGTTCCGCG
CGTTCGAAGTGCTGCCGACCATGATGATCACGCCGTACGCCGCGTTCCAGAAAGA
GCTGCACGGTCAGACCGAAGAGGTGTATCTCGAAGAGATGGTGGGCCGCGTCAA
CGCCAATATGATCCTGCCGTATCCTCCGGGAGTGCCGCTGGTGATGCCGGGTGAA
ATGATCACCGAAGAGAGCCGTCCGGTGCTGGAGTTCCTGCAGATGCTGTGCGAAA
TCGGCGCCCACTATCCGGGCTTCGAAACCGATATCCACGGCGCCTATCGTCAGGC
GGATGGTCGTTACACCGTTAAAGTGCTGAAAGAAGAAAATAACAAATAA
```
(K. oxytoca Ldc amino acid sequence) SEQ ID NO: 2

MNVIAIMNHMGVYFKEEPIRELHRALERLDFRIVYPNDREDLLKLIENNA
RLCGVIFDWDKYNLELCEDISKMNEYMPLYAFANTYSTLDVSLNDLRMQV
RFFEYALGAAEDIANKIKQNTDEYIDTILPPLTKALFKYVREGKYTFCTP
GHMGGTAFQKSPVGSIFYDFFGSNTMKSDISISVSELGSLLDHSGPHKEA
EEYIARVFNAERSYMVTNGTSTANKIVGMYSAPAGSTVLIDRNCHKSLTH
LMMMSDITPIYFRPTRNAYGILGGIPQSEFQHATIAKRVKETPNATWPVH
AVITNSTYDGLLYNTDYIKKTLDVKSIHFDSAWVPYTNFSPIYEGKCGMS
GGRVEGKVIYETQSTHKLLAAFSQASMIHVKGDVNEETFNEAYMMHTTTS
PHYGVVASTETAAAMMKGNAGKRLIDGSIERSIKFRKEIKRLKGESDGWF
FDVWQPEHIDGAECWPLRSDSAWHGFKNIDNEHMYLDPIKVTLLTPGMKK

-continued

DGTMDEFGIPASIVAKYLDEHGIVVEKTGPYNLLFLFSIGIDKTKALSLL

RALTDFKRAFDLNLRVKNMLPSLYREDPEFYENMRVQELAQNIHKLIEHH

NLPDLMFRAFEVLPTMMITPYAAFQKELHGQTEEVYLEEMVGRVNANMIL

PYPPGVPLVMPGEMITEESRPVLEFLQMLCEIGAHYPGFETDIHGAYRQA

DGRYTVKVLKEENNK (K. oxytoca ldc-co1 nucleotide sequence)

SEQ ID NO: 3

ATGAATGTTATTGCGATTATGAACCACATGGGCGTATACTTCAAGGAGGAACCGAT

CCGCGAACTGCATCGTGCCCTGGAACGTCTGGATTTCCGCATCGTCTATCCAAATG

ACCGTGAGGATCTCCTCAAGCTCATCGAGAATAATGCGCGCCTGTGTGGTGTTATC

TTTGACTGGGACAAATACAATCTGGAACTGTGCGAGGACATCTCTAAGATGAACGA

ATATATGCCGCTGTACGCGTTTGCCAACACCTACTCTACCCTCGACGTTAGCCTGA

ATGACCTGCGCATGCAGGTTCGTTTCTTTGAATACGCGCTGGGTGCGGCGGAAGA

CATTGCAAACAAGATCAAACAAAACACCGACGAGTACATTGATACGATCCTCCCTC

CTCTCACCAAAGCTCTGTTCAAGTACGTCCGCGAGGGCAAGTACACTTTTTGCACC

CCTGGTCATATGGGCGGCACTGCGTTTCAGAAAAGCCCGGTTGGTTCCATTTTCTA

TGACTTTTTTGGTTCTAATACGATGAAATCTGATATCTCTATCTCTGTTTCCGAACTC

GGCTCCCTGCTGGACCACTCTGGTCCGCATAAAGAAGCAGAAGAATACATCGCGC

GTGTTTTCAACGCGGAACGCTCTTACATGGTAACGAACGGCACCAGCACCGCGAA

TAAGATTGTTGGTATGTATAGCGCTCCAGCGGGCTCTACCGTACTCATTGACCGTA

ACTGCCATAAAAGCCTGACTCACCTCATGATGATGTCCGACATCACTCCAATTTACT

TCCGTCCGACCCGTAATGCCTATGGCATCCTGGGTGGCATTCCTCAGTCTGAATTT

CAACACGCCACTATTGCTAAGCGTGTAAAGGAGACTCCAAACGCTACGTGGCCTG

TCCACGCCGTTATCACCAACTCCACCTACGACGGTCTCCTGTACAATACTGATTAC

ATCAAAAAAACCCTGGATGTAAAATCCATTCACTTCGATAGCGCATGGGTTCCTTAC

ACTAACTTCAGCCCAATCTATGAGGGTAAGTGCGGTATGAGCGGTGGTCGTGTCG

AAGGCAAAGTTATCTACGAGACGCAAAGCACTCACAAACTCCTGGCAGCGTTCTCT

CAAGCGTCCATGATTCATGTTAAGGGTGACGTGAATGAAGAGACCTTCAACGAAGC

GTACATGATGCATACCACCACCTCTCCGCACTACGGTGTCGTTGCGTCCACGGAA

ACGGCGGCTGCTATGATGAAAGGTAATGCGGGTAAACGCCTGATCGACGGTTCTA

TTGAGCGTAGCATCAAATTTCGTAAAGAAATCAAACGTCTCAAAGGTGAAAGCGAC

GGCTGGTTTTTCGATGTGTGGCAGCCAGAACATATTGATGGTGCTGAATGCTGGC

CGCTGCGTTCTGACTCCGCTTGGCACGGTTTCAAAAACATCGACAATGAACACATG

TACCTGGACCCGATCAAGGTTACGCTCCTGACCCCAGGTATGAAAAAAGACGGTA

CTATGGATGAATTCGGTATTCCGGCCTCCATCGTGGCGAAGTATCTCGACGAACAT

GGCATTGTTGTGGAGAAGACGGGTCCGTATAACCTGCTGTTTCTGTTTTCCATCGG

CATTGACAAAACGAAAGCGCTGTCTCTGCTGCGTGCGCTGACCGACTTTAAACGT

GCGTTCGACCTGAATCTCCGTGTTAAGAACATGCTCCCGTCTCTGTACCGTGAAGA

CCCGGAATTCTACGAAAACATGCGTGTTCAGGAACTGGCGCAGAATATCCACAAG

CTGATTGAGCATCACAACCTCCCGGATCTCATGTTCCGTGCCTTTGAAGTTCTCCC

AACGATGATGATTACTCCGTATGCGGCGTTCCAAAAAGAGCTGCATGGCCAAACG

GAAGAGGTGTACCTCGAAGAAATGGTCGGTCGCGTTAATGCTAATATGATTCTCCC

-continued

```
GTATCCACCTGGTGTGCCTCTCGTTATGCCAGGCGAAATGATCACTGAAGAGTCCC
GCCCAGTGCTCGAATTTCTGCAAATGCTGTGTGAAATTGGCGCCCACTACCCAGG
CTTCGAAACCGATATTCATGGCGCTTACCGCCAAGCAGATGGTCGCTACACGGTTA
AAGTACTCAAGGAAGAGAACAACAAATAA
```

(*K. oxytoca* ldc-co1 A859G nucleotide sequence)

SEQ ID NO: 4

```
ATGAATGTTATTGCGATTATGAACCACATGGGCGTATACTTCAAGGAGGAACCGAT
CCGCGAACTGCATCGTGCCCTGGAACGTCTGGATTTCCGCATCGTCTATCCAAATG
ACCGTGAGGATCTCCTCAAGCTCATCGAGAATAATGCGCGCCTGTGTGGTGTTATC
TTTGACTGGGACAAATACAATCTGGAACTGTGCGAGGACATCTCTAAGATGAACGA
ATATATGCCGCTGTACGCGTTTGCCAACACCTACTCTACCCTCGACGTTAGCCTGA
ATGACCTGCGCATGCAGGTTCGTTTCTTTGAATACGCGCTGGGTGCGGCGGAAGA
CATTGCAAACAAGATCAAACAAAACACCGACGAGTACATTGATACGATCCTCCCTC
CTCTCACCAAAGCTCTGTTCAAGTACGTCCGCGAGGGCAAGTACACTTTTTGCACC
CCTGGTCATATGGGCGGCACTGCGTTTCAGAAAAGCCCGGTTGGTTCCATTTTCTA
TGACTTTTTTGGTTCTAATACGATGAAATCTGATATCTCTATCTCTGTTTCCGAACTC
GGCTCCCTGCTGGACCACTCTGGTCCGCATAAAGAAGCAGAAGAATACATCGCGC
GTGTTTTCAACGCGGAACGCTCTTACATGGTAACGAACGGCACCAGCACCGCGAA
TAAGATTGTTGGTATGTATAGCGCTCCAGCGGGCTCTACCGTACTCATTGACCGTA
ACTGCCATAAAAGCCTGACTCACCTCATGATGATGTCCGACATCACTCCAATTTACT
TCCGTCCGACCCGTAATGCCTATGGCATCCTGGGTGGCATTCCTCAGTCTGAATTT
CAACACGCCACTATTGCTGAGCGTGTAAAGGAGACTCCAAACGCTACGTGGCCTG
TCCACGCCGTTATCACCAACTCCACCTACGACGGTCTCCTGTACAATACTGATTAC
ATCAAAAAAACCCTGGATGTAAAATCCATTCACTTCGATAGCGCATGGGTTCCTTAC
ACTAACTTCAGCCCAATCTATGAGGGTAAGTGCGGTATGAGCGGTGGTCGTGTCG
AAGGCAAAGTTATCTACGAGACGCAAAGCACTCACAAACTCCTGGCAGCGTTCTCT
CAAGCGTCCATGATTCATGTTAAGGGTGACGTGAATGAAGAGACCTTCAACGAAGC
GTACATGATGCATACCACCACCTCTCCGCACTACGGTGTCGTTGCGTCCACGGAA
ACGGCGGCTGCTATGATGAAAGGTAATGCGGGTAAACGCCTGATCGACGGTTCTA
TTGAGCGTAGCATCAAATTTCGTAAAGAAATCAAACGTCTCAAAGGTGAAAGCGAC
GGCTGGTTTTTCGATGTGTGGCAGCCAGAACATATTGATGGTGCTGAATGCTGGC
CGCTGCGTTCTGACTCCGCTTGGCACGGTTTCAAAAACATCGACAATGAACACATG
TACCTGGACCCGATCAAGGTTACGCTCCTGACCCCAGGTATGAAAAAGACGGTA
CTATGGATGAATTCGGTATTCCGGCCTCCATCGTGGCGAAGTATCTCGACGAACAT
GGCATTGTTGTGGAGAAGACGGGTCCGTATAACCTGCTGTTTCTGTTTTCCATCGG
CATTGACAAAACGAAAGCGCTGTCTCTGCTGCGTGCGCTGACCGACTTTAAACGT
GCGTTCGACCTGAATCTCCGTGTTAAGAACATGCTCCCGTCTCTGTACCGTGAAGA
CCCGGAATTCTACGAAAACATGCGTGTTCAGGAACTGGCGCAGAATATCCACAAG
CTGATTGAGCATCACAACCTCCCGGATCTCATGTTCCGTGCCTTTGAAGTTCTCCC
AACGATGATGATTACTCCGTATGCGGCGTTCCAAAAAGAGCTGCATGGCCAAACG
GAAGAGGTGTACCTCGAAGAAATGGTCGGTCGCGTTAATGCTAATATGATTCTCCC
```

```
GTATCCACCTGGTGTGCCTCTCGTTATGCCAGGCGAAATGATCACTGAAGAGTCCC

GCCCAGTGCTCGAATTTCTGCAAATGCTGTGTGAAATTGGCGCCCACTACCCAGG

CTTCGAAACCGATATTCATGGCGCTTACCGCCAAGCAGATGGTCGCTACACGGTTA

AAGTACTCAAGGAAGAGAACAACAAATAA
```

(K. oxytoca Ldc K287E amino acid sequence)         SEQ ID NO: 5

```
MNVIAIMNHMGVYFKEEPIRELHRALERLDFRIVYPNDREDLLKLIENNA

RLCGVIFDWDKYNLELCEDISKMNEYMPLYAFANTYSTLDVSLNDLRMQV

RFFEYALGAAEDIANKIKQNTDEYIDTILPPLTKALFKYVREGKYTFCTP

GHMGGTAFQKSPVGSIFYDFFGSNTMKSDISISVSELGSLLDHSGPHKEA

EEYIARVFNAERSYMVTNGTSTANKIVGMYSAPAGSTVLIDRNCHKSLTH

LMMMSDITPIYFRPTRNAYGILGGIPQSEFQHATIAERVKETPNATWPVH

AVITNSTYDGLLYNTDYIKKTLDVKSIHFDSAWVPYTNFSPIYEGKCGMS

GGRVEGKVIYETQSTHKLLAAFSQASMIHVKGDVNEETFNEAYMMHTTTS

PHYGVVASTETAAAMMKGNAGKRLIDGSIERSIKFRKEIKRLKGESDGWF

FDVWQPEHIDGAECWPLRSDSAWHGFKNIDNEHMYLDPIKVTLLTPGMKK

DGTMDEFGIPASIVAKYLDEHGIVVEKTGPYNLLFLFSIGIDKTKALSLL

RALTDFKRAFDLNLRVKNMLPSLYREDPEFYENMRVQELAQNIHKLIEHH

NLPDLMFRAFEVLPTMMITPYAAFQKELHGQTEEVYLEEMVGRVNANMIL

PYPPGVPLVMPGEMITEESRPVLEFLQMLCEIGAHYPGFETDIHGAYRQA

DGRYTVKVLKEENNK
```

(K. oxytoca ldc-co1 C1193G nucleotide sequence)         SEQ ID NO: 6

```
ATGAATGTTATTGCGATTATGAACCACATGGGCGTATACTTCAAGGAGGAACCGAT

CCGCGAACTGCATCGTGCCCTGGAACGTCTGGATTTCCGCATCGTCTATCCAAATG

ACCGTGAGGATCTCCTCAAGCTCATCGAGAATAATGCGCGCCTGTGTGGTGTTATC

TTTGACTGGGACAAATACAATCTGGAACTGTGCGAGGACATCTCTAAGATGAACGA

ATATATGCCGCTGTACGCGTTTGCCAACACCTACTCTACCCTCGACGTTAGCCTGA

ATGACCTGCGCATGCAGGTTCGTTTCTTTGAATACGCGCTGGGTGCGGCGGAAGA

CATTGCAAACAAGATCAAACAAAACACCGACGAGTACATTGATACGATCCTCCCTC

CTCTCACCAAAGCTCTGTTCAAGTACGTCCGCGAGGGCAAGTACACTTTTTGCACC

CCTGGTCATATGGGCGGCACTGCGTTTCAGAAAAGCCCGGTTGGTTCCATTTTCTA

TGACTTTTTTGGTTCTAATACGATGAAATCTGATATCTCTATCTCTGTTTCCGAACTC

GGCTCCCTGCTGGACCACTCTGGTCCGCATAAAGAAGCAGAAGAATACATCGCGC

GTGTTTTCAACGCGGAACGCTCTTACATGGTAACGAACGGCACCAGCACCGCGAA

TAAGATTGTTGGTATGTATAGCGCTCCAGCGGGCTCTACCGTACTCATTGACCGTA

ACTGCCATAAAAGCCTGACTCACCTCATGATGATGTCCGACATCACTCCAATTTACT

TCCGTCCGACCCGTAATGCCTATGGCATCCTGGGTGGCATTCCTCAGTCTGAATTT

CAACACGCCACTATTGCTAAGCGTGTAAAGGAGACTCCAAACGCTACGTGGCCTG

TCCACGCCGTTATCACCAACTCCACCTACGACGGTCTCCTGTACAATACTGATTAC

ATCAAAAAAACCCTGGATGTAAAATCCATTCACTTCGATAGCGCATGGGTTCCTTAC

ACTAACTTCAGCCCAATCTATGAGGGTAAGTGCGGTATGAGCGGTGGTCGTGTCG

AAGGCAAAGTTATCTACGAGACGCAAAGCACTCACAAACTCCTGGCAGCGTTCTCT
```

```
CAAGCGTCCATGATTCATGTTAAGGGTGACGTGAATGAAGAGACCTTCAACGAAGC
GTACATGATGCATACCAGCACCTCTCCGCACTACGGTGTCGTTGCGTCCACGGAA
ACGGCGGCTGCTATGATGAAAGGTAATGCGGGTAAACGCCTGATCGACGGTTCTA
TTGAGCGTAGCATCAAATTTCGTAAAGAAATCAAACGTCTCAAAGGTGAAAGCGAC
GGCTGGTTTTTCGATGTGTGGCAGCCAGAACATATTGATGGTGCTGAATGCTGGC
CGCTGCGTTCTGACTCCGCTTGGCACGGTTTCAAAAACATCGACAATGAACACATG
TACCTGGACCCGATCAAGGTTACGCTCCTGACCCCAGGTATGAAAAAAGACGGTA
CTATGGATGAATTCGGTATTCCGGCCTCCATCGTGGCGAAGTATCTCGACGAACAT
GGCATTGTTGTGGAGAAGACGGGTCCGTATAACCTGCTGTTTCTGTTTTCCATCGG
CATTGACAAAACGAAAGCGCTGTCTCTGCTGCGTGCGCTGACCGACTTTAAACGT
GCGTTCGACCTGAATCTCCGTGTTAAGAACATGCTCCCGTCTCTGTACCGTGAAGA
CCCGGAATTCTACGAAAACATGCGTGTTCAGGAACTGGCGCAGAATATCCACAAG
CTGATTGAGCATCACAACCTCCCGGATCTCATGTTCCGTGCCTTTGAAGTTCTCCC
AACGATGATGATTACTCCGTATGCGGCGTTCCAAAAAGAGCTGCATGGCCAAACG
GAAGAGGTGTACCTCGAAGAAATGGTCGGTCGCGTTAATGCTAATATGATTCTCCC
GTATCCACCTGGTGTGCCTCTCGTTATGCCAGGCGAAATGATCACTGAAGAGTCCC
GCCCAGTGCTCGAATTTCTGCAAATGCTGTGTGAAATTGGCGCCCACTACCCAGG
CTTCGAAACCGATATTCATGGCGCTTACCGCCAAGCAGATGGTCGCTACACGGTTA
AAGTACTCAAGGAAGAGAACAACAAATAA
```

(*K. oxytoca* Ldc T398S amino acid sequence)   SEQ ID NO: 7

```
MNVIAIMNHMGVYFKEEPIRELHRALERLDFRIVYPNDREDLLKLIENNA
RLCGVIFDWDKYNLELCEDISKMNEYMPLYAFANTYSTLDVSLNDLRMQV
RFFEYALGAAEDIANKIKQNTDEYIDTILPPLTKALFKYVREGKYTFCTP
GHMGGTAFQKSPVGSIFYDFFGSNTMKSDISISVSELGSLLDHSGPHKEA
EEYIARVFNAERSYMVTNGTSTANKIVGMYSAPAGSTVLIDRNCHKSLTH
LMMMSDITPIYFRPTRNAYGILGGIPQSEFQHATIAKRVKETPNATWPVH
AVITNSTYDGLLYNTDYIKKTLDVKSIHFDSAWVPYTNFSPIYEGKCGMS
GGRVEGKVIYETQSTHKLLAAFSQASMIHVKGDVNEETFNEAYMMHTSTS
PHYGVVASTETAAAMMKGNAGKRLIDGSIERSIKFRKEIKRLKGESDGWF
FDVWQPEHIDGAECWPLRSDSAWHGFKNIDNEHMYLDPIKVTLLTPGMKK
DGTMDEFGIPASIVAKYLDEHGIVVEKTGPYNLLFLFSIGIDKTKALSLL
RALTDFKRAFDLNLRVKNMLPSLYREDPEFYENMRVQELAQNIHKLIEHH
NLPDLMFRAFEVLPTMMITPYAAFQKELHGQTEEVYLEEMVGRVNANMIL
PYPPGVPLVMPGEMITEESRPVLEFLQMLCEIGAHYPGFETDIHGAYRQA
DGRYTVKVLKEENNK
```

(*K. oxytoca* ldc-co1 C1306G nucleotide sequence)   SEQ ID NO: 8

```
ATGAATGTTATTGCGATTATGAACCACATGGGCGTATACTTCAAGGAGGAACCGAT
CCGCGAACTGCATCGTGCCCTGGAACGTCTGGATTTCCGCATCGTCTATCCAAATG
ACCGTGAGGATCTCCTCAAGCTCATCGAGAATAATGCGCGCCTGTGTGGTGTTATC
TTTGACTGGGACAAATACAATCTGGAACTGTGCGAGGACATCTCTAAGATGAACGA
```

```
ATATATGCCGCTGTACGCGTTTGCCAACACCTACTCTACCCTCGACGTTAGCCTGA
ATGACCTGCGCATGCAGGTTCGTTTCTTTGAATACGCGCTGGGTGCGGCGGAAGA
CATTGCAAACAAGATCAAACAAAACACCGACGAGTACATTGATACGATCCTCCCTC
CTCTCACCAAAGCTCTGTTCAAGTACGTCCGCGAGGGCAAGTACACTTTTTGCACC
CCTGGTCATATGGGCGGCACTGCGTTTCAGAAAAGCCCGGTTGGTTCCATTTTCTA
TGACTTTTTTGGTTCTAATACGATGAAATCTGATATCTCTATCTCTGTTTCCGAACTC
GGCTCCCTGCTGGACCACTCTGGTCCGCATAAAGAAGCAGAAGAATACATCGCGC
GTGTTTTCAACGCGGAACGCTCTTACATGGTAACGAACGGCACCAGCACCGCGAA
TAAGATTGTTGGTATGTATAGCGCTCCAGCGGGCTCTACCGTACTCATTGACCGTA
ACTGCCATAAAAGCCTGACTCACCTCATGATGATGTCCGACATCACTCCAATTTACT
TCCGTCCGACCCGTAATGCCTATGGCATCCTGGGTGGCATTCCTCAGTCTGAATTT
CAACACGCCACTATTGCTAAGCGTGTAAAGGAGACTCCAAACGTACGTGGCCTG
TCCACGCCGTTATCACCAACTCCACCTACGACGGTCTCCTGTACAATACTGATTAC
ATCAAAAAAACCCTGGATGTAAAATCCATTCACTTCGATAGCGCATGGGTTCCTTAC
ACTAACTTCAGCCCAATCTATGAGGGTAAGTGCGGTATGAGCGGTGGTCGTGTCG
AAGGCAAAGTTATCTACGAGACGCAAAGCACTCACAAACTCCTGGCAGCGTTCTCT
CAAGCGTCCATGATTCATGTTAAGGGTGACGTGAATGAAGAGACCTTCAACGAAGC
GTACATGATGCATACCACCACCTCTCCGCACTACGGTGTCGTTGCGTCCACGGAA
ACGGCGGCTGCTATGATGAAAGGTAATGCGGGTAAACGCCTGATCGACGGTTCTA
TTGAGCGTAGCATCAAATTTGTAAAGAAATCAAACGTCTCAAAGGTGAAAGCGAC
GGCTGGTTTTTCGATGTGTGGCAGCCAGAACATATTGATGGTGCTGAATGCTGGC
CGCTGCGTTCTGACTCCGCTTGGCACGGTTTCAAAAACATCGACAATGAACACATG
TACCTGGACCCGATCAAGGTTACGCTCCTGACCCCAGGTATGAAAAAAGACGGTA
CTATGGATGAATTCGGTATTCCGGCCTCCATCGTGGCGAAGTATCTCGACGAACAT
GGCATTGTTGTGGAGAAGACGGGTCCGTATAACCTGCTGTTTCTGTTTTCCATCGG
CATTGACAAAACGAAAGCGCTGTCTCTGCTGCGTGCGCTGACCGACTTTAAACGT
GCGTTCGACCTGAATCTCCGTGTTAAGAACATGCTCCCGTCTCTGTACCGTGAAGA
CCCGGAATTCTACGAAAACATGCGTGTTCAGGAACTGGCGCAGAATATCCACAAG
CTGATTGAGCATACACAACCTCCCGGATCTCATGTTCCGTGCCTTTGAAGTTCTCCC
AACGATGATGATTACTCCGTATGCGGCGTTCCAAAAAGAGCTGCATGGCCAAACG
GAAGAGGTGTACCTCGAAGAAATGGTCGGTCGCGTTAATGCTAATATGATTCTCCC
GTATCCACCTGGTGTGCCTCTCGTTATGCCAGGCGAAATGATCACTGAAGAGTCCC
GCCCAGTGCTCGAATTTCTGCAAATGCTGTGTGAAATTGGCGCCCACTACCCAGG
CTTCGAAACCGATATTCATGGCGCTTACCGCCAAGCAGATGGTCGCTACACGGTTA
AAGTACTCAAGGAAGAGAACAACAAATAA
```

(*K. oxytoca* Ldc R436G amino acid sequence)    SEQ ID NO: 9

```
MNVIAIMNHMGVYFKEEPIRELHRALERLDFRIVYPNDREDLLKLIENNA
RLCGVIFDWDKYNLELCEDISKMNEYMPLYAFANTYSTLDVSLNDLRMQV
RFFEYALGAAEDIANKIKQNTDEYIDTILPPLTKALFKYVREGKYTFCTP
GHMGGTAFQKSPVGSIFYDFFGSNTMKSDISISVSELGSLLDHSGPHKEA
EEYIARVFNAERSYMVTNGTSTANKIVGMYSAPAGSTVLIDRNCHKSLTH
```

LMMMSDITPIYFRPTRNAYGILGGIPQSEFQHATIAKRVKETPNATWPVH

AVITNSTYDGLLYNTDYIKKTLDVKSIHFDSAWVPYTNFSPIYEGKCGMS

GGRVEGKVIYETQSTHKLLAAFSQASMIHVKGDVNEETFNEAYMMHTTTS

PHYGVVASTETAAAMMKGNAGKRLIDGSIERSIKFGKEIKRLKGESDGWF

FDVWQPEHIDGAECWPLRSDSAWHGFKNIDNEHMYLDPIKVTLLTPGMKK

DGTMDEFGIPASIVAKYLDEHGIVVEKTGPYNLLFLFSIGIDKTKALSLL

RALTDFKRAFDLNLRVKNMLPSLYREDPEFYENMRVQELAQNIHKLIEHH

NLPDLMFRAFEVLPTMMITPYAAFQKELHGQTEEVYLEEMVGRVNANMIL

PYPPGVPLVMPGEMITEESRPVLEFLQMLCEIGAHYPGFETDIHGAYRQA

DGRYTVKVLKEENNK (*K. oxytoca* ldc-co1 C1521G nucleotide sequence)     SEQ ID NO: 10

ATGAATGTTATTGCGATTATGAACCACATGGGCGTATACTTCAAGGAGGAACCGAT

CCGCGAACTGCATCGTGCCCTGGAACGTCTGGATTTCCGCATCGTCTATCCAAATG

ACCGTGAGGATCTCCTCAAGCTCATCGAGAATAATGCGCGCCTGTGTGGTGTTATC

TTTGACTGGGACAAATACAATCTGGAACTGTGCGAGGACATCTCTAAGATGAACGA

ATATATGCCGCTGTACGCGTTTGCCAACACCTACTCTACCCTCGACGTTAGCCTGA

ATGACCTGCGCATGCAGGTTCGTTTCTTTGAATACGCGCTGGGTGCGGCGGAAGA

CATTGCAAACAAGATCAAACAAAACACCGACGAGTACATTGATACGATCCTCCCTC

CTCTCACCAAAGCTCTGTTCAAGTACGTCCGCGAGGGCAAGTACACTTTTTGCACC

CCTGGTCATATGGGCGGCACTGCGTTTCAGAAAAGCCCGGTTGGTTCCATTTTCTA

TGACTTTTTTGGTTCTAATACGATGAAATCTGATATCTCTATCTCTGTTTCCGAACTC

GGCTCCCTGCTGGACCACTCTGGTCCGCATAAAGAAGCAGAAGAATACATCGCGC

GTGTTTTCAACGCGGAACGCTCTTACATGGTAACGAACGGCACCAGCACCGCGAA

TAAGATTGTTGGTATGTATAGCGCTCCAGCGGGCTCTACCGTACTCATTGACC GTA

ACTGCCATAAAAGCCTGACTCACCTCATGATGATGTCCGACATCACTCCAATTTACT

TCCGTCCGACCCGTAATGCCTATGGCATCCTGGGTGGCATTCCTCAGTCTGAATTT

CAACACGCCACTATTGCTAAGCGTGTAAAGGAGACTCCAAACGCTACGTGGCCTG

TCCACGCCGTTATCACCAACTCCACCTACGACGGTCTCCTGTACAATACTGATTAC

ATCAAAAAAACCCTGGATGTAAAATCCATTCACTTCGATAGCGCATGGGTTCCTTAC

ACTAACTTCAGCCCAATCTATGAGGGTAAGTGCGGTATGAGCGGTGGTCGTGTCG

AAGGCAAAGTTATCTACGAGACGCAAAGCACTCACAAACTCCTGGCAGCGTTCTCT

CAAGCGTCCATGATTCATGTTAAGGGTGACGTGAATGAAGAGACCTTCAACGAAGC

GTACATGATGCATACCACCACCTCTCCGCACTACGGTGTCGTTGCGTCCACGGAA

ACGGCGGCTGCTATGATGAAAGGTAATGCGGGTAAACGCCTGATCGACGGTTCTA

TTGAGCGTAGCATCAAATTTCGTAAAGAAATCAAACGTCTCAAAGGTGAAAGCGAC

GGCTGGTTTTTCGATGTGTGGCAGCCAGAACATATTGATGGTGCTGAATGCTGGC

CGCTGCGTTCTGACTCCGCTTGGCACGGTTTCAAAAACATCGACAATGAACACATG

TACCTGGACCCGATCAAGGTTACGCTCCTGACCCCAGGTATGAAAAAAGACGGTA

CTATGGATGAATTGGTATTCCGGCCTCCATCGTGGCGAAGTATCTCGACGAACAT

GGCATTGTTGTGGAGAAGACGGGTCCGTATAACCTGCTGTTTCTGTTTTCCATCGG

```
CATTGACAAAACGAAAGCGCTGTCTCTGCTGCGTGCGCTGACCGACTTTAAACGT

GCGTTCGACCTGAATCTCCGTGTTAAGAACATGCTCCCGTCTCTGTACCGTGAAGA

CCCGGAATTCTACGAAAACATGCGTGTTCAGGAACTGGCGCAGAATATCCACAAG

CTGATTGAGCATCACAACCTCCCGGATCTCATGTTCCGTGCCTTTGAAGTTCTCCC

AACGATGATGATTACTCCGTATGCGGCGTTCCAAAAAGAGCTGCATGGCCAAACG

GAAGAGGTGTACCTCGAAGAAATGGTCGGTCGCGTTAATGCTAATATGATTCTCCC

GTATCCACCTGGTGTGCCTCTCGTTATGCCAGGCGAAATGATCACTGAAGAGTCCC

GCCCAGTGCTCGAATTTCTGCAAATGCTGTGTGAAATTGGCGCCCACTACCCAGG

CTTCGAAACCGATATTCATGGCGCTTACCGCCAAGCAGATGGTCGCTACACGGTTA

AAGTACTCAAGGAAGAGAACAACAAATAA
```

(K. oxytoca Ldc F507L amino acid sequence)  SEQ ID NO: 11

```
MNVIAIMNHMGVYFKEEPIRELHRALERLDFRIVYPNDREDLLKLIENNA

RLCGVIFDWDKYNLELCEDISKMNEYMPLYAFANTYSTLDVSLNDLRMQV

RFFEYALGAAEDIANKIKQNTDEYIDTILPPLTKALFKYVREGKYTFCTP

GHMGGTAFQKSPVGSIFYDFFGSNTMKSDISISVSELGSLLDHSGPHKEA

EEYIARVFNAERSYMVTNGTSTANKIVGMYSAPAGSTVLIDRNCHKSLTH

LMMMSDITPIYFRPTRNAYGILGGIPQSEFQHATIAKRVKETPNATWPVH

AVITNSTYDGLLYNTDYIKKTLDVKSIHFDSAWVPYTNFSPIYEGKCGMS

GGRVEGKVIYETQSTHKLLAAFSQASMIHVKGDVNEETFNEAYMMHTTTS

PHYGVVASTETAAAMMKGNAGKRLIDGSIERSIKFRKEIKRLKGESDGWF

FDVWQPEHIDGAECWPLRSDSAWHGFKNIDNEHMYLDPIKVTLLTPGMKK

DGTMDELGIPASIVAKYLDEHGIVVEKTGPYNLLFLFSIGIDKTKALSLL

RALTDFKRAFDLNLRVKNMLPSLYREDPEFYENMRVQELAQNIHKLIEHH

NLPDLMFRAFEVLPTMMITPYAAFQKELHGQTEEVYLEEMVGRVNANMIL

PYPPGVPLVMPGEMITEESRPVLEFLQMLCEIGAHYPGFETDIHGAYRQA

DGRYTVKVLKEENNK
```

(K. oxytoca ldc-co1 T1820A nucleotide sequence)  SEQ ID NO: 12

```
ATGAATGTTATTGCGATTATGAACCACATGGGCGTATACTTCAAGGAGGAACCGAT

CCGCGAACTGCATCGTGCCCTGGAACGTCTGGATTTCCGCATCGTCTATCCAAATG

ACCGTGAGGATCTCCTCAAGCTCATCGAGAATAATGCGCGCCTGTGTGGTGTTATC

TTTGACTGGGACAAATACAATCTGGAACTGTGCGAGGACATCTCTAAGATGAACGA

ATATATGCCGCTGTACGCGTTTGCCAACACCTACTCTACCCTCGACGTTAGCCTGA

ATGACCTGCGCATGCAGGTTCGTTTCTTTGAATACGCGCTGGGTGCGGCGGAAGA

CATTGCAAACAAGATCAAACAAAACACCGACGAGTACATTGATACGATCCTCCCTC

CTCTCACCAAAGCTCTGTTCAAGTACGTCCGCGAGGGCAAGTACACTTTTTGCACC

CCTGGTCATATGGGCGGCACTGCGTTTCAGAAAAGCCCGGTTGGTTCCATTTTCTA

TGACTTTTTTGGTTCTAATACGATGAAATCTGATATCTCTATCTCTGTTTCCGAACTC

GGCTCCCTGCTGGACCACTCTGGTCCGCATAAAGAAGCAGAAGAATACATCGCGC

GTGTTTTCAACGCGGAACGCTCTTACATGGTAACGAACGGCACCAGCACCGCGAA

TAAGATTGTTGGTATGTATAGCGCTCCAGCGGGCTCTACCGTACTCATTGACCGTA

ACTGCCATAAAAGCCTGACTCACCTCATGATGATGTCCGACATCACTCCAATTTACT
```

-continued

```
TCCGTCCGACCCGTAATGCCTATGGCATCCTGGGTGGCATTCCTCAGTCTGAATTT

CAACACGCCACTATTGCTAAGCGTGTAAAGGAGACTCCAAACGCTACGTGGCCTG

TCCACGCCGTTATCACCAACTCCACCTACGACGGTCTCCTGTACAATACTGATTAC

ATCAAAAAAACCCTGGATGTAAAATCCATTCACTTCGATAGCGCATGGGTTCCTTAC

ACTAACTTCAGCCCAATCTATGAGGGTAAGTGCGGTATGAGCGGTGGTCGTGTCG

AAGGCAAAGTTATCTACGAGACGCAAAGCACTCACAAACTCCTGGCAGCGTTCTCT

CAAGCGTCCATGATTCATGTTAAGGGTGACGTGAATGAAGAGACCTTCAACGAAGC

GTACATGATGCATACCACCACCTCTCCGCACTACGGTGTCGTTGCGTCCACGGAA

ACGGCGGCTGCTATGATGAAAGGTAATGCGGGTAAACGCCTGATCGACGGTTCTA

TTGAGCGTAGCATCAAATTTCGTAAAGAAATCAAACGTCTCAAAGGTGAAAGCGAC

GGCTGGTTTTTCGATGTGTGGCAGCCAGAACATATTGATGGTGCTGAATGCTGGC

CGCTGCGTTCTGACTCCGCTTGGCACGGTTTCAAAAACATCGACAATGAACACATG

TACCTGGACCCGATCAAGGTTACGCTCCTGACCCCAGGTATGAAAAAAGACGGTA

CTATGGATGAATTCGGTATTCCGGCCTCCATCGTGGCGAAGTATCTCGACGAACAT

GGCATTGTTGTGGAGAAGACGGGTCCGTATAACCTGCTGTTTCTGTTTTCCATCGG

CATTGACAAAACGAAAGCGCTGTCTCTGCTGCGTGCGCTGACCGACTTTAAACGT

GCGTTCGACCTGAATCTCCGTGTTAAGAACATGCTCCCGTCTCTGTACCGTGAAGA

CCCGGAATTCTACGAAAACATGCGTGTTCAGGAACTGGCGCAGAATATCCACAAG

CTGATTGAGCATCACAACCTCCCGGATCTCATGTACCGTGCCTTTGAAGTTCTCCC

AACGATGATGATTACTCCGTATGCGGCGTTCCAAAAAGAGCTGCATGGCCAAACG

GAAGAGGTGTACCTCGAAGAAATGGTCGGTCGCGTTAATGCTAATATGATTCTCCC

GTATCCACCTGGTGTGCCTCTCGTTATGCCAGGCGAAATGATCACTGAAGAGTCCC

GCCCAGTGCTCGAATTTCTGCAAATGCTGTGTGAAATTGGCGCCCACTACCCAGG

CTTCGAAACCGATATTCATGGCGCTTACCGCCAAGCAGATGGTCGCTACACGGTTA

AAGTACTCAAGGAAGAGAACAACAAATAA
```

(*K. oxytoca* Ldc F607Y amino acid sequence)    SEQ ID NO: 13

```
MNVIAIMNHMGVYFKEEPIRELHRALERLDFRIVYPNDREDLLKLIENNA

RLCGVIFDWDKYNLELCEDISKMNEYMPLYAFANTYSTLDVSLNDLRMQV

RFFEYALGAAEDIANKIKQNTDEYIDTILPPLTKALFKYVREGKYTFCTP

GHMGGTAFQKSPVGSIFYDFFGSNTMKSDISISVSELGSLLDHSGPHKEA

EEYIARVFNAERSYMVTNGTSTANKIVGMYSAPAGSTVLIDRNCHKSLTH

LMMMSDITPIYFRPTRNAYGILGGIPQSEFQHATIAKRVKETPNATWPVH

AVITNSTYDGLLYNTDYIKKTLDVKSIHFDSAVVVPYTNFSPIYEGKCGMS

GGRVEGKVIYETQSTHKLLAAFSQASMIHVKGDVNEETFNEAYMMHTTTS

PHYGVVASTETAAAMMKGNAGKRLIDGSIERSIKFRKEIKRLKGESDGWF

FDVWQPEHIDGAECWPLRSDSAWHGFKNIDNEHMYLDPIKVTLLTPGMKK

DGTMDEFGIPASIVAKYLDEHGIVVEKTGPYNLLFLFSIGIDKTKALSLL

RALTDFKRAFDLNLRVKNMLPSLYREDPEFYENMRVQELAQNIHKLIEHH
```

NLPDLMFRAFEVLPTMMITPYAAFQKELHGQTEEVYLEEMVGRVNANMIL

PYPPGVPLVMPGEMITEESRPVLEFLQMLCEIGAHYPGFETDIHGAYRQA

DGRYTVKVLKEENNK (RBS DNA-1) SEQ ID NO: 14
GGAGAT (RBS DNA-2) SEQ ID NO: 15
AGGACT (RBS DNA-3) SEQ ID NO: 16
GAGGAG (RBS DNA-4) SEQ ID NO: 17
GAGGAA (RBS DNA-5) SEQ ID NO: 18
TGGAGG (RBS DNA-6) SEQ ID NO: 19
CAGGAG (Plac promoter nucleotide sequence) SEQ ID NO: 20
TTTACACTTTATGCTTCCGGCTCGTATGTTG (Pbad promoter nucleotide sequence) SEQ ID NO: 21
GACGCTTTTTATCGCAACTCTCTACTGT (Ptac promoter nucleotide sequence) SEQ ID NO: 22
TTGACAATTAATCATCGGCTCGTATAATG (aat nucleotide sequence)
>gb|AY271828.1|:385-1717 *H. alvei* plasmid pAlvA, complete sequence
SEQ ID NO: 23
```
   1 ttgactttgt taaaagtcag gcataagatc aaaatactgt atatataaca atgtatttat
  61 atacagtatt ttatactttt tatctaacgt cagagagggc aatattatga gtggtggaga
 121 tggcaagggt cacaatagtg gagcacatga ttccggtggc agcattaatg gaacttctgg
 181 gaaaggtggg ccatcaagcg gaggagcatc agataattct gggtggagtt cggaaaataa
 241 cccgtggggc ggtggtaact cgggaatgat tggtggcagt caaggaggta acggagctaa
 301 tcatggtggc gaaaatacat cttctaacta tgggaaagat gtatcacgcc aaatcggtga
 361 tgcgatagcc agaaaggaag gcatcaatcc gaaaatattc actgggtact ttatccgttc
 421 agatggatat ttgatcggaa taacgccact tgtcagtggt gatgcctttg gcgttaatct
 481 tggcctgttc aataacaatc aaaatagtag tagtgaaaat aagggatgga atggaaggaa
 541 tggagatggc attaaaaata gtagccaagg tggatggaag attaaaacta atgaacttac
 601 ttcaaaccaa gtagctgctg ctaaatccgt tccagaacct aaaaatagta atattataa
 661 gtccatgaga gaagctagcg atgaggttat taattctaat ttaaaccaag ggcatggagt
 721 tggtgaggca gctagagctg aaagagatta cagagaaaaa gtaaagaacg caatcaatga
 781 taatagtccc aatgtgctac aggatgctat taaatttaca gcagattttt ataaggaagt
 841 ttttaacgct tacggagaaa aagccgaaaa actagccaag ttattagctg atcaagctaa
 901 aggtaaaaag atccgcaatg tagaagatgc attgaaatct tatgaaaaac acaaggctaa
 961 cattaacaaa aaaatcaatg cgaaagatcg cgaagctatc gccaaggctt tggagtctat
1020 ggatgtagaa aaagccgcaa aaatatatc caagttcagc aaaggactag gttgggttgg
```

```
    1081  cccagctatc gatataactg attggtttac agaattatac aaagcagtga aaactgataa 1141  ttggagatct ctttatgtta aaactgaaac tattgcagta gggctagctg caacccatgt 1201  caccgcctta gcattcagtg ctgtcttggg tgggcctata ggtattttag gttatggttt 1261  gattatggct ggggttgggg cgttagttaa cgagacaata gttgacgagg caaataaggt 1321  cattgggatt taa
```

(aai nucleotide sequence)
>gb|AY271828.1|:1734-2069 *H. alvei* plasmid pAlvA, complete sequence
SEQ ID NO: 24

```
      1  ctatatttta gcggtcacat tttttatttc aaaacaaaca gaaagaacac caataggaat 61  tgatgtcata aaaataaaaa taaaatacaa agtcattaaa tatgttttg gcacaccatc 121  cttaaaaaaa cctgttttcc aaaattcttt tttcgtatat ctaagcgctg ctttctctat 181  tagaaaccga gagaaaggaa atagaatagc gctagccaaa ccaaagattc tgagcgcaat 241  tattttaggt tcgtcatcac cataactggc gtaaagaata caagcagcca taaagtatcc 301  ccaaaacata ttatgtatgt aatatttcct tgtcat
```

(abt nucleotide sequence)
>gb|AY271829.1|:384-1566 *H. alvei* plasmid pAlvB, complete sequence
SEQ ID NO: 25

```
      1  atgagtggtg gagacggtaa aggtcacaat agtggagcac atgattccgg tgcagcatt 61  aatggaactt cggggaaagg tggacctgat tctggtggcg gatattggga caaccatcca 121  catattacaa tcaccggtgg acgggaagta ggtcaagggg gagctggtat caactggggt 181  ggtggttctg gtcatggtaa cggcgggggc tcagttgcca tccaagaata taacacgagt 241  aaatatccta acacggagg atttcctcct cttggagacg ctagctggct gttaaatcct 301  ccaaaatggt cggttattga agtaaaatca gaaaactcag catggcgctc ttatattact 361  catgttcaag gtcatgttta caaattgact tttgatggta cgggtaagct cattgatacc 421  gcgtatgtta attatgaacc cagtgatgat actcgttgga gcccgcttaa aagttttaaa 481  tataataaag gaaccgctga aaaacaggtt agggatgcca ttaacaatga aaagaagca 541  gttaaggacg ctgttaaatt tactgcagac ttctataaag aggtttttaa ggtttacgga 601  gaaaaagccg agaagctcgc taagttatta gcagatcaag ctaaaggcaa aaaggttcgc 661  aacgtagaag atgccttgaa atcttatgaa aaatataaga ctaacattaa caaaaaaatc 721  aatgcgaaag atcgcgaagc tattgctaaa gccttggagt ctatggatgt aggaaaagcc 781  gcaaaaaata tagccaagtt cagtaaagga ctaggttggg ttggccctgc tatcgatata 841  actgattggt ttacagaatt atacaaggca gtggaaactg ataattggag atcttttat 901  gttaaaactg aaactattgc agtagggcta gctgcaaccc atgttgccgc cttggcattc 961  agcgctgtct gggtgggcc tgtaggtatt ttgggttatg gttgattat ggctgggtt 1021  ggggcgttag ttaatgagac aatagttgac gaggcaaata aggttattgg gctttaa
```

(abi nucleotide sequence)
>gb|AY271829.1|:1583-1918 *H. alvei* plasmid pAlvB, complete sequence
SEQ ID NO: 26

```
      1  ctataattta gcggtcacat tttttatttc aaaaaaaaca gaaataacac ctataggaat 61  tgatgtcata aaaataaaaa ttaaaatacaa agtcattaaa tatgttttg gcacgccatc 121  cttaaaaaaa ccagtttccc aaaattcttt tttcgtatat ctaagcgcgg ttttctctat 181  taaaaaccga gagaaaggga ataggatagc actagccaaa ccaaagattc tgagcgcaat 241  tattttaggt tcgttatccc cataactggc gtaaagaata caaacagcca taaagtaccc 301  ccaaaacata ttatgtatat aatatttcct tgtcat
```

What is claimed is:

1. A product comprising:
a mutant lysine decarboxylase (Ldc) polypeptide of SEQ ID NO: 2, wherein the mutant Ldc polypeptide comprises the amino acid sequence selected from the group consisting of SEQ ID NO: 5 (i.e., *K. oxytoca* Ldc K287E), SEQ ID NO: 7 (i.e., *K. oxytoca* Ldc T398S), SEQ ID NO: 9 (i.e., *K. oxytoca* Ldc R436G), and SEQ ID NO: 11 (i.e., *K. oxytoca* Ldc F507L).

* * * * *